(12) United States Patent
Bennett et al.

(10) Patent No.: US 7,144,706 B2
(45) Date of Patent: Dec. 5, 2006

(54) METHODS OF MODULATING LOCALIZATION AND PHYSIOLOGICAL FUNCTION OF IP3 RECEPTORS

(75) Inventors: Vann Bennett, Hillsborough, NC (US); Anthony O. Gramolini, Toronto (CA); Peter J. Mohler, Iowa City, IA (US)

(73) Assignee: Duke University, Durham, NC (US)

( * ) Notice: Subject to any disclaimer, the term of this patent is extended or adjusted under 35 U.S.C. 154(b) by 104 days.

(21) Appl. No.: 10/336,031

(22) Filed: Jan. 3, 2003

(65) Prior Publication Data

US 2003/0167491 A1 Sep. 4, 2003

Related U.S. Application Data

(60) Provisional application No. 60/344,047, filed on Jan. 3, 2002.

(51) Int. Cl.
*G01N 33/53* (2006.01)
*G01N 33/567* (2006.01)

(52) U.S. Cl. .................................. 435/7.1; 435/7.21

(58) Field of Classification Search ................ 435/7.1, 435/7.21
See application file for complete search history.

(56) References Cited

U.S. PATENT DOCUMENTS 5,217,864 A * 6/1993 Heintz et al. .................. 435/6

OTHER PUBLICATIONS

Tuvia S, Anykrin-B is required for intracellular sorting of structurally diverse Ca2+ homeostasis proteins, 1999, J. of Cell Biology, vol. 147, pp. 995-1007.*
Bennett V, Physiological roles of axonal ankyrins in survival of premyelinated axons and localization of voltage-gated sodium channels, 1999, J. of Neurocytology, vol. 28, pp. 303-318.*
Nattel, Stanley, "Lost anchors cost lives", Nature 421:587-590 (2003).
Mohler et al, "A cardiac arrhythmia syndrome caused by loss of ankyrin-B function", PNAS 101(24):9137-9142 (2004).
Mohler et al, "Isoform Specificity among Ankyrins", The Journal of Biological Chemistry 279(24):25798-25804 (2004).
Mohler et al, "Inositol 1,4,5-Trisphosphate Receptor Localization and Stability in Neonatal Cardiomyocytes Requires Interaction with Ankyrin-B", The Journal of Biological Chemistry 279(13):12980-12987 (2004).
Mohler et al, "Ankyrin-B mutation causes type 4 long-QT cardiac arrhythmia and sudden cardiac death", Nature 421:634-639 (2003) and Supplementary Information.
Bennett and Lambert, "Physiological roles of axonal ankyrins in survival of premyelinated axons and localization of voltage-gated sodium channels", Journal of Neurocytology 28:303-318 (1999).
Chauhan et al, "Abnormal Cardiac $Na^+$ Channel Properties and QT Heart Rate Adaptation in Neonatal $Ankyrin_B$ Knockout Mice", Circ. Res. 86:441-447 (2000).
Gagelin et al, "Identification of $Ank_{G107}$, a Muscle-specific Ankyrin-G Isoform", The Journal of Biological Chemistry 277(15):12978-12987 (2002).
Hayashi and Su, "Regulating ankyrin dynamics: Roles of signa-1 receptors", PNAS 98(2):491-496 (2001).
Mohler et al, "The Ankyrin-B C-terminal Domain Determines Activity of Ankyrin-B/G Chimeras in Rescue of Abnormal Inositol 1,4,5-Triphosphate and Ryanodine Receptor Distrubtion in Ankyrin-B (-/-) Neonatal Cardiomyocytes", The Journal of Biological Chemistry 277(12):10599-10607 (2002).
Mohler et al, "Ankyrin-B mutation causes type 4 long-QT cardiac arrhythmia and sudden cardiac death", Nature 421:634-639 (2003).
Tuvia et al, "Ankyrin-B Is Required for Intracellular Sorting of Structurally Diverse $Ca^{2+}$ Homeostatis Proteins", The Journal of Cell Biology 147(5):995-1007 (1999).
Scotland et al, "Nervous System Defects of AnkyrinB (-/-) Mice Suggest Functional Overlap between the Cell Adhesion Molecule L1 and 440-kD AnkyrinB in Premyelinated Axons", The Journal of Cell Biology 143(5):1305-1315 (1998).

* cited by examiner

*Primary Examiner*—Peter Paras, Jr.
*Assistant Examiner*—David A. Montanari
(74) *Attorney, Agent, or Firm*—Nixon & Vanderhye PC

(57) ABSTRACT

The present invention relates, generally, to inositol 1,4,5-triphosphate receptors (IP3R), and, in particular, to methods of modulating the activity of 220 kDa ankyrin-B in cellular localization and physiological function of IP3R. The invention further relates to methods of identifying compounds suitable for use in such methods and to compounds so identified.

5 Claims, 41 Drawing Sheets

Fig. 7A
Fig. 7B
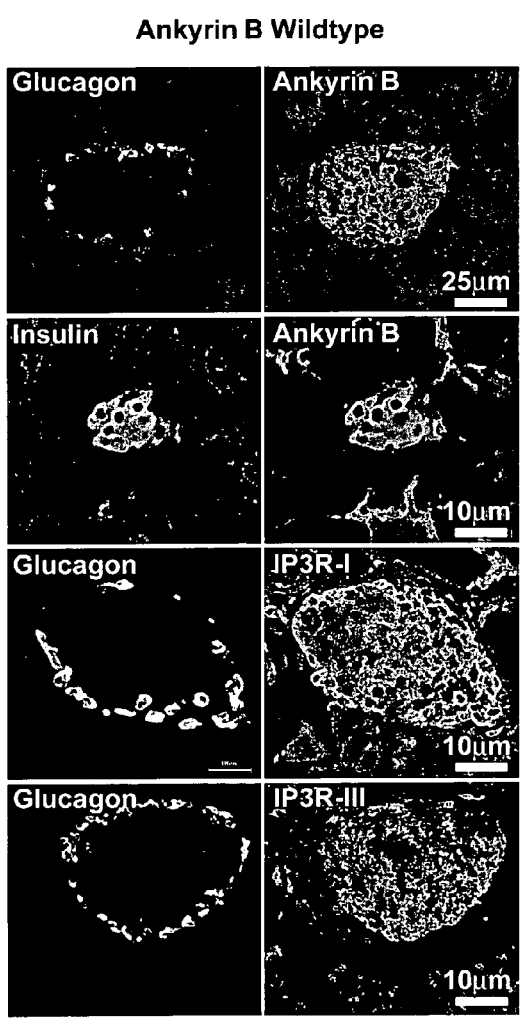
Ankyrin B Wildtype
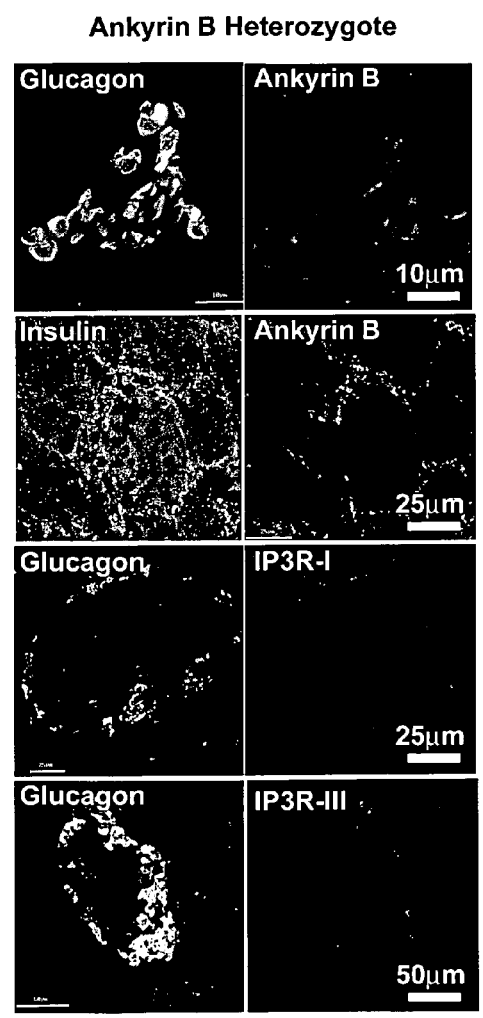
Ankyrin B Heterozygote

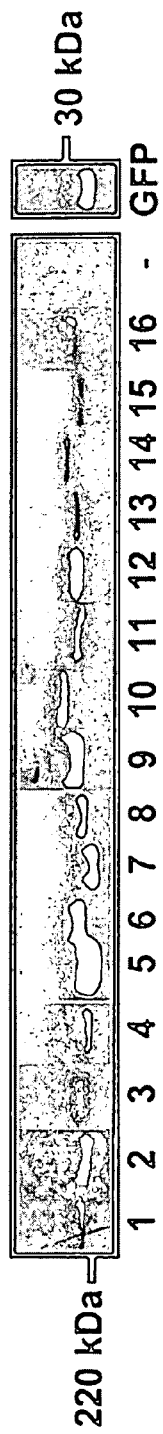
Fig. 13C
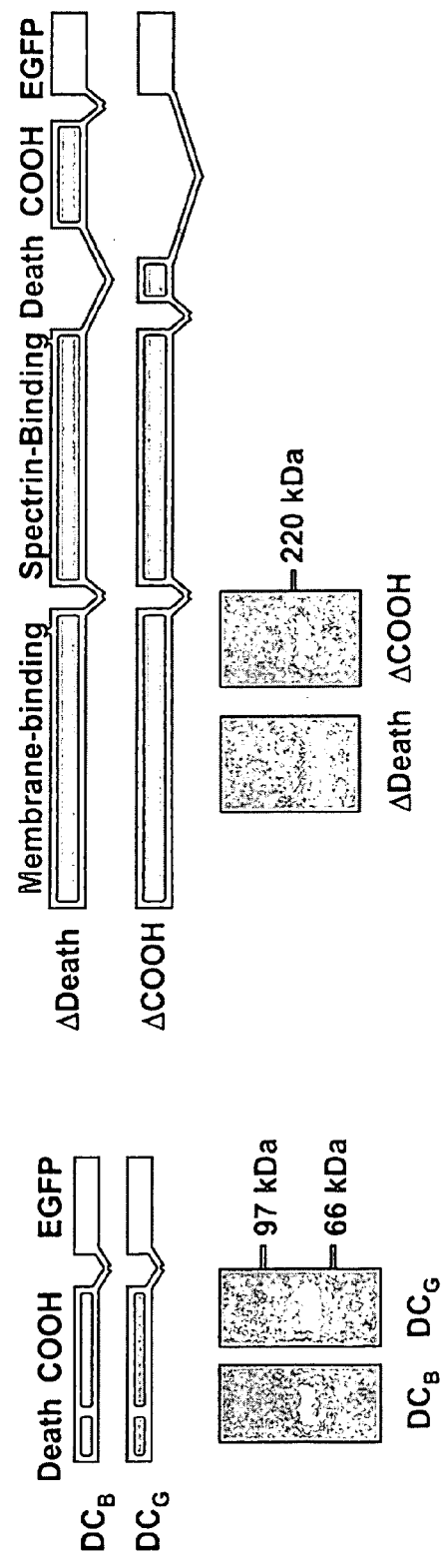
Fig. 13E
Fig. 13D

Fig. 14A

Ankyrin-B C-Terminal Domain Constructs

Ankyrin-B C-Terminal Domain Constructs

Ankyrin-B Baculovirus Constructs

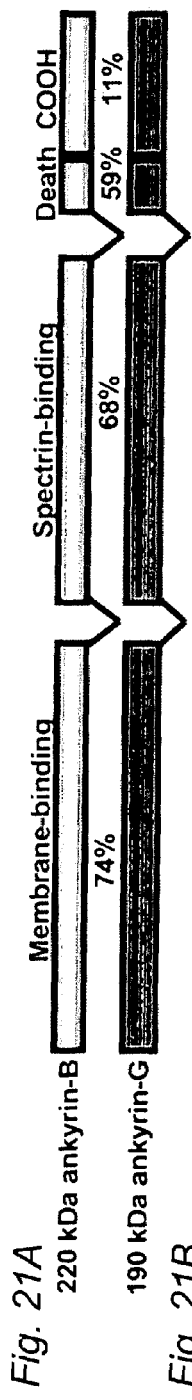
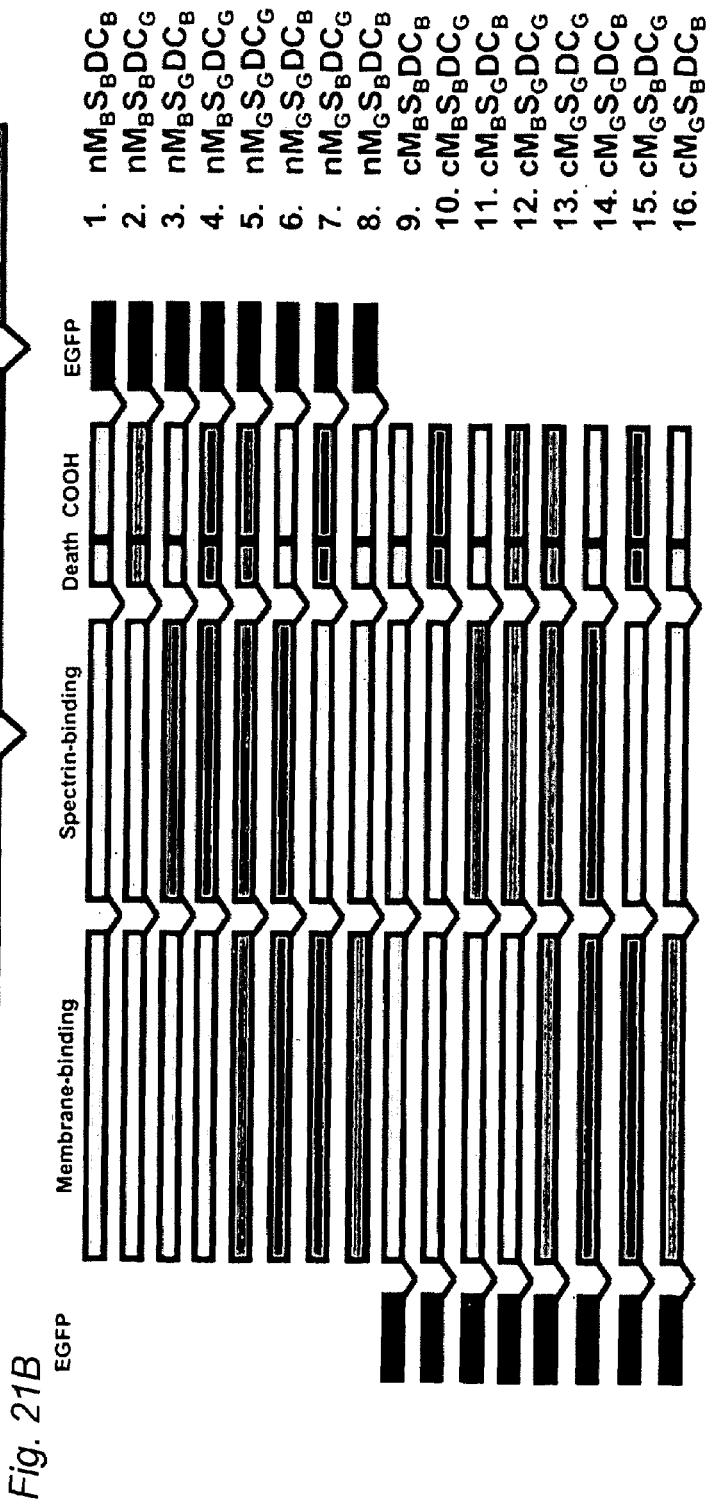
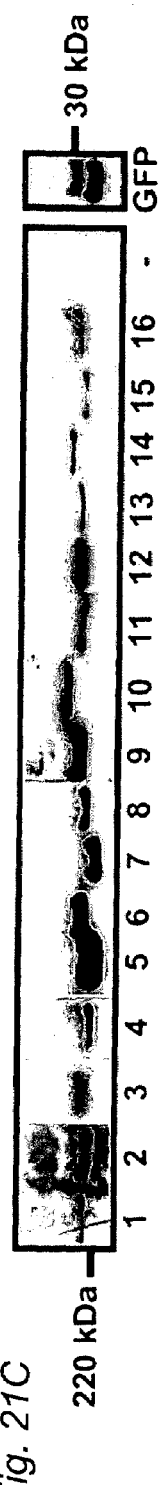
Fig. 21A
Fig. 21B
Fig. 21C

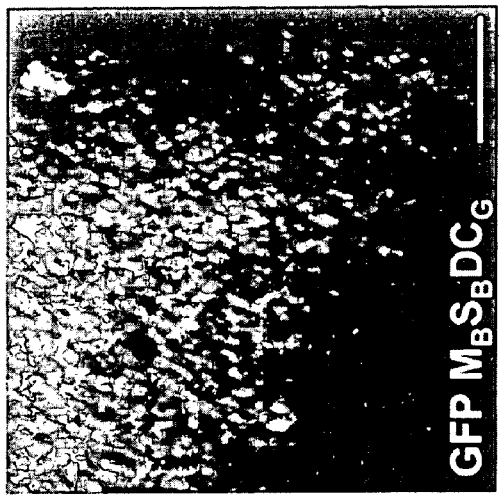
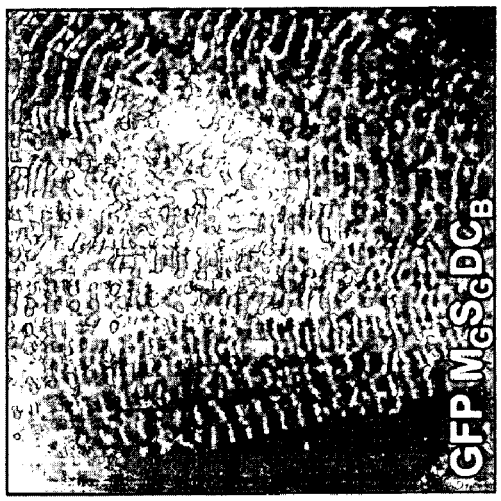
Fig. 23A
Fig. 23B

- ■ Affected Male
- ● Affected Female
- □ Unaffected Male
- ○ Unaffected Female
- ◐ Sinus Node Dysfunction
- ◑ Long QT Phenotype
- + E1425G carriers
- − E1425G non-carriers
- * Sudden death

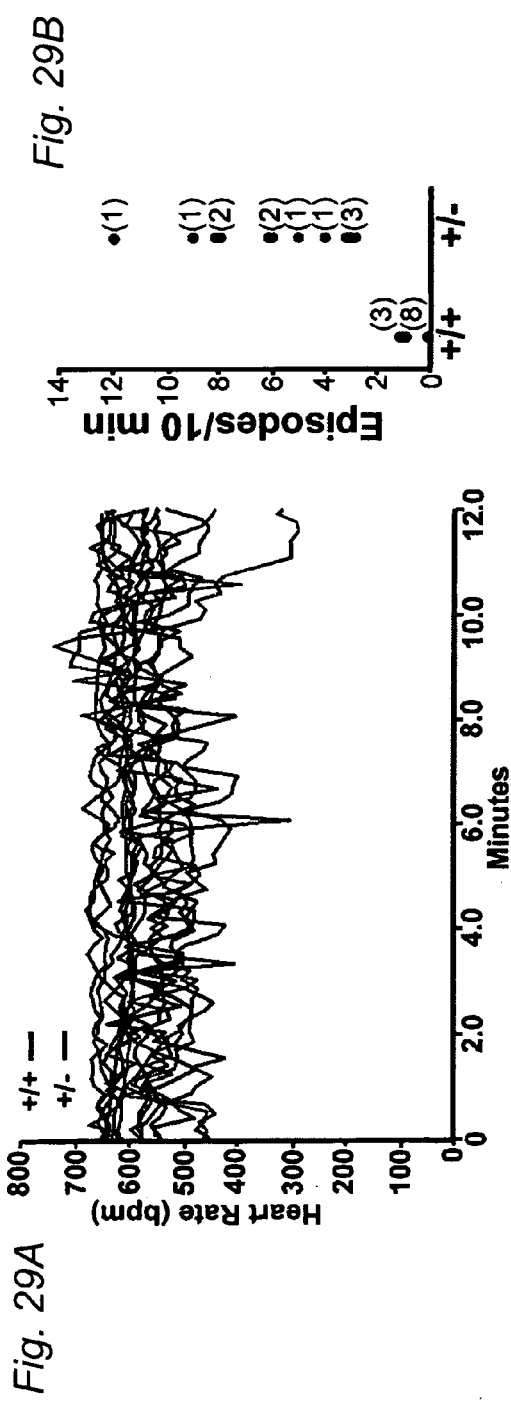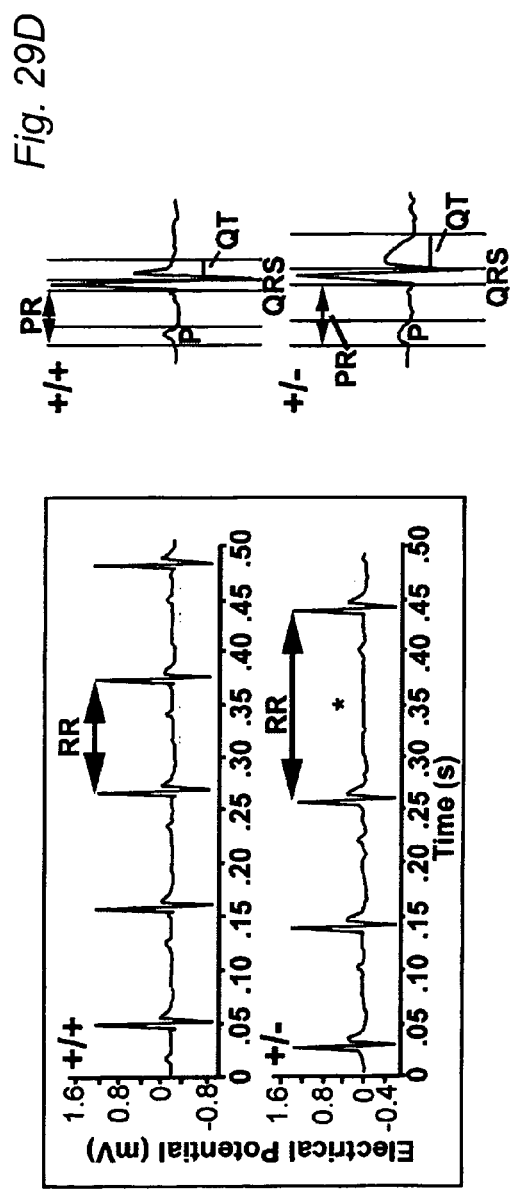

Ankyrin +/−

Isoproterenol (1 μM)

SEQUENCE LISTING

```
<160> NUMBER OF SEQ ID NOS: 3

<210> SEQ ID NO 1
<211> LENGTH: 396
<212> TYPE: PRT
<213> ORGANISM: Mus sp.

<400> SEQUENCE: 1

Pro Gln Asp Glu Gln Glu Arg Ile Glu Glu Arg Leu Ala Tyr Ile Ala
  1               5                  10                  15

Asp His Leu Gly Phe Ser Trp Thr Glu Leu Ala Arg Glu Leu Asp Phe
             20                  25                  30

Thr Glu Glu Gln Ile His Gln Ile Arg Ile Glu Asn Pro Asn Ser Leu
         35                  40                  45

Gln Asp Gln Ser Gln Tyr Leu Leu Lys Ile Trp Leu Glu Arg Asp Gly
     50                  55                  60

Lys His Ala Thr Asp Thr Asn Leu Val Glu Cys Leu Thr Lys Ile Asn
 65                  70                  75                  80

Arg Met Asp Ile Val His Leu Met Glu Thr Asn Thr Glu Pro Leu Gln
                 85                  90                  95

Glu Arg Ile Ser His Ser Tyr Ala Glu Ile Glu Gln Thr Ile Thr Leu
            100                 105                 110

Asp His Ser Glu Gly Phe Ser Val Leu Gln Glu Glu Leu Cys Thr Ala
        115                 120                 125

Gln His Lys Gln Lys Glu Glu Gln Ala Val Ser Lys Glu Ser Glu Thr
    130                 135                 140

Cys Asp His Pro Pro Ile Val Ser Glu Glu Asp Ile Ser Val Gly Tyr
145                 150                 155                 160

Ser Thr Phe Gln Asp Gly Val Pro Lys Thr Glu Gly Asp Ser Ser Ser
                165                 170                 175
```

-continued

```
Thr Ala Leu Phe Pro Gln Thr His Lys Glu Gln Val Gln Gln Asp Phe
            180                 185                 190

Ser Gly Lys Met Gln Asp Leu Pro Glu Glu Ser Ser Leu Glu Tyr Gln
        195                 200                 205

Gln Glu Tyr Phe Val Thr Thr Pro Gly Thr Glu Thr Ser Glu Thr Gln
    210                 215                 220

Lys Ala Met Ile Val Pro Ser Ser Pro Ser Lys Thr Pro Glu Glu Val
225                 230                 235                 240

Ser Thr Pro Ala Glu Glu Lys Leu Tyr Leu Gln Thr Pro Thr Ser
            245                 250                 255

Ser Glu Arg Gly Gly Ser Pro Ile Ile Gln Glu Pro Glu Glu Pro Ser
        260                 265                 270

Glu His Arg Glu Glu Ser Ser Pro Arg Lys Thr Ser Leu Val Ile Val
    275                 280                 285

Glu Ser Ala Asp Asn Gln Pro Glu Thr Cys Glu Arg Leu Asp Glu Asp
    290                 295                 300

Ala Ala Phe Glu Lys Gly Asp Asp Met Pro Glu Ile Pro Pro Glu Thr
305                 310                 315                 320

Val Thr Glu Glu Glu Tyr Ile Asp Glu His Gly His Thr Val Val Lys
                325                 330                 335

Lys Val Thr Arg Lys Ile Ile Arg Arg Tyr Val Ser Ser Glu Gly Thr
            340                 345                 350

Glu Lys Glu Glu Ile Met Val Gln Gly Met Pro Gln Glu Pro Val Asn
        355                 360                 365

Ile Glu Glu Gly Asp Gly Tyr Ser Lys Val Ile Lys Arg Val Val Leu
    370                 375                 380

Lys Ser Asp Thr Glu Gln Ser Glu Asp Asn Asn Glu
385                 390                 395

<210> SEQ ID NO 2
<211> LENGTH: 294
<212> TYPE: PRT
<213> ORGANISM: Mus sp.

<400> SEQUENCE: 2

Pro Gln Ser Pro Cys Glu Arg Thr Asp Ile Arg Met Ala Ile Val Ala
1               5                   10                  15

Asp His Leu Gly Leu Ser Trp Thr Glu Leu Ala Arg Glu Leu Asn Phe
            20                  25                  30

Ser Val Asp Glu Ile Asn Gln Ile Arg Val Glu Asn Pro Asn Ser Leu
        35                  40                  45

Ile Ser Gln Ser Phe Met Leu Leu Lys Lys Trp Val Thr Arg Asp Gly
    50                  55                  60

Lys Asn Ala Thr Thr Asp Ala Leu Thr Ser Val Leu Thr Lys Ile Asn
65                  70                  75                  80

Arg Ile Asp Ile Val Thr Leu Leu Glu Gly Pro Ile Phe Asp Tyr Gly
                85                  90                  95

Asn Ile Ser Gly Thr Arg Ser Phe Ala Asp Glu Asn Asn Val Phe His
            100                 105                 110

Asp Pro Val Asp Gly Trp Gln Asn Glu Thr Pro Ser Gly Ser Leu Glu
        115                 120                 125

Ser Pro Ala Gln Ala Arg Arg Ile Thr Gly Gly Leu Leu Asp Arg Leu
    130                 135                 140

Asp Asp Ser Ser Asp Gln Val Arg Asp Pro Ile Thr Ser Tyr Leu Thr
145                 150                 155                 160
```

```
Gly Glu Ala Gly Lys Phe Glu Ala Asn Gly Asn His Ala Glu Val Ile
                165                 170                 175
Pro Glu Ala Lys Ala Lys Ala Tyr Phe Pro Glu Ser Gln Asn Asp Ile
                180                 185                 190
Gly Lys Gln Ser Ile Lys Glu Asn Leu Lys Pro Lys Thr His Gly Cys
                195                 200                 205
Gly Arg Ala Glu Glu Pro Val Ser Pro Leu Thr Ala Tyr Gln Lys Ser
        210                 215                 220
Leu Glu Glu Thr Ser Lys Leu Val Ile Glu Asp Ala Pro Lys Pro Cys
225                 230                 235                 240
Val Pro Val Gly Met Lys Lys Met Thr Arg Thr Pro Ala Asp Gly Lys
                245                 250                 255
Ala Arg Leu Asn Leu Gln Glu Glu Gly Ser Ala Arg Ser Glu Pro
                260                 265                 270
Lys Gln Gly Glu Gly Tyr Lys Val Lys Thr Lys Lys Glu Ile Arg Asn
                275                 280                 285
Val Glu Lys Lys Ala His
        290

<210> SEQ ID NO 3
<211> LENGTH: 17
<212> TYPE: DNA
<213> ORGANISM: Mus sp.

<400> SEQUENCE: 3
gcggaaaggr atcagag                                                    17
```

METHODS OF MODULATING LOCALIZATION AND PHYSIOLOGICAL FUNCTION OF IP3 RECEPTORS

This application claims priority from U.S. Provisional Application No. 60/344,047, filed Jan. 3, 2002, the entire content of which is incorporated herein by reference.

TECHNICAL FIELD

The present invention relates, generally, to inositol 1,4,5-triphosphate receptors (IP3R), and, in particular, to methods of modulating the activity of 220 kDa ankyrin-B in cellular localization and physiological function of IP3R. The invention further relates to methods of identifying compounds suitable for use in such methods and to compounds so identified. The invention also relates to viable transgenic ankyrin-B (+/−) animals, to cells derived therefrom, and to methods of using same.

BACKGROUND

The $Ca^{2+}$ ion was first proposed as an intracellular messenger by Rasmussen in 1970 (Science 170:404–12), and now is known to be responsible for regulation of amazingly diverse physiological processes ranging from control of blood pressure and muscle contraction, release of insulin and other hormones, to immune and neurological memory (Bootman et al, Semin. Cell Dev. Biol. 12:3–10(2001); Clapham and Sneyd, Adv. Second Messenger Phosphoprotein Res. 30:1–24 (1995)). Moreover, elevation of $Ca^{2+}$ frequently occurs in the same cell in response to different signals with distinct consequences depending on the nature of the stimulus.

A general explanation for "broadband" signaling through $Ca^{2+}$ is that the molecules involved in $Ca^{2+}$ homeostasis are segregated into spatially privileged compartments minimizing uncontrolled crosstalk between signaling pathways (Berridge et al, Science 287:1604–1605 (2000)). Intracellular $Ca^{2+}$-release is primarily mediated by two families of $Ca^{2+}$-release channels, ryanodine (RyR) and inositol 1,4,5-trisphosphate receptors (IP3R), which are localized to the endoplasmic/sarcoplasmic reticulum (ER/SR) membrane. $Ca^{2+}$ released from ER stores through these channels diffuses submicron distances before being rapidly buffered or sequestered into mitochondria and/or the ER/SR lumen via the SR/ER CaATPase (SERCA) (Allbritton et al, Science 258:1812–1815 (1992)). These cycles of elementary $Ca^{2+}$ flux are the basis for local signaling events, and also represent the basic unit for global $Ca^{2+}$ events such as cardiac muscle contraction and relaxation (Ju and Allen, J. Physiol. 516:793–804 (1999)). Elevations in intracellular IP3 increase the frequency of elementary release of $Ca^{2+}$ from the ER/SR ('blips').

Based on the $Ca^{2+}$-induced calcium-release (CICR) properties of IP3R and RyR, localized elevation of $Ca^{2+}$, if concentrated near adjacent $Ca^{2+}$-release channels, can trigger additional $Ca^{2+}$-release leading to a considerably larger local release of $Ca^{2+}$ ('puffs'). On their own, these puffs are instrumental in local $Ca^{2+}$ regulatory mechanisms including exocytosis and ion channel activation (Rottingen and Iversen, Acta Physiol. Scand. 169:203–219 (2000)). However, the concerted action of many $Ca^{2+}$ puffs can activate local RyRs leading to $Ca^{2+}$ waves spreading across large distances. As a result, the generation of $Ca^{2+}$ waves and intracellular $Ca^{2+}$ signaling is dependent on the coupling of highly localized $Ca^{2+}$-release events to global $Ca^{2+}$ signaling mechanisms.

Regulation of specific $Ca^{2+}$-dependent cell signaling events is mediated by the tight spatial control of microdomain $Ca^{2+}$ concentrations due to the organization of $Ca^{2+}$-release proteins within the ER/SR in relation to each other, $Ca^{2+}$-effector proteins (ion channels, kinases), $Ca^{2+}$-uptake mechanisms (SERCA, mitochondria), as well as $Ca^{2+}$-buffering proteins. Therefore, the proper function of $Ca^{2+}$-release channels and thus, calcium, in a physiological context requires the appropriate spatial segregation of these proteins in cells.

Ankyrins are a family of membrane-associated proteins recently demonstrated to be required for targeting of ion channels to physiological sites in specialized membrane domains (Bennett and Chen, Current Opinion in Cell Biology 13:61–67 (2001)). Indeed, a role for ankyrin-B in cellular targeting of $Ca^{2+}$-release channels has recently been proposed based on observations that ankyrin biochemically interacts with RyR and IP3R (Bourguignon et al, J. Biol. Chem. 270:7257–7260 (1995); Bourguignon et al., J. Biol. Chem. 268:7290–7297 (1993); Hayashi and Su, Proc. Natl. Acad. Sci. USA 9:9 (2001); Joseph and Samanta, J. Biol. Chem. 268:6477–6486 (1993)), and that ankyrin-B null mice exhibit abnormal localization of calcium homeostasis proteins in cultured neonatal cardiomyocytes (Tuvia et al, J. Cell Biol. 147:995–1008 (1999)).

The present invention results, at least in part, from studies demonstrating that ankyrin-B is necessary for the subcellular segregation and/or trafficking of IP3R to specialized cellular sites, ultimately regulating spatially-privileged $Ca^{2+}$ dynamics via a conserved mechanism utilized in multiple cell types.

SUMMARY OF THE INVENTION

The present invention relates generally to IP3R. In one embodiment, the invention relates to methods of identifying compounds suitable for use in modulating the activity of 220 kDa ankyrin-B in cellular localization and function of IP3R. Additionally, the invention relates to therapies based on the use of compounds so identified. The invention further relates to viable transgenic ankyrin-B (+/−) animals, to cells derived therefrom, and to methods of using same. Other aspects of the invention and advantages thereof will be clear from the description that follows.

BRIEF DESCRIPTION OF THE DRAWINGS

(FIG. 1A) Photographs of (+/+) and AnkB (+/−) mice highlighting (left) significant hair loss and obesity; (right) anal cysts; and (lower) kyphosis. (FIG. 1B) Immunoblot analysis of AnkB protein levels in cardiac muscle. Protein levels in (+/+) and (+/−) hearts were quantitated using $^{125}$I-labeled protein A and expressed as percent of levels. (FIG. 1C) AnkB protein levels were determined in additional tissues and expressed as percent (+/+) levels (dashed line), n=3.

(FIG. 2A) Immunoblot analyses of IP3R, SERCA and RyR protein levels in adult cardiac muscle with position of 220 kDa marker. (FIG. 2B) [$^3$H]IP$_3$ binding assays and Scatchard analysis using cardiac muscle microsomes. (FIG. 2C) Quantitation of total IP3R protein levels in multiple adult tissues from the mouse and expressed as % of (+/+) levels. (FIG. 2D) Representative Northern blot analyses using mRNA from whole cardiac muscle and probed for IP3R type I, IP3R type I–IV (Pan) and GAPDH mRNA levels.

(FIG. 3A) Fluorescence of myocytes obtained from (+/+), (+/−) and (−/−) mice. (FIG. 3B) Distribution of AnkB along with IP3R or RyR in select AnkB (+/−) myocyte cultures. (FIG. 3C) Eight calcium images from spontaneously contracting cardiomyocytes treated with fluo3-AM. Data represent at least five separate experiments, with >10 myocytes analyzed/group for each experiment. Bar, 10 µm. Diagram of initial foci of $Ca^{2+}$-release (right) from (+/+) and (+/−) myocytes.

(FIG. 4A) Untransfected AnkB(+/−) cardiomyocytes as well as cells transfected with GFP-tagged AnkB were stained for AnkB and GFP, respectively, to show that GFP-AnkB restores proper IP3R (Pan) and RyR2 localization. (FIG. 4B) Quantitation of spontaneous contractions in (+/+) and AnkB (+/−) cardiomyocytes, or AnkB (+/−) cardiomyocytes mock transfected, or transfected with GFP 220 kDa AnkB or GFP alone (n>6). (FIG. 4C) Cytosolic $Ca^{2+}$ dynamics were obtained using fluo-3/AM from AnkB cultures transfected with GFP 220 kDa AnkB. Shown are 8 images from more than 300 frames. Final panel is the same fluo-3 imaged cell stained with GFP (red) and α-actinin antisera (green) to confirm that the cell was a transfected myocyte.

(FIG. 5A) RyR and IP3R (Type I) in cryostat sections of adult ventricular muscle obtained from (+/+) and (+/−) mice. Sections were double-labeled with α-actinin. (FIG. 5B) Immunolocalization of IP3R and RyR in cultured cardiomyocytes. Note the distinct subcellular localization of IP3R and RyR. (FIG. 5C) Immunolocalization of IP3R Type I and α-actinin in cryostat sections of cardiac Purkinje fibers with accompanying DIC images. Purkinje fibers are outlined. Bar, 25 µm.

(FIG. 6A) Heart rate of (+/+; solid) and AnkB (+/−; dashed) mice over 30 min. Episodes of increased PP interval, corresponding to marked sinus arrhythmia, are marked with asterisks. (FIG. 6B) Representative EKG traces obtained from (+/+; top) and (+/−; lower) mice show an example of sinus arrhythmia, which is indicated by an asterisk. Also marked are QRS complexes and the PP interval. (FIG. 6C) Multiple EKGs were analyzed and various parameters were quantitated. Shown are results for PR interval and corrected QT (QTc) interval obtained from (+/+) and (+/−) mice (P<0.05). (FIG. 6D) EKG traces obtained from (+/+; top) and (+/−; bottom) mice reveal that (+/−) mice display isorhythmic atrioventricular dissociation (small arrows highlight the floating P waves). The large arrow indicates slowing of the ventricular rate which results in the reappearance of P waves. For these experiments, n=9 (+/+) and 11 (+/−) mice.

FIGS. 7A–7D. AnkB (+/−) pancreas displays loss of IP3R and AnkB along with islet hypertrophy. Pancreas sections from (FIGS. 7A–7B) AnkB (+/−) mice were stained with antisera against glucagon, AnkB, insulin, IP3R type I, or IP3R type III. Shown are representative images from >20 islets obtained from 3 different animals in each group. Scale bars are indicated in the images. (FIG. 7C) Upper panel, (+/+) and (+/−) pancreas were sectioned and processed for H&E staining to visualize islets. Islet areas were determined by tracing the outline of the islets. Lower panel, sections were also analyzed by fluorescence using a glucagon antibody to visualize β-cells. (FIG. 7D) Islet size was determined by tracing the perimeter of the islets. N=6 mice/group with >70 islets measured.

(FIG. 8A) Fasting blood glucose levels from (+/+) and (+/−) mice were determined using a glucometer (n=19). (FIG. 8B) Fasted (+/+) and (+/−) mice were injected with glucose (2 g/kg body mass) or PBS and glucose levels were measured up to 120 min. Dark gray lines and symbols represent data from (+/−) whereas black lines and symbols represent (+/+) mice. Upper two traces show mice injected with glucose (n=15) and the bottom two traces represent mice injected with PBS (n=4). (FIG. 8C) Fasted (+/+) and AnkB (+/−) mice were injected with insulin (5 U/kg body mass) or PBS and glucose levels were measured up to 120 min. Data expressed as % basal blood glucose concentration (n=4 for (+/+) and n=8 for (+/−)).

(FIG. 1A) Shown are quantitative data of telemetry recordings of heart rate in beats per minute (BPM) in (+/+) and (+/−) mice prior to (control) and following phenylephrine (phenyl.) treatment. *represents significant differences from control levels (ie., pre-phenylephrine) while Ω represents a significant difference between wildtype and heterozygote mice following phenylephrine treatment. (FIG. 10B) Data are shown as percent of resting levels. * represents significant differences from wildtype changes. (FIG. 10C) Heart rate changes in response to $G\alpha_q$-stimulation with phenylephrine during beta blockade. Shown are quantitative data of telemetry recordings of heart rate in (+/+) and (+/−) mice prior to (control) and following propanolol, and propanolol/phenylephrine treatment. Both wildtype and heterozygote mice respond equally to propanolol, but the heterozygote displays significant differences with phenylephrine. *represents significant differences from control levels. (FIG. 10D) Data are shown as percent of resting levels. * represents significant differences from propanolol-alone levels. Black bars represent wildtype mice, while grey bars represent heterozygotes.

(FIG. 11A) Shown are quantitative data of telemetry recordings of heart rate in beats per minute (BPM) in (+/+) and (+/−) mice prior to (control) and following endothelin-1 treatment. Following endothelin-1 treatment, the maximum change in heart rate of the (+/−) does not reach the same levels as the wildtype. * represents significant differences from control levels (ie., pre-endothelin) while Ω represents a significant difference between wildtype and heterozygote mice following endothelin-1 treatment. (FIG. 11B) Data are shown as percent of resting levels. * represents significant differences from wildtype levels. Black bars represent wildtype mice, while grey bars represent heterozygotes FIGS. 12A and 12B. Heart rates in response to $G\alpha_s$-stimulation with isoproterenol.

FIGS. 13A–13E. Ankyrin-B/G cimeric and deletion constructs. (FIG. 13A) Shown schematically are major protein domains of 220 kDa ankyrin-B (top) and 190 kDa ankyrin-G (bottom). Scores represent percent amino acid identity between ankyrin-G and ankyrin-B within the corresponding regions. (FIG. 13B) Chimeric constructs were generated within the pEGFP backbones (NH2-terminally fused, represented by 'n' in the construct name; and COOH-terminally fused, represented by 'c') and contain various combinations of the membrane-binding, spectrin-binding, and death/C-terminal domains of 220 kDa ankyrin-B (light gray) and 190 kDa ankyrin-G (dark grey). (FIG. 13C) GFP-ankyrin chimeric constructs were confirmed by sequencing and protein expression in HEK293 cells using GFP-specific antisera. Numbers represent the corresponding constructs in (FIG. 13B). Symbols: −, untransfected cells; GFP, cells transfected with empty GFP vector. (FIG. 13D) Schematic diagram of death/C-terminal GFP constructs and confirmation of expression in HEK293 cells. (FIG. 13E) Schematic diagram of death or C-terminal deletion constructs and confirmation of expression in HEK293 cells.

Figure 14A:
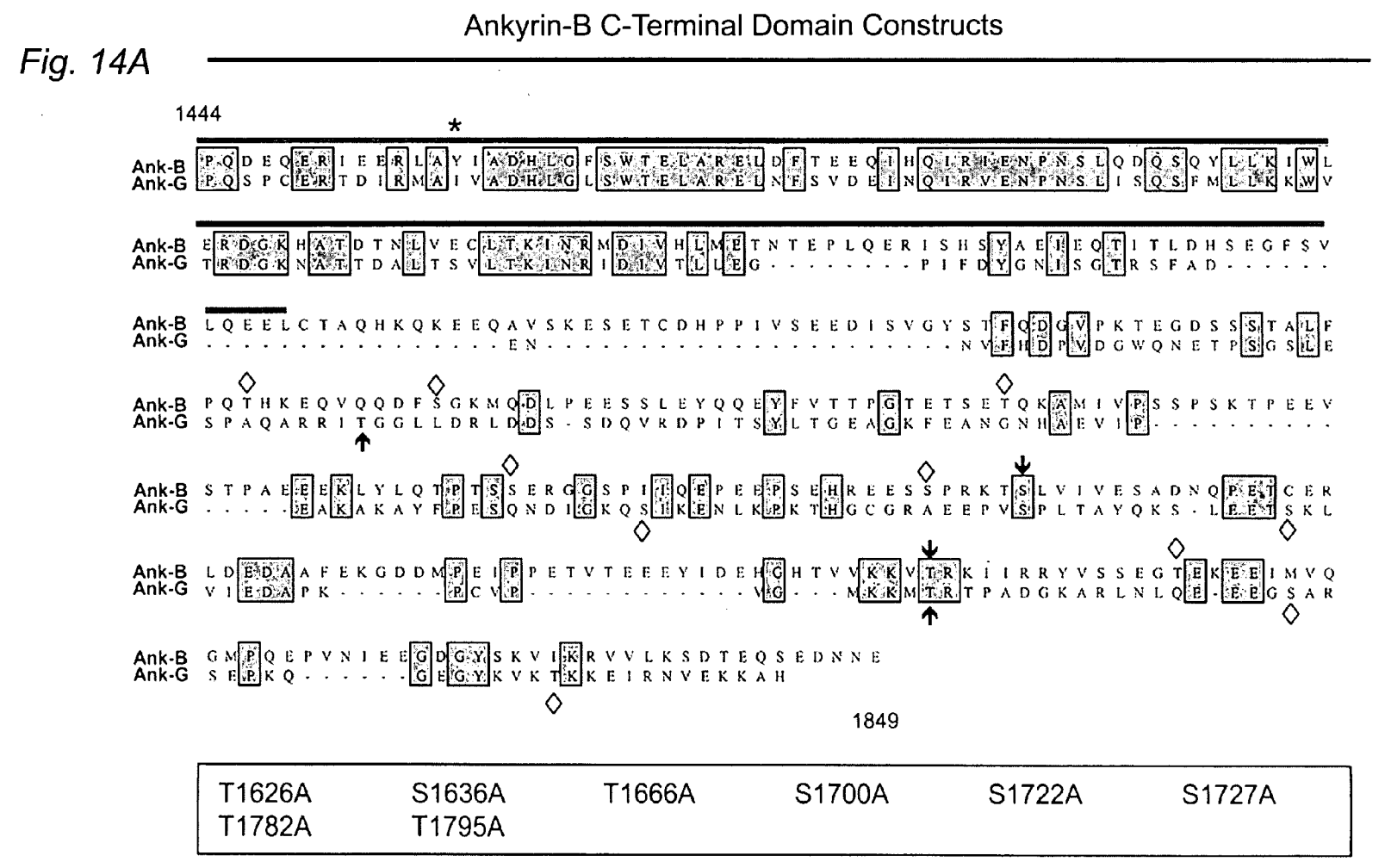

FIGS. 14A and 14B. Ankyrin-B C-terminal domain constructs. (FIG. 14A) The Death/C-Terminal domains of 220 kDa ankyrin-B (upper) (SEQ ID NO: 1) and 190 kDa ankyrin-G (lower) (SEQ ID NO: 2) which contain the death domain and the COOH-domain were aligned using MacVector (Accelrys; Burlington, Mass.). Shaded boxes represent conserved homology between these two molecules. The solid dark line above the sequence delineates the death domain. Symbols: arrows represent predicted PKA phosphorylation sites; open diamonds represent predicted PKC phosphorylation sites; and the asterisk shows one predicted tyrosine kinase site. (FIG. 14B) Schematic diagram of GST-fusion constructs.

(FIG. 15A) Representative schematic of full length GFP ankyrin-B constructs and constructs missing regions of the membrane-binding domain. (FIG. 15B) Schematic diagram of membrane-binding deletion constructs inserted in the pGEX-GST vector.

(FIG. 18A) Top panel, wildtype untransfected cardiomyocytes were co-labeled with α-actinin and ankyrin-B. Lower panels in FIG. 18A show ankyrin-B (−/−) cardiomyocytes transfected with 220 kDa ankyrin-B which was $NH_2$-(nGFP-AnkB) or COOH-terminally (cGFP-AnkB) fused with GFP and subsequently stained with α-actinin and GFP-antisera. (FIG. 18B) Wildtype untransfected cardiomyocytes were co-labeled with α-actinin and ankyrin-G (top panel), while the lower panels in FIG. 18B show ankyrin-B (−/−) cardiomyocytes transfected with 190 kDa GFP ankyrin-G (nGFP-AnkG and cGFP-AnkG) and subsequently stained with α-actinin and GFP-antisera. Scale bar, 5 μm. Data are representative of hundreds of transfected myocytes from more than ten different mice in each condition.

FIGS. 21A–21C. Ankyrin-B/G chimeric GFP-tagged expression constructs. (FIG. 21A) Shown schematically are major protein domains of 220 kDa ankyrin-B (top) and 190 kDa ankyrin-G (bottom). Scores represent percent amino acid identity between ankyrin-G and ankyrin-B within the corresponding regions. (FIG. 21B) Chimeric constructs were generated within the pEGFP backbones (NH2-terminally fused, represented by 'n' in the construct name; and COOH-terminally fused, represented by 'c') and contain various combinations of the membrane-binding, spectrin-binding, and death/C-terminal domains of 220 kDa ankyrin-B (gray) and 190 kDa ankyrin-G (black). (FIG. 21C) GFP-ankyrin chimeric constructs were confirmed by sequencing and protein expression in HEK293 cells using GFP-specific antisera. Numbers represent the corresponding constructs in (FIG. 21B). Symbols: −, untransfected cells; GFP, cells transfected with empty GFP vector.

FIGS. 23A and 23B. Chimeric ankyrin constructs that rescue IP3R localization in ankyrin-B (−/−) cardiomyocytes do not colocalize with IP3R. Shown are representative photomicrographs of cardiomyocyte cultures transfected with GFP-ankyrin M$_B$S$_B$DC$_G$ (FIG. 23B) and M$_G$S$_G$DC$_B$ (FIG. 23A) and subsequently immunostained with antisera to GFP and IP3 receptor. These constructs are not localized in a striated distribution pattern, nor do they restore the normal localization of IP3R. Representative images were taken from three separate experiments, each using at least three mice. Scale bar, 6 μm.

(FIG. 24A) Structural schematic of ankyrin-B, and ankyrin-G Death/C-Terminal domain constructs along with confirmation of chimera expression in HEK293 cells. Ankyrin-B (−/−) cardiomyocytes were transfected with the ankyrin-G GFP-Death/C-Terminal domain construct (FIG. 24B) and the ankyrin-B Death/C-Terminal domain construct (FIG. 24C) and subsequently immunostained with antisera to GFP and ryanodine receptor or IP3 receptor. Representative images were taken from three separate experiments, each using at least three mice. Although these constructs are expressed, they are unable to restore IP3 or ryanodine receptor localization. Scale bar, 5 μm FIGS. 25A–25C. The ankyrin-B C-terminal domain, but not the death domain, is necessary for striated localization of ankyrin-B and activity in rescuing IP3R and RyR localization in ankyrin-B (−/−) cardiomyocytes.

(FIG. 28A) Pedigree of LQT type 4 family. Filled symbols depict long QT and sinus node dysfunction phenotypes. (FIG. 28B) (SEQ ID NO: 3) A G mutation at position 4274 causes a mis-sense mutation with Glu Gly at position 1425 of afflicted patient. (FIG. 28C) Ca$^{2+}$ levels as a function of time (fold increase over basal levels (I/Io)). Graphs represent untransfected +/+ (i) and +/− neonatal cardiomyocytes (ii) and GFP-ankyrin-B (iii) and GFP-ankyrin-B E1425G (iv) transfected+/− myocytes. After Ca$^{2+}$ imaging, myocytes were monitored for GFP-ankyrin-B to ensure transfection.

FIGS. 29A–29F. Sinus bradycardia, heart rate variability, and sudden cardiac death in AnkB+/− mice. (FIG. 29A) Heart rates (7+/+, 7+/−) showing bradycardia and variability in AnkB+/− mice. (FIG. 29B) Episodes of variable heart rate (>±10% mean heart rate/animal) over 10 min (11+/+, 11+/−). (FIG. 29C) Sinus slowing in a +/− mouse ECG. (FIG. 29D) Sample +/+ and +/− ECGs. (FIG. 29E) +/− ECG traces at rest and following exercise (middle/right). (FIG. 29F) ECGs following exercise and epinephrine. Polymorphic ventricular arrhythmias occurred within ~17 min of EPI, followed by marked bradycardia and death 2 min after the arrhythmia. No +/+ mice exhibited ECG changes or died after these treatments.

(FIG. 30A) Quantitation of ankyrin-B protein expression in adult tissues (n=4). (FIG. 30B) Adult cardiomyocyte immunoprecipitations were analyzed for 220 kDa ankyrin-B (In=10% input). (FIG. 30C) Quantitative immunoblots of protein levels in adult cardiomyocytes (n=5). (FIGS. 30D,E) Ankyrin-B immunofluorescence in isolated +/+ and +/− adult cardiomyocytes (Arrows=Z-lines/T-tubules; Bars=5, 2.5 mm). (FIG. 30F) AnkB+/− cardiomyocytes display qualitative loss of NCX1, Na/K ATPase α1, α2, IP3R2 labeling over Z-line/T-tubules; Bar=40 μm. Loss of ankyrin-B associated protein staining at the Z-line/T-tubule was apparent throughout the entire depth of the cell.

(FIG. 31A) ICa density (0 mV) AnkB+/−=9.37+0.61 pA/pF and control=−8.87+/−0.60, ns. (FIG. 31B) Peak of [Ca$^{2+}$]i transient plotted as F/Fo. F/Fo for AnkB+/− is significantly greater than control at all membrane potentials. At 0 mV F/Fo for AnkB+/−=2.80+/−0.13 (n=18), control=2.41+/−0.12 (n=20), representing a 16.2% increase. (FIG. 31C) Steady-state APs recorded after 10–20 stimuli from AnkB+/− myocytes at 1 and 5 Hz in control solutions and in isoproterenol. Red arrows (up arrows) indicate stimuli timing. DADs and EADs were observed in 36% of AnkB+/− myocytes but in no control myocytes.

DETAILED DESCRIPTION OF THE INVENTION

Figure 1A:
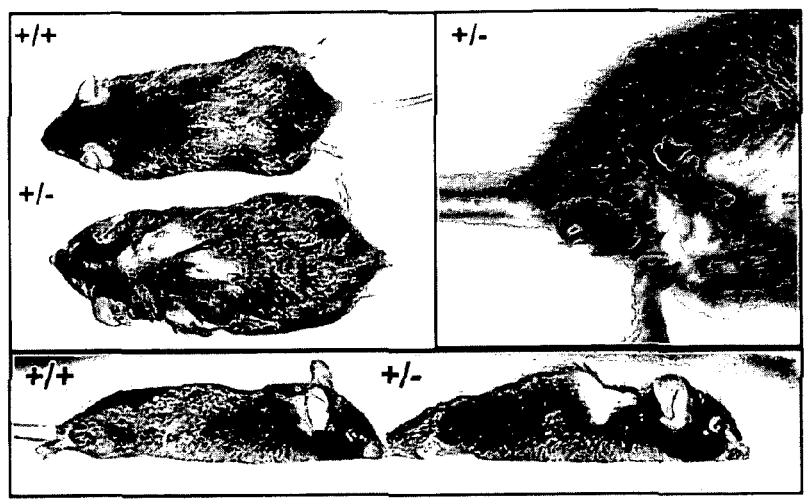
FIGS. 1A–1C. AnkB (+/−) mice display gross phenotypic differences and reduced AnkB expression.

IP3R-dependent Ca$^{2+}$-release is important to Gαq- and phospholipase C-coupled signaling pathways in numerous organs (e.g., heart, pancreas, brain, immune system) and is regulated by a variety of ligands (e.g., acetylcholine, endothelin, catecholamines, angiotensin II, purinergics, prostaglandins, tachykinins, bradykinin). IP3R are segregated into spatially privileged compartments within cells that allow optimal association with targets for IP3 receptor-released calcium and minimize nonspecific crosstalk between other signaling pathways that also utilize intracellular calcium. The present invention results, at least in part, from the realization that 220 kDa ankyrin-B is required for cellular targeting and/or accumulation specifically of IP3R (Types 1, 2, and 3) in adult heart, pancreas, brain, spleen, as well as other tissues (see Example 1), and that 220 kDa ankyrin-B (+/−) mice display reduced sensitivity to Gαq/IP3 receptor-dependent signaling (i.e., to α-adrenergic receptor agonists) (see Example 2). The invention provides methods of identifying agents that modulate the activity of 220 kDa ankyrin-B in cellular localization and physiological function of IP3R, and methods of identifying proteins other than IP3R that interact with 220 kDa ankyrin-B. The invention further provides a viable transgenic ankyrin-B (+/−) animal model and a set of genetically engineered chimeric ankyrin-B/ankyrin-G cDNA constructs, as well as mutated human ankyrin-B cDNA constructs, and to methods of using such constructs.

As indicated above, the present invention provides a method of screening test agents for their ability to enhance or inhibit the activity of 220 kDa ankyrin-B (and/or proteins that cooperate therewith) in cellular localization and physiological function of IP3R (or other 220 kDa ankyrin-B binding target). The method can take the form, for example, of a binding assay that comprises contacting the agent to be tested with 220 kDa ankyrin-B (or membrane-binding, spectin-binding, death or C-terminal domain thereof, or fusion protein comprising same) and with a binding target therefor (e.g., an IP3 receptor or portion thereof that binds 220 kDa ankyrin-B), and determining the effect of the test agent on the association of 220 kDa ankyrin-B (or membrane-binding domain thereof or fusion protein comprising same) with the binding target.

Such assays can take the form of cell-free competition binding assays. In one such assay, 220 kDa ankyrin-B, or binding domain thereof or fusion protein containing same, is incubated with the binding target (e.g., IP3 receptor or portion thereof that binds 220 kDa ankyrin-B), which binding target can bear a detectable label (e.g., a radioactive or fluorescent label). A test agent (proteinaceous or non-proteinaceous) can be added to the reaction and assayed for its ability to compete with the binding target for binding to 220 kDa ankyrin-B or binding domain thereof (or fusion protein). Free binding target can be separated from bound binding target, and the amount of bound target determined to assess the ability of the test compound to compete. This assay can be formatted so as to facilitate screening of large numbers of test agents, for example, by linking 220 kDa ankyrin-B, or binding domain thereof (or fusion protein), to a solid support so that it can be readily washed free of unbound reactants. It will be appreciated that the binding target, rather than 220 kDa ankyrin-B, can be bound to a support and that either or both can bear a detectable label (e.g., a fluorescent or radioactive label) (advantageously, different labels when both are label-bearing), as can the test agent.

220 kDa Ankyrin-B, or binding domain thereof (or fusion protein), suitable for use in assays such as that described above can be, as appropriate, isolated from natural sources (e.g., membrane preparations) or prepared recombinantly or chemically. 220 kDa Ankyrin-B, or binding domain thereof, can be prepared as a fusion protein using, for example, known recombinant techniques. Preferred fusion proteins include glutathione S-transferase and hexahistidine-tag fusions. The non 220 kDa-ankyrin-B moiety can be present in the fusion protein N-terminal or C-terminal to the 220 kDa ankyrin-B, or binding domain thereof.

As indicated above, 220 kDa ankyrin-B, or binding domain thereof or fusion protein, can be present linked to a solid support, including plastic plates, agarose and nitrocellulose. Methods of attachment of proteins to such supports are well known in the art and include direct chemical attachment and attachment via a binding pair (e.g., biotin and avidin or biotin and streptavidin).

In yet another embodiment, the present invention provides a heterozygote transgenic ankyrin-B (+/−) animal that survives to adulthood, as well as cells derived from such animals that are deficient in 220 kDa ankyrin-B while retaining other alternatively spliced forms of the ankyrin-B gene. Advantageously, the transgenic animal is a rodent, such as a mouse. Such animals can be produced, for example, by homologous recombination as described (Scotland et al, J. Cell Biol. 143:1305–1308 (1998)). Adult 220 kDa ankyrin-B (+/−) animals of the invention have an impaired capacity for normal cellular localization and/or accumulation of IP3R, but not ryanodine receptors or the SR CaATPase. This defect is expressed in multiple tissues, including heart, pancreas, brain, and spleen. Furthermore, these animals experience cardiac conduction defects and abnormal glucose regulation. Moreover, adult ankyrin-B (+/−) animals are resistant to α-adrenergic-induced reduction in heart rate.

Agents identifiable using the above-described assay as being capable of modulating the association between 220 kDa ankyrin-B and IP3R can be further assayed for their ability to enhance or inhibit the activity of 220 kDa ankyrin-B in cellular localization and physiological function of IP3R. Transfection of ankyrin B(+/−) or (−/−) cardiomyocytes with GFP-tagged 220 kDa ankyrin-B restores normal localization of IP3R. Specific antagonists have reduced effect on 220 kDa ankyrin-B deficient cells but block 220 kDa ankyrin-B-dependent rescue of IP3 receptor localization in 220 kDa ankyrin-B (+/−) cardiomyocytes or other primary cultures of cells from 220 kDa ankyrin-B (+/−) and (−/−) animals (e.g., mice), and have reduced physiological effects on ankyrin-B (+/−) animals compared to (+/+) animals. Specific agonists, in contrast, either independently restore IP3 receptor localization and/or enhance 220 kDa ankyrin-B-dependent rescue of IP3 receptor localization in 220 kDa ankyrin-B (+/−) cardiomyocytes or other primary cultures of cells from ankyrin-B (+/−) and (−/−) animals, and have enhanced physiological effects on ankyrin-B (+/−) animals compared to (+/+) animals.

The invention encompasses agents identified or identifiable using the above-described assays. Such agents can include novel small molecules (e.g., organic compounds (for example, organic compounds less than about 500 Daltons)), and novel polypeptides, oligonucleotides, as well as novel natural products (preferably, in isolated form). One example of currently available drugs that can be expected to interact with the 220 kDa ankyrin-B-dependent pathway for IP3R sorting are sigma agonists and antagonists, which were originally believed to target opiate-related receptors but recently have been reported to interact with an ER receptor associated with 220 kDa ankyrin-B and IP3R (Hayashi and Su, Proc. Natl. Acad. Sci. USA 9:9 (2001)). Interestingly, sigma agonists enhance the response to bradykinin, a pain mediator, and modulate intracellular $Ca^{2+}$ levels (Hayashi et al, J. Pharmacol. Exp. Ther. 293:788–798 (2000)).

Agents of the invention can be formulated as pharmaceutical compositions comprising the agent(s) and a pharmaceutically acceptable diluent or carrier. The composition can be present in dosage unit form (e.g., as a tablet or capsule) or as a solution, preferably sterile, particularly when administration by injection is anticipated. The composition can also be present as a cream, gel or ointment, for example, when topical administration is preferred. The dose and dosage regimen will vary, for example, with the patient, the agent and the effect sought. Optimum doses and regimens can be determined readily by one skilled in the art.

Agents identified or identifiable using one or more of the above assays can be potentially used in the clinical management of Gαq-mediated processes including, but not restricted to, cardiac hypertrophy, insulin release from the endocrine pancreas (i.e., diabetes), memory disorders, impaired airway mucociliary clearance, platelet aggregation, impaired vision, disrupted endocrine balance and pain and inflammation resulting, for example, from bradykinin and tachykinin-based pathways. An important feature of the 220 kDa ankyrin-B-dependent IP3 receptor localization pathway is that it encompasses responses to multiple chemically diverse signals but is restricted to IP3R, and does not affect other sources of intracellular calcium. These features are a significant advantage in treatment of cardiac hypertrophy, for example, which can result from a variety of causes (elevated angiotensin II, endothelin, norepinephrine). Current therapies include calcium channel blockers, which affect multiple targets for calcium and thus have undesired side reactions, and angiotension converting enzyme inhibitors, which do not protect against other types of hypertrophy-promoting hormones.

The present invention further relates to methods of diagnosis based on the detection of mutations in 220 kDa ankyrin-B. Such mutations can be identified, for example, using single nucleotide polymorphisms. One candidate for disease due to 220 kDa ankyrin-B mutation is type 4 long QT syndrome, a dominantly-inherited a typical variant of long QT syndrome with the unusual feature of sinus bradycardia in addition to a prolonged QT interval. This cardiac arrhythmia causes sudden death in affected individuals, and maps to the same chromosomal region of 4q25–27 as the gene encoding ankyrin-B (Schott et al, Am. J. Hum. Genet. 57:1114–1122 (1995)). Moreover, 220 kDa ankyrin-B(+/−) mice have been shown to exhibit a significant increase in the rate-corrected QT interval (FIG. 6C), as well as bradycardia (FIG. 6A) (see Example 1). While this rescue assay may not be an ideal way to search for new mutations, it does provide a way to evaluate functional consequences of mutations that have been identified.

The invention additionally relates to kits, for example, kits suitable for conducting assays described herein. Such kits can include 220 kDa ankyrin-B, or binding domain thereof or fusion protein comprising same, and/or binding target (e.g., IP3 receptor or binding portion thereof), free or bound to a support. One or more of these components can bear a detectable label. The kit can include any of the above components disposed within one or more container means. The kit can further include ancillary reagents (e.g., buffers) for use in the assays.

The invention also relates to genetically engineered full-length chimeric human ankyrin-B/rodent (e.g., rat) ankyrin-G cDNA constructs and mutated human 220 kDa ankyrin-B cDNA constructs suitable for use, for example, in rescuing 220 kDa ankyrin-B deficiency in cultures of ankyrin-B (+/−) and (−/−) cells, including neonatal and adult cardiomyocytes, as well as for enhancing ankyrin-B expression in (+/+) cells. Examples of such constructs are described in the Examples that follow (note particularly Example 3).

The invention further relates to methods identifying 220 kDa ankyrin-B-interacting proteins and evaluating their role in cellular localization and function of IP3R. These methods include affinity columns using immobilized 220 kDa ankyrin-B to bind to proteins in tissue and cultured cell extracts, yeast two-hybrid screen, and expression library screens. Controls in the identification of 220 kDa ankyrin-B-interacting proteins included mutated forms of 220 kDa ankyrin-B that have specifically lost activity in rescue of IP3R targeting in 220 kDa ankyrin-B (+/−) and (−/−) cardiomyocytes.

Certain aspects of the invention can be described in greater detail in the non-limiting Examples that follows.

EXAMPLE 1

Cardiac Arrhythmia and Abnormal Glucose Regulation in Mice Heterozygous for Null Mutation in Ankyrin-B Experimental Procedures Cell Culture and Calcium Imaging. Neonatal myocytes were isolated and calcium imaging was performed as described (Tuvia et al, J. Cell Biol. 147:995–1008 (1999)). Briefly, calcium imaging in spontaneously contracting 5–6 day old myocytes was performed using fluo-3/AM (Molecular Probes). Cells were loaded with 10 μM fluo-3/AM for 30 minutes at 37° C. and washed Images were collected at 8 frames/sec and assembled using Adobe Premiere.

Immunofluorescence and Immunoblotting. Primary cultures and 8–10 μm tissue sections were analyzed using the following antibodies: insulin, glucagon, α-actinin, DHPR (Sigma), IP3R type I, II, III and a Pan antibody, RyR type II (RyR$_2$), SR/ER Ca$^{2+}$ATPase (SERCA2; Affinity Bioreagents) or AnkB. For islet area, sections were stained using H & E or a glucagon antibody to visualize the α-cells (Lee and Laychock, Biochem. Pharmacol. 61:327–336 (2001)). Islet area was determined by tracing the outline of the islet using available software (Carl Zeiss LSM, version 3.80). Immunoblotting was performed as described (Scotland et al, J. Cell Biol. 143:1305–1315 (1998)).

IP3 Binding Experiments. Cardiac membranes were prepared and labeled with increasing concentrations (5–40 nM) of [$^3$H] IP3 (Amersham) essentially as described (Perez et al, J. Biol. Chem. 272:23961 1997)). Assays were performed in triplicate, and at each IP3 concentration, non-specific binding was assessed in the presence of 1 μM unlabeled IP3 (ICN).

Northern Blots. Northern blots were performed as described previously (Scotland et al, J. Cell Biol. 143: 1305–1315 (1998)). $^{32}$P-dCTP-labeled asymmetric cDNA probes to detect IP3R type I, all IP3R types (pan) and GAPDH were designed against the available mouse sequences.

EKG recordings. EKG recordings were obtained using a radiotelemetry apparatus (DSI). Transmitters were implanted and the mice recovered for 5 days prior to recordings. EKG traces were analyzed using Data Quest analysis software 2.1 (DSI). P wave duration, PR interval, RR interval, QRS interval and QT interval were all calculated according to established methods. The rate corrected QT interval (QTc) was calculated from the relationship $QTc = QT/(RR)^{1/2}$ Following a 15-hour fast, blood glucose levels were measured (OneTouch Ultra; Lifescan) before and up to 120 min after an intraperitoneal injection of either PBS, glucose (2 g/kg) or insulin (5 units/kg; Eli Lilly) (Ludwig et al, J. Clin. Invest. 107:379–386 (2001)).

Statistics. Data were analyzed using either paired two-tailed t tests or two way ANOVA, and P values less than 0.05 were considered significant (*). Error bars in all figures represent the SEM.

Results

AnkB Expression is Limited by Gene Dosage

AnkB (−/−) mice generated by homologous recombination and homozygous for a null mutation die in the neonatal period with musculoskeletal defects, thymic atrophy, and degeneration of the optic nerve as well as other long axon tracts (Scotland et al, J. Cell Biol. 143:1305–1315 (1998); Tuvia et al, J. Cell Biol. 147:995–1008 (1999)). AnkB (+/−) mice back-crossed at least 5 generations into a C57Bl/6 background survive to adulthood, although with numerous gross abnormalities including severe kyphosis, indicative of musculoskeletal defects, cysts particularly in the anus, obesity, loss of hair (FIG. 1A), as well as exercise intolerance and early death by 10–12 months.

Figure 1B:
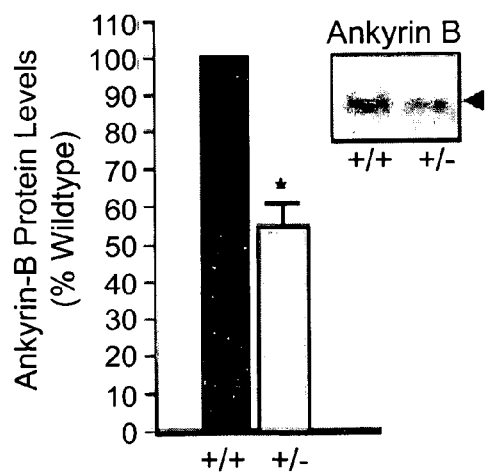
Figure 1C:
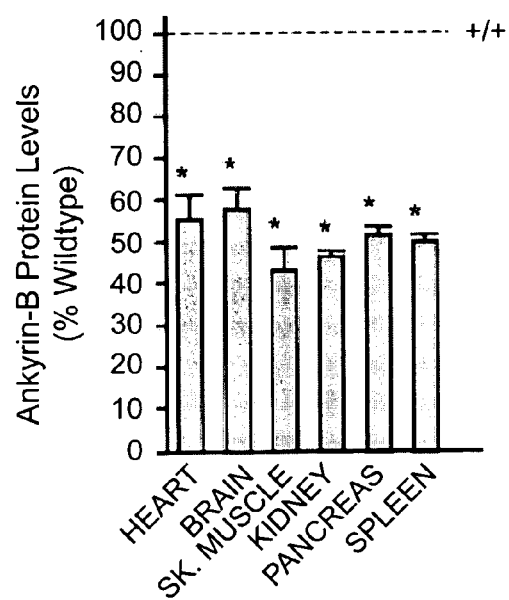

AnkB (+/−) mice exhibit ~50% deficiency of AnkB, as determined by quantitative immunoblot (FIG. 1B) and radioimmunoassay of cardiac tissue. AnkB levels are also reduced in brain, skeletal muscle, kidney, pancreas, and spleen (FIG. 1C). Thus, AnkB expression in multiple tissues is dependent on gene-dosage, and mice heterozygous for a null mutation exhibit haploinsufficiency.

Reduced Expression of IP3R in AnkB (+/−) Mice

Figure 2A:
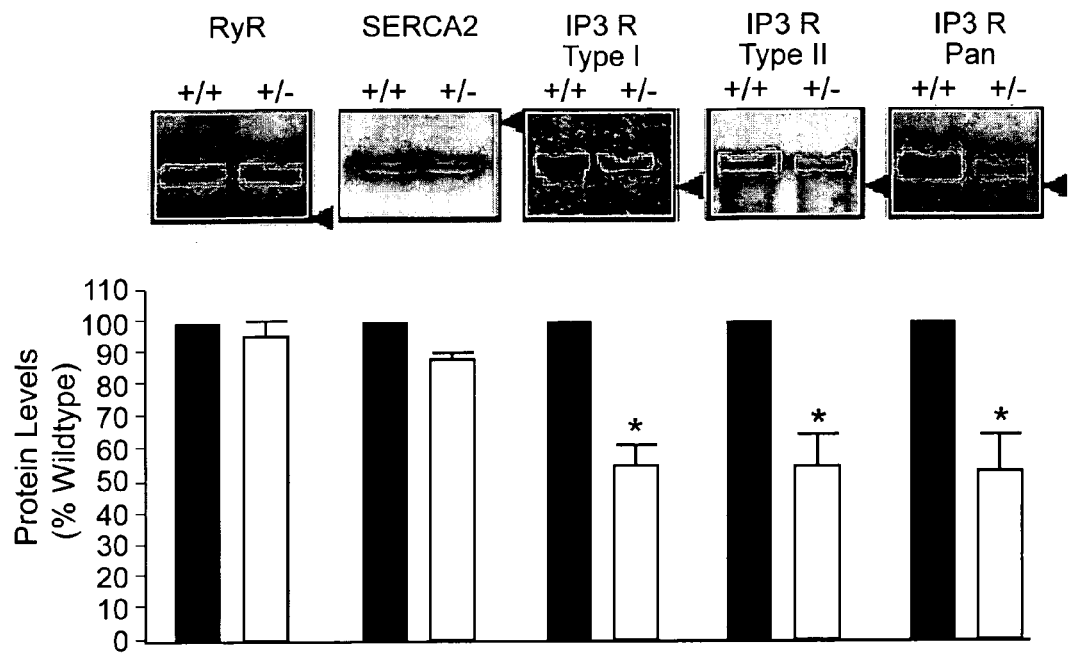
FIGS. 2A–2D. Decreased IP3 binding and downregulation of IP3R expression in AnkB (+/−) mice.
Figure 2B:
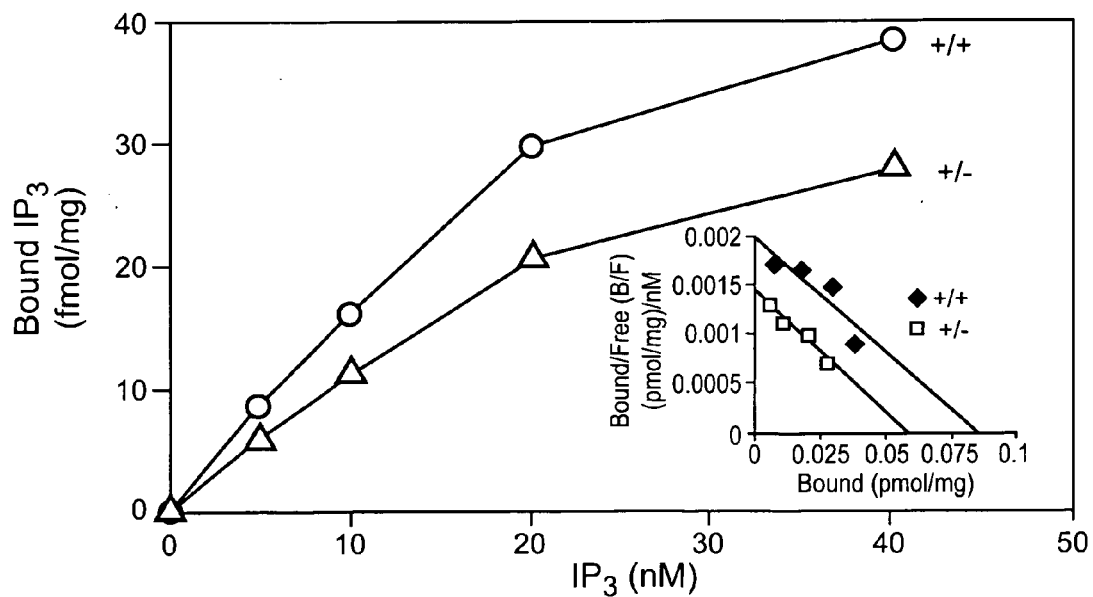
Figure 2C:
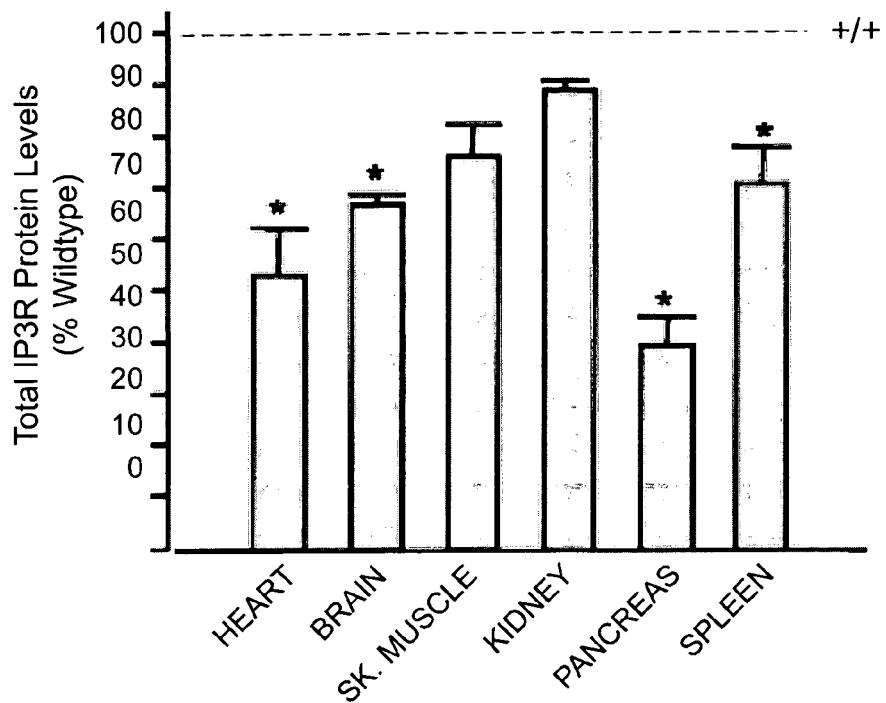
Figure 2D:
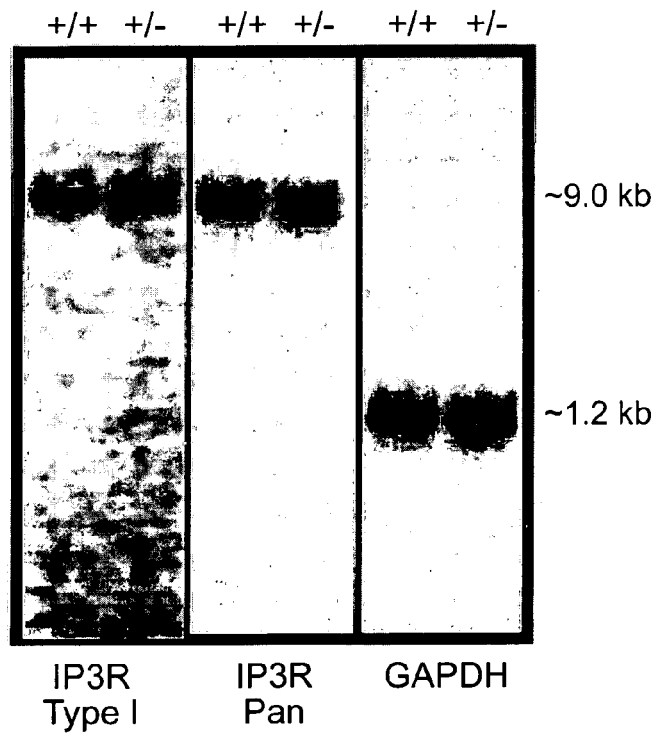

IP3R type I, II and total IP3R protein levels are reduced by ~50% in adult heart of AnkB (+/−) mice based on quantitative immunoblots, while $RyR_2$ and SERCA2 levels are unchanged (FIG. 2A). IP3 binding analyses were also performed since this method is independent of antibody specificity and IP3R subtype expression, and provides a direct estimation of IP3 affinity for the IP3R (FIG. 2B). These experiments reveal that in comparison to wildtype hearts, AnkB (+/−) cardiac muscle displays a significant reduction (33%, n=5) in IP3 binding capacity (FIG. 2B; +/+ $B_{max}$=0.083 pmol/mg; +/−=0.056 pmol/mg), while having similar $K_d$ values (+/+=24 nM; +/−=25 nM; n=5). Immunoblot analyses with a pan IP3R antibody revealed that total IP3R protein levels are also significantly lower in other tissues, including spleen, brain, and pancreas (FIG. 2C). The extent of reduction of total IP3R levels vary between tissues, with the greatest reduction occurring in pancreas (~60%) and the least in kidney (~10%; FIG. 2C). In these experiments, no additional protein bands in the immunoblots, indicative of cross-reactivity of degradation products, were observed. Finally, Northern analyses to detect IP3R mRNA levels were performed with asymmetric cDNA probes specific for Type I IP3R, or probes recognizing conserved sequence amongst all IP3R transcripts. These Northern blots reveal that IP3R type I mRNA levels, as well as total IP3R mRNA levels, are unchanged in (+/−) hearts (FIG. 2D). Consequently, it is concluded that the reduction of total IP3R protein levels observed in AnkB (+/−) cardiac tissue is a result of post-translational regulatory events.

Figure 3A:
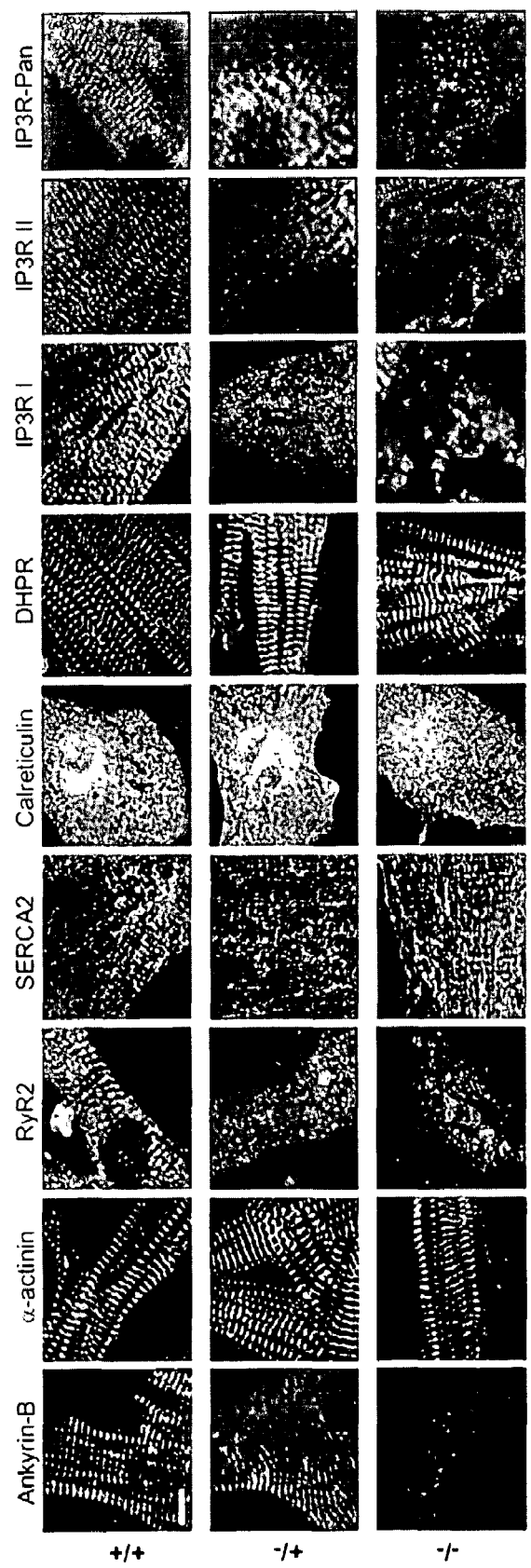
FIGS. 3A–3C. AnkB (+/−) neonatal cardiomyocytes display mis-localization of IP3R and RyR and aberrant $Ca^{2+}$-release/uptake mechanisms.
Figure 3B:
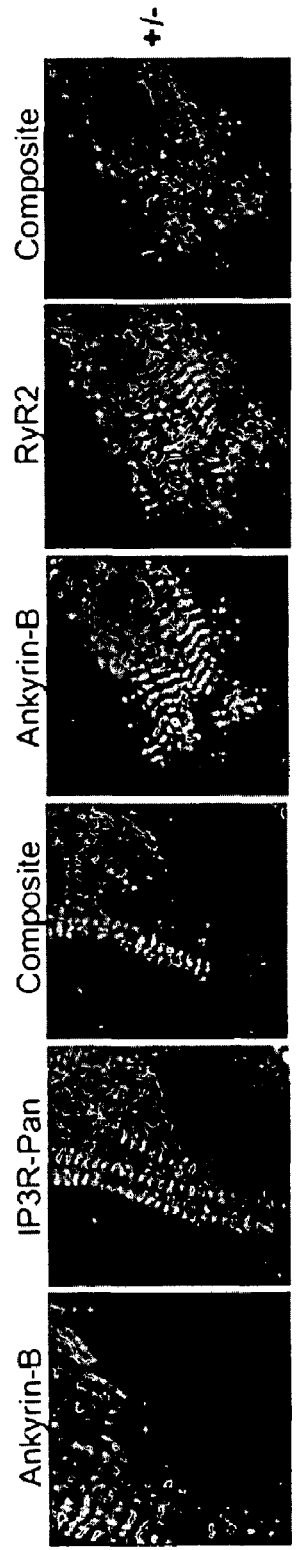

Mis-Localization of IP3R and RyR and Abnormal $Ca^{2+}$-Dynamics in Neonatal AnkB (+/−) Cardiomyocytes Next examined was the localization of AnkB, along with other structural and $Ca^{2+}$ homeostasis proteins in cultured cardiomyocytes isolated from (+/+), AnkB (+/−), and (−/−) neonatal mice. AnkB visualized by immunofluorescence is striated in (+/+) myocytes, and while the majority of AnkB staining is localized to the A band, a less intense AnkB signal is also detected at the Z line (FIG. 3A). This pattern of AnkB expression is completely absent in (−/−) myocytes. Myocytes derived from (+/−) mice display a striated pattern of AnkB only in restricted regions of these cells while AnkB is mis-localized in other regions (FIGS. 3A, 3B). This uneven pattern of AnkB localization pattern in (+/−) myocytes suggests that AnkB assembly is highly cooperative and requires a critical concentration of AnkB to achieve its normal striated localization. A consequence is that (+/−) myocytes are chimeras with respect to AnkB, with some regions showing a semi-normal pattern while other regions are lacking AnkB.

$RyR_2$ and IP3R type I, II as well as IP3Rs visualized by the 'pan-IP3R' antibody, are mis-localized in neonatal (−/−) cardiomyocytes and exhibit a punctate rather than striated distribution (FIG. 3A). Strikingly, $RyR_2$ and IP3Rs also display a similar punctate, non-striated pattern in most myocytes isolated from (+/−) neonatal mice (FIGS. 3A, 3B). Since both IP3R type I and II isoforms are mis-localized in (+/−) and null myocytes these results indicate that these IP3R family members use a common AnkB-dependent pathway for segregation in the ER/SR. It was also determined in numerous (+/−) cells that IP3R isoforms visualized with a pan IP3R antibody and $RyR_2$ display a normal pattern of expression in close proximity to regions with a striated AnkB distribution (FIG. 3B). These results indicate that AnkB organizes IP3R and RyR locally (i.e., within microns), since areas of (+/−) myocytes that present a normal striated pattern of AnkB also contain properly localized RyR and IP3R, while both proteins are mis-localized in regions lacking AnkB (FIGS. 3A, 3B). Second, the majority of AnkB labeling is clearly distinct from that of either IP3R or RyR, indicating that AnkB does not form 1:1 stoichiometric complexes with these proteins. Thus, a full complement of AnkB is required for normal localization of two distinct $Ca^{2+}$-release channels in the ER/SR of neonatal mice. In contrast to the disorganization of IP3R and RyR, markers for the intracellular cytoskeleton (α-actinin), ER/SR (SERCA2; calreticulin), and T-tubules (DHPR) all exhibit characteristic patterns in (+/−) and (−/−) cardiomyocytes that are indistinguishable from (+/+) cardiomyocytes (FIG. 3A). Previous observations that SERCA2 was mis-localized in AnkB (−/−) cardiomyocytes (Tuvia et al, J. Cell Biol. 147:995–1008 (1999)) were not reproduced in this study.

Figure 3C:
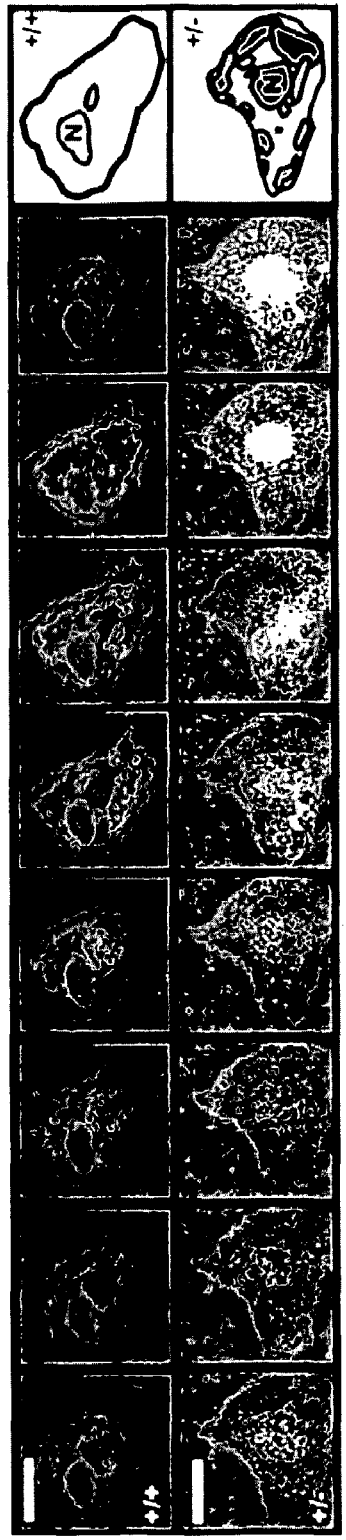

$Ca^{2+}$ dynamics were next visualized in spontaneously contracting (+/+) and (+/−) neonatal cardiomyocytes using fluo3/AM. Wildtype cardiomyocytes display organized rhythmic $Ca^{2+}$ release and concentric waves emanating from a single perinuclear region toward the cell periphery (FIG. 3C) (Jaconi et al, Mol. Biol. Cell 11:1845–1858 (2000)). In contrast, $Ca^{2+}$ dynamics in (+/−) myocytes are clearly disrupted (FIG. 3C). In these (+/−) cultures, numerous random foci of $Ca^{2+}$ release are observed (FIG. 3C), resulting in chaotic $Ca^{2+}$ waves spreading across the cell. Indeed, after a period of random $Ca^{2+}$ bursts, it was consistently observed that $Ca^{2+}$ levels reach maximal levels for 3–10 seconds (<1 sec in (+/+) cultures), during which time the cell quivers, until finally levels decrease. These abnormalities in $Ca^{2+}$-dynamics are accompanied by qualitative and quantitative differences in contractility. First, in comparison to (+/+) cultures, (+/−) myocytes have a lower frequency of spontaneous contraction (143±10 contractions/min vs. 78±7 contractions/min; p<0.05). Second, unlike (+/+) myocytes, which contract in a rhythmic fashion involving the entire cell, (+/−) myocytes consistently undergo repeated quivering cycles in peripheral regions of the cell before undergoing a whole cell contraction. Third, the rhythmic rate of contraction is irregular in (+/−) cultures, and many cells even cease beating for extended periods of time before eventually resuming contraction cycles.

Figure 4B:
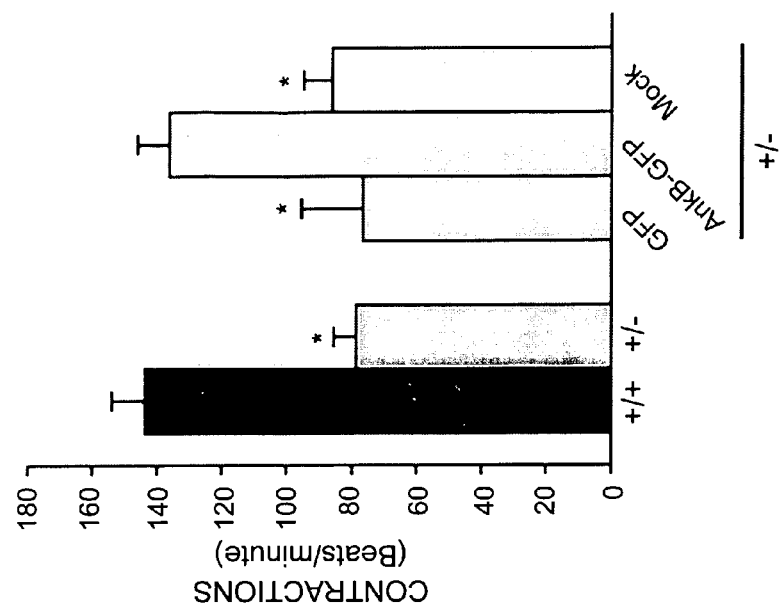
FIGS. 4A–4C. Rescue of ankB (+/−) cardiomyocytes with GFP 220 kDa ankB.
Figure 4A:
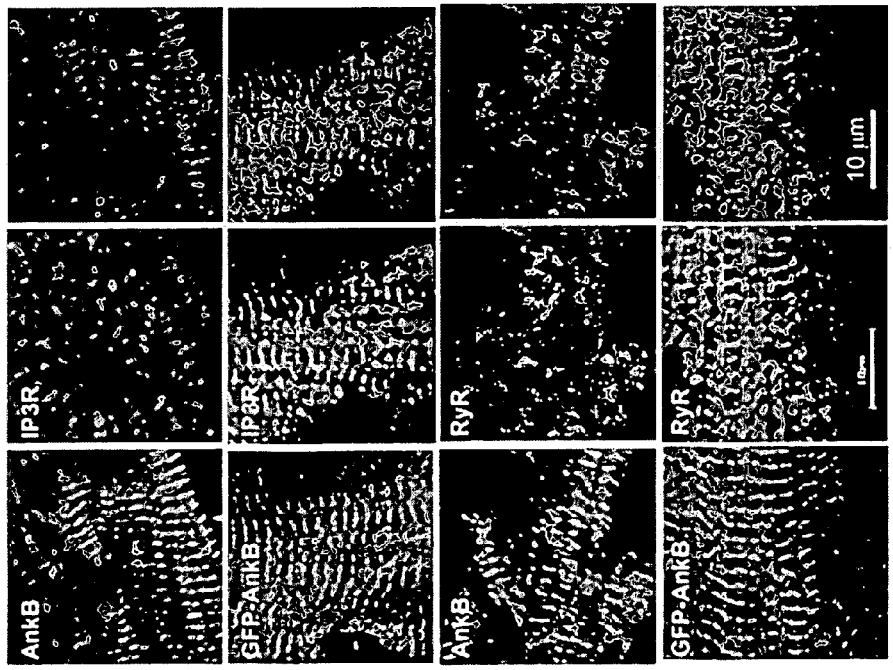
Figure 4C:
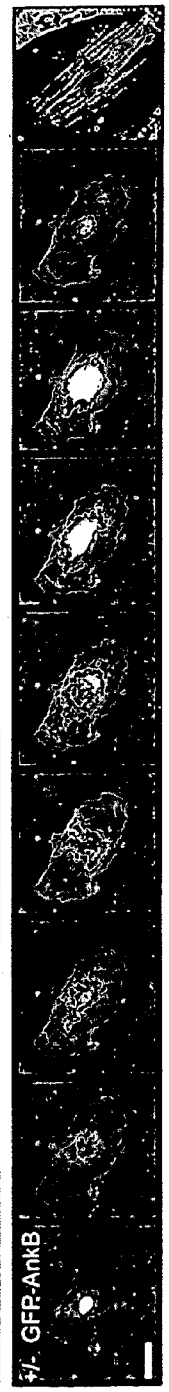

The defects in total IP3R and RyR2 localization, calcium-release/uptake, and contractility rates can be restored by transfection of (+/−) cardiomyocytes with a plasmid encoding GFP 220 kDa AnkB (FIGS. 4A–C). Restoration of 220 kDa AnkB also results in a normal distribution of IP3R visualized with a pan IP3R antibody and $RyR_2$ receptors in transfected (+/−) cardiomyocytes (FIG. 4A). To quantitatively assess the extent of restoration of calcium-release channel localization and function, the number of spontaneous contractions per minute were measured in the absence or presence of GFP 220 kDa AnkB. In these experiments, the contractions per minute were counted for at least 50 cardiomyocytes in a culture and analyzed between five and nine samples. Wildtype cultures spontaneously contract at 143±10 bpm while heterozygote cardiomyocytes contract at a much slower rate of 79±7 ($p<0.05$). AnkB transfected cells, subsequently identified by immunofluorescence with an antibody against GFP, beat at a rate of 137±10 contractions per minute, a value very similar to wildtype levels ($P>0.05$). By contrast, AnkB (+/−) cultures expressing GFP alone, or mock transfected exhibited the same contraction frequency as untransfected (+/−) cultures (FIG. 4B; $p>0.05$). Transfection of AnkB (+/−) cardiomyocytes with GFP 220 kDa AnkB rescued the defects in calcium-dynamics and restored $Ca^{2+}$ which are very similar to those observed in (+/+) cultures (FIG. 4C). $Ca^{2+}$-imaged heterozygotes were analyzed using GFP and α-actinin-specific antisera to confirm that the $Ca^{2+}$-rescued cells were transfected, (FIG. 4C, right). Taken together, these data clearly demonstrate that reduction of 220 kDa AnkB is directly responsible for abnormal $Ca^{2+}$-dynamics and contractile behavior of AnkB (+/−) cardiomyocytes.

Figure 5A:
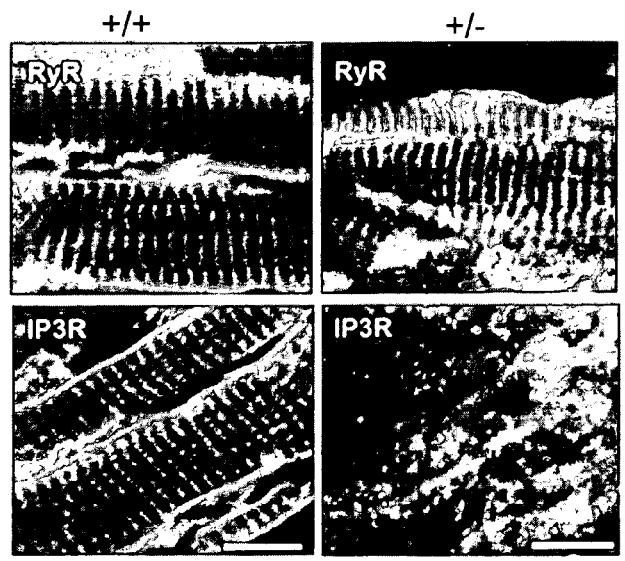
FIGS. 5A–5C. IP3R localization in adult ventricular muscle and Purkinje fibers.
Figure 5C:
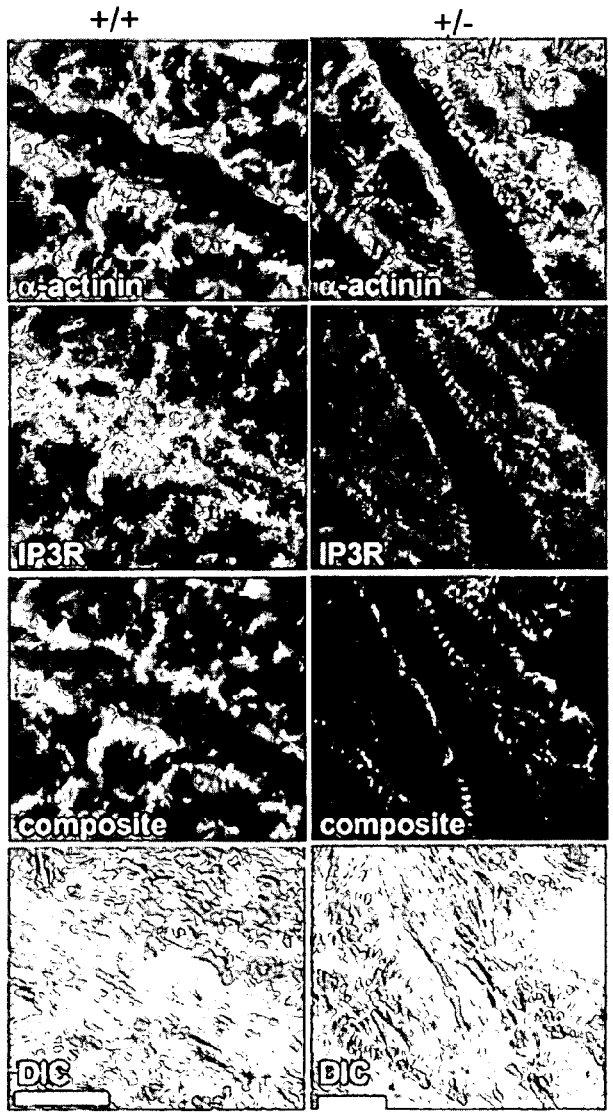

Mis-Localization and Reduced Levels of IP3R in Ventricular Myocytes and Purkinje Fibers of AnkB (+/−) Mice IP3R and RyR localization were evaluated in adult heart using sections of ventricular muscles (FIG. 5). Using antibodies to IP3R type I, it was determined that IP3R are consistently mis-localized in cultured myocytes and in sections of ventricular muscle obtained from adult AnkB (+/−) mice (FIG. 5A). Identical results were also observed with the IP3R pan antibody. These results are in precise agreement with those obtained in neonatal cultures (FIG. 3A). However, in sharp contrast to IP3R, $RyR_2$ localization is normal in ventricular sections of adult (+/−) mice compared to littermates (FIG. 3A). A normal localization of $RyR_2$ is also observed in cultured myocytes derived from adult mice. Together with the observation that protein levels of $RyR_2$ in adult heart tissue are unaffected (FIG. 2A), these results are consistent with the ability of the (+/−) mouse to survive to adulthood with relatively normal heart function, and indicate that $RyR_2$ sorting in adult mice is not sensitive to decreased AnkB concentrations. IP3Rs apparently cannot access such an alternative pathway, and require a critical concentration of AnkB for their expression and spatial organization in both neonatal and adult cardiac muscle.

Figure 5B:
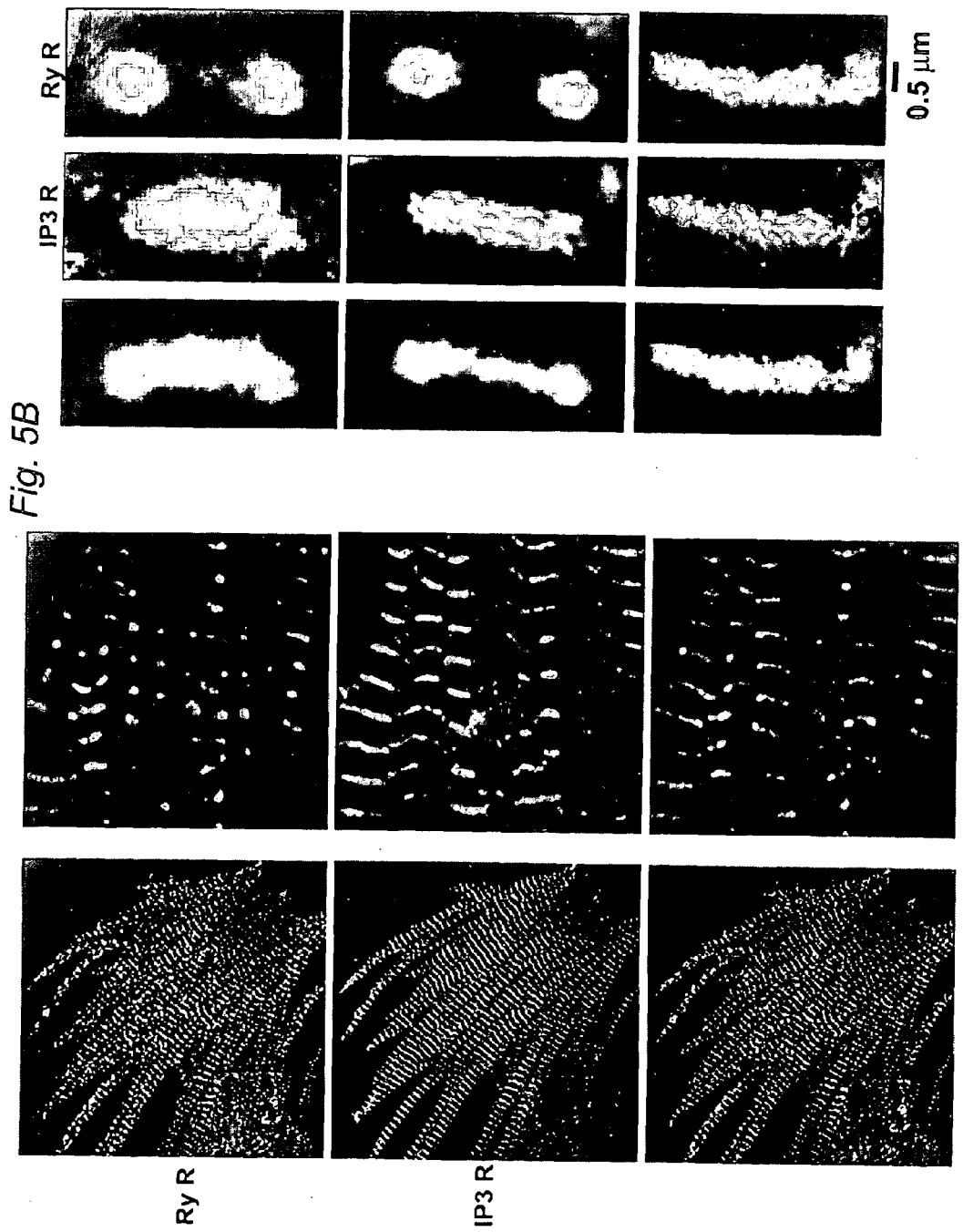

Since IP3R and RyR evidently utilize unique mechanisms for localization, there was interest in whether the two channels were, in fact, spatially segregated into distinct locations within cardiomyocytes. Previous reports have suggested that both channels are localized in a striated pattern along the T-tubule (Scriven et al, Biophys. J. 79:2682–2691 (2000); Tuvia et al, J. Cell Biol. 147:995–1008 (1999)). However, closer examination using high power confocal microscopy of wildtype neonatal cardiomyocytes co-labeled with antibodies against IP3R and RyR revealed that both receptors display a striated pattern but occupy distinct domains within the sarcomere (FIG. 5B). In fact, it is very difficult to visualize areas of overlap between these proteins, indicating that their distributions are complementary. These results are consistent with previous reports indicating that IP3R and RyR are targeted to distinct subcellular compartments within various types of cells (Walton et al, J. Cell Biol. 113:1145–1157 (1991); Martone et al, Brain Res. 756:9–21 (1997); Zhang et al, Biochem. J. 340:519–527 (1999)). The significantly disrupted pattern of IP3R labeling in ankyrin-B (+/−) adult heart is consistent with a central role for ankyrin-B in the creation of unique spatially-privileged $Ca^{2+}$ microdomains via IP3R localization.

Type I IP3Rs are also strongly expressed within the conducting Purkinje fibers of the heart (Gorza et al, J. Cell Biol. 121:345–353 (1993), Lipp et al, Curr. Biol. 10:939 (2000)). Therefore, there was interest in determining whether conduction fibers from AnkB (+/−) display defects in IP3R distribution and/or expression levels. As expected, all (+/+) Purkinje fibers are intensely labeled with IP3R type I antisera (FIG. 5C) (Gorza et al, J. Cell Biol. 121:345–353 (1993), Lipp et al, Curr. Biol. 10:939 (2000)). In contrast, IP3R staining is significantly reduced in (+/−) Purkinje fibers (FIG. 5B). In fact, the majority of (+/−) Purkinje fibers show decreased levels of IP3R expression in a heterogeneous pattern. Similarly, we observed that AnkB is expressed in Purkinje fibers of the (+/+) mouse. This staining pattern becomes disorganized in (+/−) fibers. These data demonstrate that AnkB plays an important role in the regulation of IP3R Type I expression in cardiac conduction fibers.

Cardiac Arrhythmia in AnkB (+/−) Mice

Figure 6A:
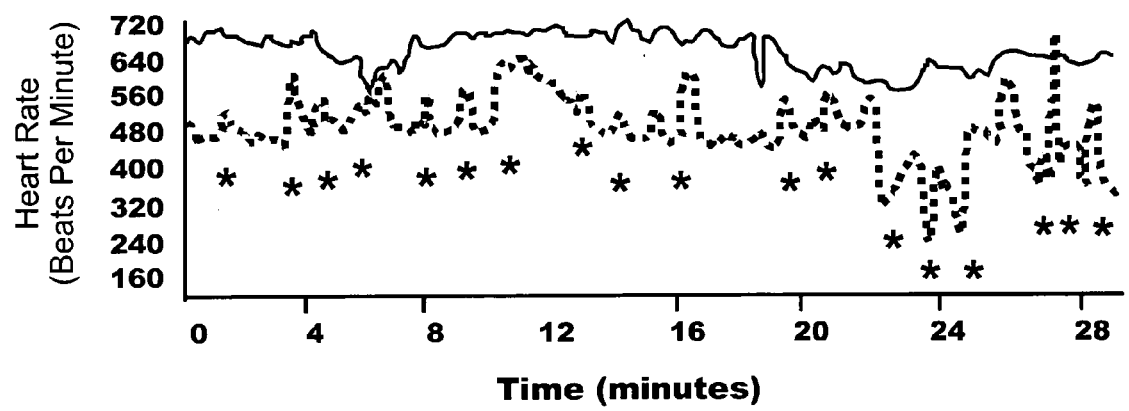
FIGS. 6A–6D. EKGs of AnkB (+/−) mice reveal sinus arrhythmia and defects in cardiac conduction.
Figure 6B:
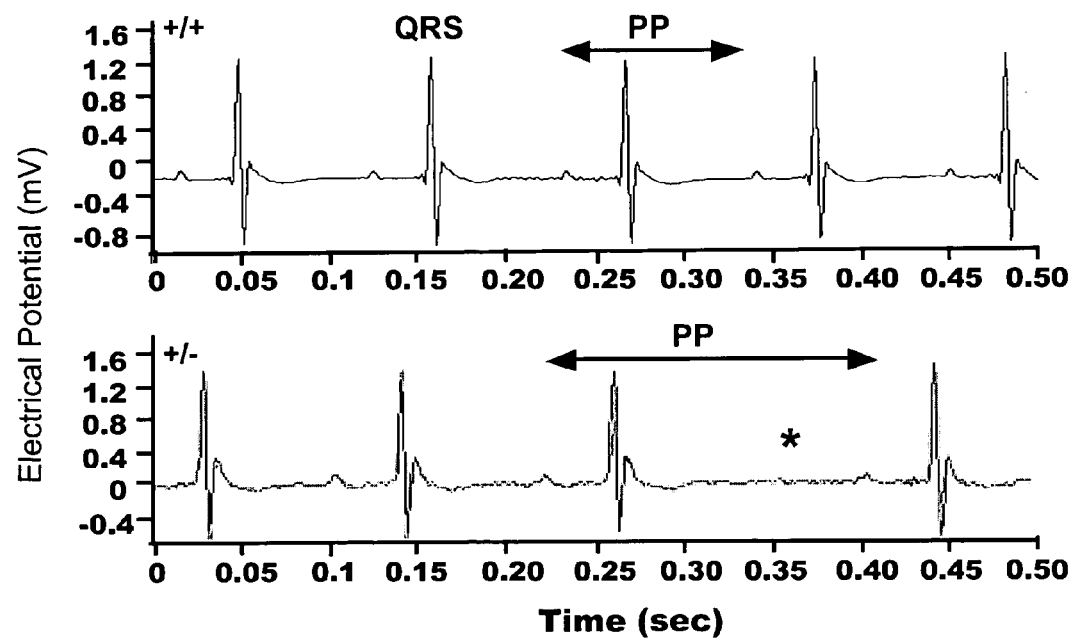

To understand the functional consequences of reduced levels of AnkB in adult heart, implanted radiotransmitters were used to record EKGs in ambulatory animals. AnkB (+/−) mice have a significant bradycardia, with a mean resting heart rate of 553±20 bpm compared to wildtype mice with heart rate of 610±14 bpm (FIG. 6A; $p<0.05$). AnkB (+/−) mice also exhibit a high degree of heart rate variability due primarily to multiple episodes of marked sinus arrhythmia, characterized by widened PP intervals (FIG. 6A). A representative example of sinus arrhythmia is shown in the EKG tracing (FIG. 6B).

Figure 6C:
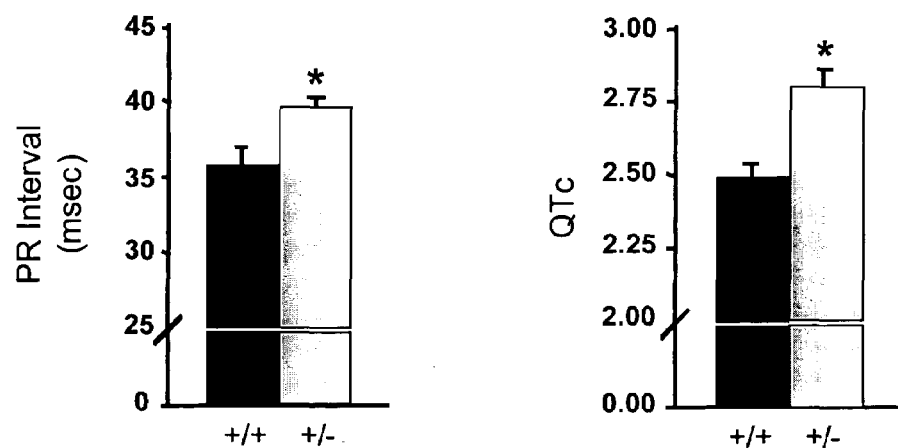

EKGs of (+/−) mice also reveal generalized conduction defects, including prolonged P wave duration and PR interval (conduction time from SA to AV node). P wave duration is significantly extended from 8.5±0.7 msec in wildtype mice to 13.4±0.5 msec in (+/−) mice ($p<0.05$), while PR intervals are significantly increased from 35.9±1.0 msec to 39.6±0.7 msec, respectively (FIG. 6C, $p<0.05$). For these recordings, PR intervals in (+/−) were measured under conditions where isorhythmic atrioventricular (AV) dissociation did not occur. Moreover, the duration of the QRS complex (measure of conduction from the AV node through the His-Purkinje system to the ventricle) is prolonged from 5.6±0.1 msec in (+/+) mice to 7.2±0.2 msec in AnkB (+/−) mice ($p<0.05$). The extent of prolongation of P wave duration, PR interval, and QRS complex duration are consistent with previous reports examining cardiac conduction defects in mice (Verheule et al, J. Cardiovasc. Electrophysiol. 10:1380 (1999)).

Figure 6D:
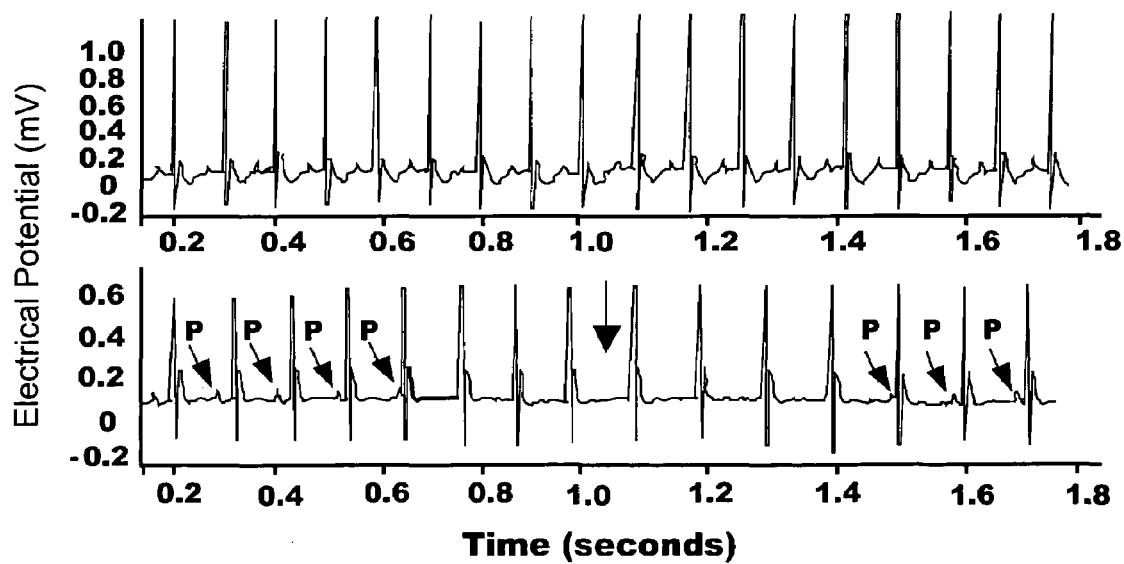

In addition to generalized conduction defects and bradycardia, ankyrin (+/−) mice also display a prolonged rate-corrected QT interval (FIGS. 6C, 6D). The QT interval, an indicator of ventricular systole, was increased from 2.50 +0.03 units in (+/+) mice to 2.77±0.06 units in AnkB (+/−) mice (p<0.05; FIG. 6C). These results are consistent with a previous mouse model of long QT syndrome (Drici et al, Circ. Res. 83:95 (1998)).

AnkB (+/−) mice exhibit episodes of intermittent isorhythmic AV dissociation during which the PP interval is longer than the RR interval (FIG. 6D). Generally, AV dissociation is indicative of loss of normal conduction between the AV node and the His-Purkinje system, and occurs when the ventricle depolarizes independent of the incoming P wave from the atrium. As visualized on the EKG (FIG. 6D), the slower atrial rate gives the appearance that the P wave has merged with the QRS complex; thereafter, the two complexes are fused. A spontaneous slowing of the ventricular rate (denoted by arrow) causes the reappearance of the P wave at the end of the tracing (FIG. 6D). In contrast, conduction abnormalities in (+/+) mice under similar conditions were not observed (FIG. 6D).

EKG abnormalities in (+/−) mice are observed by two months of age, and do not show obvious progression with age (not shown). Moreover, trichrome- and hematoxylin and eosin (H&E)-stained sections of heart tissue of AnkB (+/−) mice do not reveal obvious fibrosis or inflammation (not shown). Consequently, the defects in conduction are most likely due to intrinsic differences in AnkB (+/−) heart and are not secondary consequences of aging or degenerative changes.

AnkB (+/−) Mice Have Abnormal Regulation of Blood Glucose

The reduction in pancreatic total IP3R levels (FIG. 2C) and the dependence of the endocrine pancreas for IP3-regulated $Ca^{2+}$-release for normal insulin secretion (Biden et al, Biochem. J. 223:467 (1984), Wollheim et al, J. Cardiovasc. Pharmacol. 8:S65–70 (1986)) suggested the possibility of pancreatic dysfunction in AnkB (+/−) mice. AnkB is highly enriched in islets of Langerhans of (+/+) mice and is expressed in both α- (glucagon-secreting) and β-cells (insulin-secreting; FIG. 7A). Islets express IP3R type I and III by immunostaining (FIG. 7A) and by immunoblot (Lee and Laychock, Biochem. Pharmacol. 61:327–336 (2001)). In contrast, fluorescence of islets and immunoblots of whole pancreas reveal low levels of IP3R type II. Consistent with the immunoblot data (FIG. 2C), (+/−) mice display reduced AnkB staining in pancreas (FIG. 7B). Indeed, the lower levels of AnkB staining largely appear to be the result of a reduction of AnkB expression in islets (FIG. 7B). It was also determined that (+/−) pancreatic tissue consistently shows diffuse and low levels of IP3R (both type I and III), which are no longer enriched within islets (FIG. 7B). A surprising but consistent finding was that the insulin content in the islets, as assessed by immunofluorescence is significantly reduced in (+/−) mice (FIG. 7B).

Figure 7C:
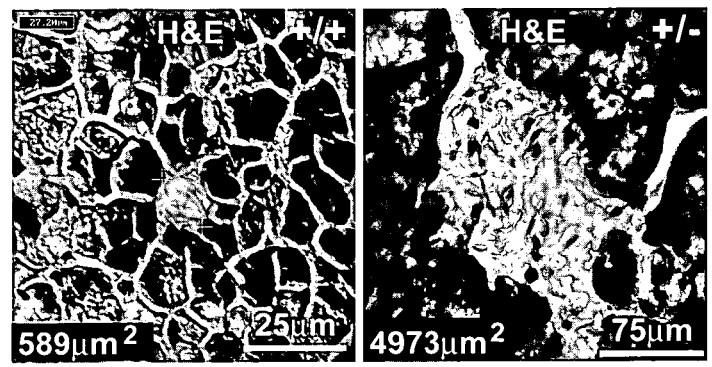
Figure 7C:
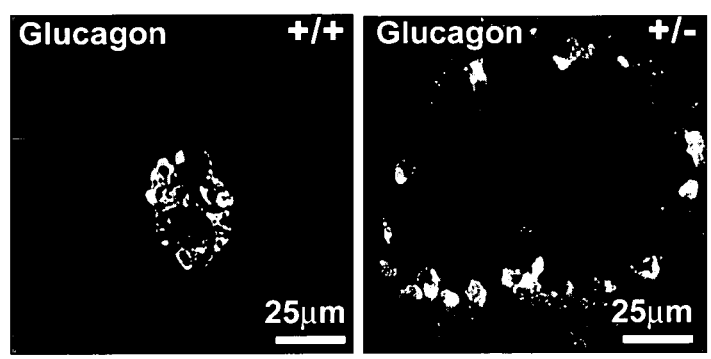
Figure 7D:
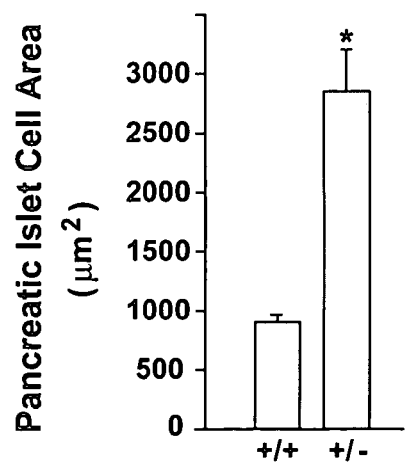

AnkB (+/−) mice exhibit significant hypertrophy of pancreatic islets visualized by H&E staining and fluorescence with a glucagon antibody (FIG. 7C). Using both methods, pancreatic tissue from (+/−) mice display significant enlargement of islets (FIGS. 7C, 7D), with an increase in cross-sectional area from 901±68 $\mu m^2$ in the (+/+) to 2857±340 $\mu m^2$ in the (+/−) pancreas (p<0.05).

Figure 8A:
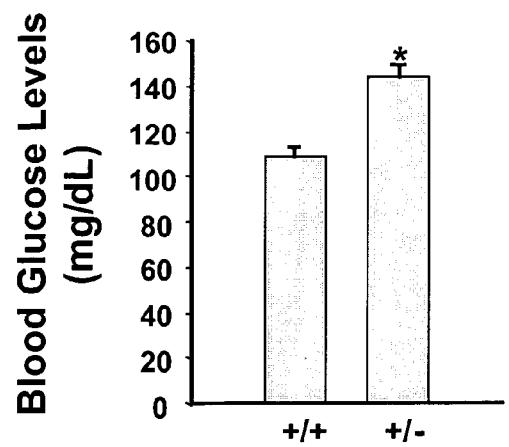
FIGS. 8A–8C. AnkB (+/−) mice display abnormalities in glucose homeostasis.
Figure 8B:
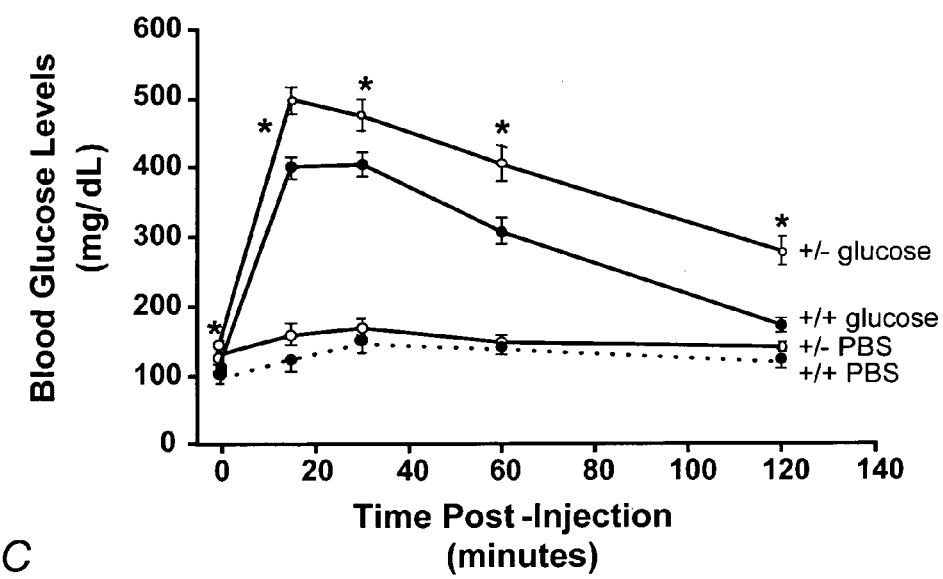

It was next determined if AnkB (+/−) animals displayed abnormal regulation of blood glucose levels. First, fasting blood glucose levels of (+/+) and (+/−) mice were compared and it was observed that (+/−) mice consistently display elevated levels of glucose ~30% greater than (+/+) mice (FIG. 8A). A glucose-tolerance test was performed to evaluate the ability of these mice to respond to elevated blood glucose. Fasted (+/+) and (+/−) mice were injected with glucose (2 g/kg body mass) (Ludwig et al, J. Clin. Invest. 107:379–386 (2001)) or saline, and blood glucose concentrations were monitored over two hours (FIG. 8B). Wildtype mice display a normal glucose tolerance curve (Ludwig et al, J. Clin. Invest. 107:379–386 (2001)), while (+/−) mice display slower insulin-response kinetics and their blood glucose levels fail to return to basal levels over the course of two hours. Thus, (+/−) mice display elevated glucose levels and respond inappropriately to a glucose challenge.

Figure 8C:
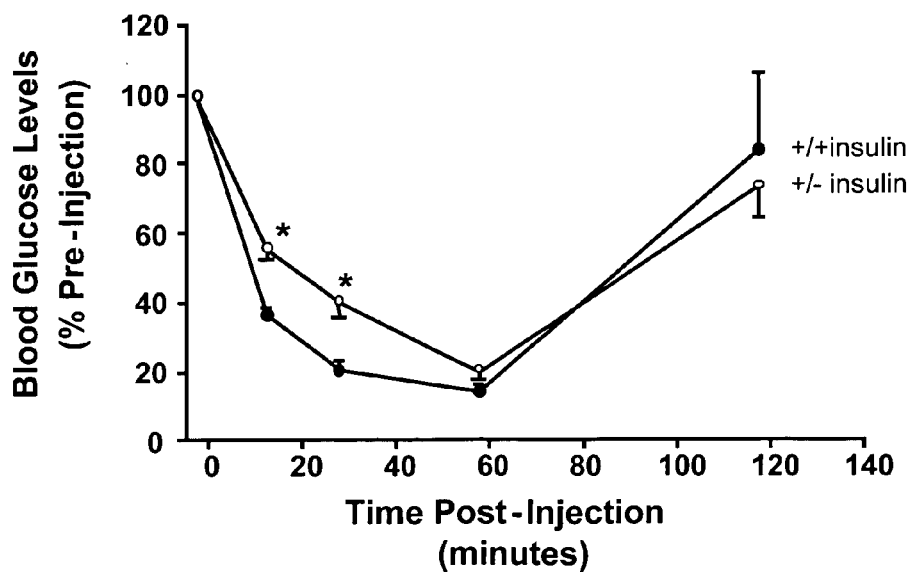

Finally, an insulin-tolerance test was performed to determine whether AnkB mice are insulin-resistant. Wildtype and (+/−) mice were injected with saline or insulin, and blood glucose levels were monitored for 120 min. Blood glucose levels in the (+/+) animals decline following the insulin injection and return to near normal levels by the end of the 120 min period (FIG. 8C). Heterozygotes also display a significant reduction in blood glucose levels following insulin injection, indicating that they retain their sensitivity to insulin (FIG. 8C). However, the kinetics of the insulin response are significantly different in (+/−) mice, suggesting that the AnkB (+/−) mice display abnormalities in insulin response.

This study establishes that partial AnkB expression is a dominantly inherited trait in mice heterozygous for an AnkB null mutation and addresses consequences of AnkB deficiency from a cellular level to the whole animal. AnkB (+/−) mice have a deficiency of AnkB associated with mis-localization of IP3R in adult ventricular myocytes, and reduced expression of IP3R in heart, pancreas, spleen, and brain. $RyR_2$, in contrast to IP3R, are normal in localization and in levels in heart tissue of adult (+/−) mice, although $RyR_2$ are mis-localized in neonatal (+/−) cardiomyocytes. AnkB deficiency in neonatal cardiomyocytes results in major disturbances in $Ca^{2+}$-dynamics and contractility that can be rescued by transfection with a plasmid encoding GFP 220 kD ankyrin-B. An explanation for the surprisingly severe consequences of reduced AnkB expression is provided by observations in cultured neonatal (+/−) myocytes of a chimeric pattern with regions of normal organization of AnkB and $Ca^{2+}$-release channels, and other regions in the same cell where AnkB as well as $RyR_2$ and IP3R are disorganized. This study also characterizes physiological abnormalities in AnkB (+/−) mice that include a cardiac arrhythmia characterized by irregular heart beat, sinus bradycardia, delayed cardiac conduction and prolonged QT interval, as well as pancreatic islet hypertrophy, elevated blood glucose and abnormal glucose tolerance.

The fact that IP3R are mis-localized and downregulated in tissues of AnkB mice indicate the possibility that physiological abnormalities observed in these mice are related to abnormal IP3R function. However, a direct connection between the AnkB (+/−) phenotype and IP3-related signaling is unclear due to several uncertainties in the literature. For example, one of the major limiting factors in addressing a role for IP3R in cardiac function is that there is no viable adult animal model which lacks multiple IP3R isoforms in which to study the direct effect of IP3R loss. Furthermore, the study of IP3R-dependent calcium-release in the heart has been difficult due to the overwhelming abundance of RyR (Jaconi et al, Mol. Biol. Cell 11:1845–1858 (2000)). Nonetheless, in isolated rat cardiomyocytes, IP3-induced signaling has been shown to lead to changes in calcium spiking and action potential firing. IP3R activation via microinjection of caged IP3 was shown to lead to a decreased frequency and amplitude of calcium spikes and a modest decrease in action potential firing rate (Jaconi et al, Mol. Biol. Cell 11:1845–1858 (2000)). Thus, according to this study, loss of IP3R signaling in the whole heart should lead to an increase in heart rate. IP3R expression and localization is clearly developmentally regulated in mouse cardiomyocytes and during cardiac development (Gorza et al, J. Mol. Cell Cardiol. 29:1023 (1997)). It is therefore possible that the cardiomyocytes used in that study may not have been fully differentiated since IP3R localization was present in a perinuclear distribution but not yet fully striated (Jaconi et al, Mol. Biol. Cell 11:1845–1858 (2000)). In a conflicting report, Lipp et al., show that quiescent or electrically paced rat atrial cells treated with a membrane-permeant IP3 ester, but not an inactive isomer, exhibit increased frequency of spontaneous calcium sparks as well as increasing the amplitude of action potential-evoked calcium transients (Lipp et al, Curr. Biol. 10:939 (2000)). Thus, these data suggest that IP3R act to increase cardiac automaticity and that IP3 receptor loss may lead to bradycardia, consistent with the loss of IP3R and bradycardia observed in AnkB (+/−) mice.

Further complicating issues in elucidating a role for IP3R in cardiac cells are several different observations regarding IP3R subtypes in cardiac tissue. For example, using cultured rat and ferret ventricular cardiomyocytes, Perez et al. determined by immunoblots, RT-PCR and RNase protection assays that type II is the predominant IP3R isoform, with no type I expressed (Perez et al, J. Biol. Chem. 272:23961 1997)). However, in a separate study, immunoprecipitation assays using rat cardiomyocyte lysates, show abundant IP3R type I-expression with very little IP3R type II (Jaconi et al, Mol. Biol. Cell 11:1845–1858 (2000)). In still another study, RT-PCR and immunoblot assays indicated that type II is the predominant isoform in rat ventricular cardiomyocytes with ~5–10% of total IP3R levels consisting of Type I; while equivalent levels of Type I and II are present in intact adult cardiac muscle (Lipp et al, Curr. Biol. 10:939 (2000)). Altogether, it appears that in rat ventricular cardiomyocytes both IP3R type I and type II are present, although type II is the more abundant. In the immunofluorescence experiments, it was possible to detect both IP3R type I and II in cultured mouse neonatal ventricular cardiomyocytes. However, regardless of IP3R subtype, it was determined that both the type I and II IP3R are mis-localized in cultured mouse ventricular cardiomyocytes, and total IP3Rs levels are downregulated in AnkB (+/−) cardiac muscle.

Altered IP3R expression in AnkB (+/−) mice may have additional consequences beyond the loss of IP3-dependent signaling. IP3R have been reported to bind to and affect other calcium binding/release proteins and these proteins could be affected by IP3R mis-localization and/or reduced expression. In particular, IP3R-interacting protein complexes have been identified to include: the store-operated calcium (SOC) channel (Kiselyov et al, Nature 396:478–82 (1998); Kiselyov et al, Mol Cell. 4:423–9 (1999)); an IP3R-associated cGMP kinase substrate (IRAG) and cGMP kinase I (Schlossmann et al, Nature 404:197–201 (2000)); the FK-506 binding protein (FKBP-12) and calcineurin (Cameron et al, Cell 83:463–72 (1995); Cameron et al, J. Biol. Chem. 272:27582–8 (1997)); as well as sigma receptors (Hayashi et al, Proc Natl Acad Sci USA. 98:491–496 (2001)). Furthermore, IP3R function may indirectly regulate other membrane conductances, as has been shown for the Na/Ca exchanger (Gilbert et al, Circ Res. 69:1632–9 (1991)). As a result, the loss of IP3R levels and localization may affect these molecules within the cardiomyocyte, and could potentially affect calcium dynamics via an indirect effect on one/all of these molecules.

A further potential complication in interpretation of AnkB-dependent physiology is that AnkB mice may have altered expression of protein(s) in addition to IP3R. A detailed characterization, perhaps involving DNA arrays or proteomics may prove useful in identifying other proteins involved in the generation of the AnkB phenotype. It must be noted, however, that gene-chips may prove of limited use, since in the experiments IP3R mRNA levels were unaffected and therefore, would not have been identified.

Several phenotypic features of the AnkB (+/−) mouse suggest that they possess a complex endocrinopathy involving more than a simple Type I diabetes. For instance, AnkB (+/−) mice are hyperglycemic and show reduced insulin in the pancreas, but also display obesity and a slower response to a glucose challenge indicating some form of insulin-resistance. Multiple systems that regulate endocrine function are known to depend on IP3R signaling including the pancreas, adrenal gland (Shelat et al, J Endocrinol. 162: 381–91 (1999)), and pituitary gland (Ortmann et al, Hum Reprod. 14 Suppl 1:194–206 (1999)), and therefore, could be adversely affected by the loss of AnkB. A detailed characterization of these systems will determine the relative role of AnkB in glucose regulation. A role of ankyrin-B in sorting IP3R to their normal location in the apical region of pancreatic beta cells could not be directly evaluated due to the small size of these cells and the low amounts of IP3R. However, an ankyrin-B-dependent targeting of IP3R seems likely by analogy with the clear loss of targeting of IP3R in ankyrin-B (+/−) cardiomyocytes.

The requirement of AnkB for IP3R expression is not universal in all tissues, since the immunoblot data revealed that IP3R levels are not downregulated in every (+/−) tissue, unlike AnkB levels which were reduced ~50% in all tissues. One tissue that may not require ankyrin for expression of IP3R is vascular smooth muscle in the kidney, since IP3R levels in the kidney are only reduced ~10% in AnkB (+/−) mice. In kidney, IP3R are primarily localized in glomeruli and other vascular sites while AnkB is present in apical regions of proximal convoluted tubules (unpublished observations). Thus, AnkB may interact with IP3R in the epithelial cells of polarized tubules, but is unlikely to collaborate in the vascular sites in the kidney, or elsewhere in the body.

Disruption of tightly organized $Ca^{2+}$-release mechanisms due to loss of IP3R localization in ankyrin-B heterozygote mice have implications for signaling mechanisms related to intracellular $Ca^{2+}$ stores in the ER and in mitochondria, which can be important in processes including, for example, memory, exocytosis, ion channel regulation, and apoptosis (Clapham, Cell 80:259–68 (1995)). This point becomes critically relevant when considering the extremely restricted effective diffusion range of $Ca^{2+}$ due to reuptake and cytosolic buffering mechanisms (a range ~0.1 µm) (Allbritton et al, Science 258:1812–5 (1992)). Further, the close proximity of the ER/SR to the plasma membrane (<10 nm) appears to be critical for the IP3R-dependent activation of capacitative $Ca^{2+}$ entry via activation of store-operated $Ca^{2+}$ channels (SOCs) as well as human TRP3 activation (Ma et al, Science 287:1647–51 (2000)). It is believed that the large cytosolic $NH_2$-terminus of the IP3R is capable of spanning the distance between the ER and the plasma membrane to coordinate signaling between the two membranes (Berridge et al, Science 287:1604–5 (2000)). Thus, in addition to regulating $Ca^{2+}$-release from the ER/SR, IP3R organization is necessary for the maintenance of coupling between ER/SR $Ca^{2+}$ emptying and activation of SOC refilling of depleted intracellular stores (Berridge et al, Science 287:1604–5 (2000)). Additionally, mitochondria have elaborate mechanisms for sensing and buffering elevated levels of cytosolic $Ca^{2+}$ (Jaconi et al, Mol. Biol. Cell 11:1845–1858 (2000)). Mitochondria buffer elevated $Ca^{2+}$ levels that exist in concentrated areas of $Ca^{2+}$-release sites (i.e. near IP3Rs) (Hajnoczky et al, Cell. 82:415–24 (1995); Collins et al, J. Biol. Chem. 276:26411–20 (2001)). Therefore, any disruption in IP3R spatial organization is likely to lead to ankyrin-B heterozygote mice possessing defects in coordinated $Ca^{2+}$ flux from IP3R into ER and mitochondrial intracellular stores.

The cellular mechanism by which AnkB coordinates proper IP3R expression and localization is unknown. However, a working hypothesis is that AnkB transiently interacts with IP3R and functions as a cellular chaperone for IP3R. The results showing that IP3R protein levels are reduced while mRNA levels are not changed in the (+/−) heart are consistent with this hypothesis For example, AnkB may interact with and inhibit IP3R following initial synthesis, and could participate in IP3R delivery to specialized domains in the smooth ER. In the absence of AnkB, IP3R would either be mis-sorted and/or inappropriately active leading to its degradation by a previously characterized ubiquitin-directed degradation pathway activated in response to excessive agonist activation (Oberdorf et al, Biochem J. 339:453–61 (1999)). An example of a cellular chaperone that maintains normal protein levels of its client is the membrane adaptor protein rapsyn, which is required for metabolic stabilization of acetylcholine receptors (Wang et al, J. Neurosci. 19:1998–2007 (1999)).

Evidence that ankyrin can directly interact with IP3R includes co-immunoprecipitation of these proteins from extracts of native brain tissue and cultured neuronal cells (Hayashi et al, Proc Natl Acad Sci USA 98:491–496 (2001); Joseph et al, J. Biol. Chem. 268:6477–86 (1993)). Moreover, ankyrin can compete for IP3 binding to the IP3R and block $Ca^{2+}$-release (Bourguignon et al, Cell. Biol. Int. 17:751–8 (1993)). A direct association between ankyrin and IP3R as well as possible interaction sites between ankyrin and IP3R remain to be established. One study has proposed that ankyrin associates with IP3R at a site selected based on limited sequence similarity to an AnkB-binding region in another protein (Bourguignon et al, J. Biol. Chem. 270: 7257–60 (1995)). It is now known that this site is located on the lumenal side of the ER and thus is not physiologically relevant. Nonetheless, since the three major isoforms of IP3R (type I to III) are all mis-sorted in AnkB (+/−) and null mice, these results indicate that interactions with AnkB are a conserved feature of this receptor family.

The normal localization of RyR in the heart tissue of adult AnkB (+/−) mice is consistent with the ability of these mice to survive with relatively normal heart function. The developmental timing of the AnkB-independent pathway for RyR targeting in the heart and presumably in skeletal muscle remains to be evaluated, but could occur at different stages depending on the type of muscle.

The results of this study, combined with findings of myopathy, axonal degeneration, and thymic atrophy in ankyrin-B (−/−) mice (Scotland et al, J. Cell Biol. 143: 1305–1315 (1998); Tuvia et al, J. Cell Biol. 147:995–1008 (1999)), establish the principle that ankyrin-B mutations can have dominant expression and potentially affect multiple organs, including the heart, skeletal muscle, nervous system, immune system, and pancreas as well as other endocrine systems. The coexistence of abnormal regulation of blood glucose with cardiovascular disease, immune dysfunction, peripheral neuropathy, and other endocrinopathies is well established. Occasionally, however, patients' clinical findings do not correlate with the severity of their disease. For example, the presence of congestive heart failure in diabetic patients who lack significant coronary artery disease is often attributed to microvascular disease. The findings raise the possibility that some of these patients may have unrecognized mutations in ankyrin-B as a cause of multiple organ system dysfunction. These considerations further indicate that ankyrin-B mutations, even if initially subtle, could result in mutually reinforcing pathology resulting in a significantly lowered life expectancy. For example, serious disease could be anticipated if an initially mild diabetes as described for ankyrin-B (+/−) mice were combined with other consequences of ankyrin-B deficiency including defective cardiac conduction, compromised immune response, peripheral neuropathy, and obesity due to disordered endocrine balance. Patients with clinically relevant mutations in ankyrin-B can be diagnosed through the use of single nucleotide polymorphisms.

The 220 kDa ankyrin-B-dependent pathway for IP3R sorting offers novel therapeutic targets with the potential for more specificity than can be obtained by interfering with $G_q$-related signaling or IP3 metabolism. One example of currently available drugs that can interact with this pathway are sigma agonists and antagonists, which were originally believed to target opiate-related receptors but recently have been reported to interact with an ER receptor associated with ankyrin-B and IP3R (Hayashi et al, Proc Natl Acad Sci USA 98:491–496 (2001)). Interestingly, sigma agonists enhance the response to bradykinin, a pain mediator, and modulate intracellular $Ca^{2+}$ levels (Hayashi et al, J. Pharmacol. Exp. Ther. 293:788–98 (2000)). Situations in which modulation of ankyrin-B/IP3R pathway can be expected to be beneficial include management of pain, cardiac hypertrophy, and autoimmune disease.

Given that AnkB is encoded by a large gene (~400 kb), human mutations in this gene would be anticipated to be diverse in phenotype with a variety of alleles. The present findings raise the possibility that unrecognized mutations in AnkB could result in multiple organ system dysfunction. Moreover, AnkB mutations affecting heart rhythm and glucose regulation, even if initially subtle, could result in mutually reinforcing pathology resulting in a significantly lowered life expectancy. For example, serious disease could be anticipated if an initially mild hyperglycemia as described for (+/−) mice were combined with other consequences of AnkB deficiency including defective cardiac conduction, compromised immune response, peripheral neuropathy, and obesity due to disordered endocrine balance.

One candidate disorder that may involve AnkB is the dominantly-inherited type 4 long QT syndrome, an a typical variant of long QT syndrome, which possesses a prolonged QT interval with the unusual feature of sinus bradycardia. Long QT syndromes have normally been attributed to ion channel mutations, including $Na^+$ and $K^+$ channels; however, the underlying defect responsible for this Type IV variant is unknown. This syndrome results in sudden cardiac death and shares similar features with AnkB (+/−) mice including sinus bradycardia and prolonged QT interval. Moreover, this disorder maps to the same chromosome site of 4q25–27 (Schott et al, Am. J. Hum. Genet. 57:1114–22 (1995)) as the gene encoding AnkB. These considerations indicate that the Ank-B mouse provides a useful animal model to explore therapeutic approaches for treatment of type IV long QT syndrome.

EXAMPLE 2

Figure 9A:
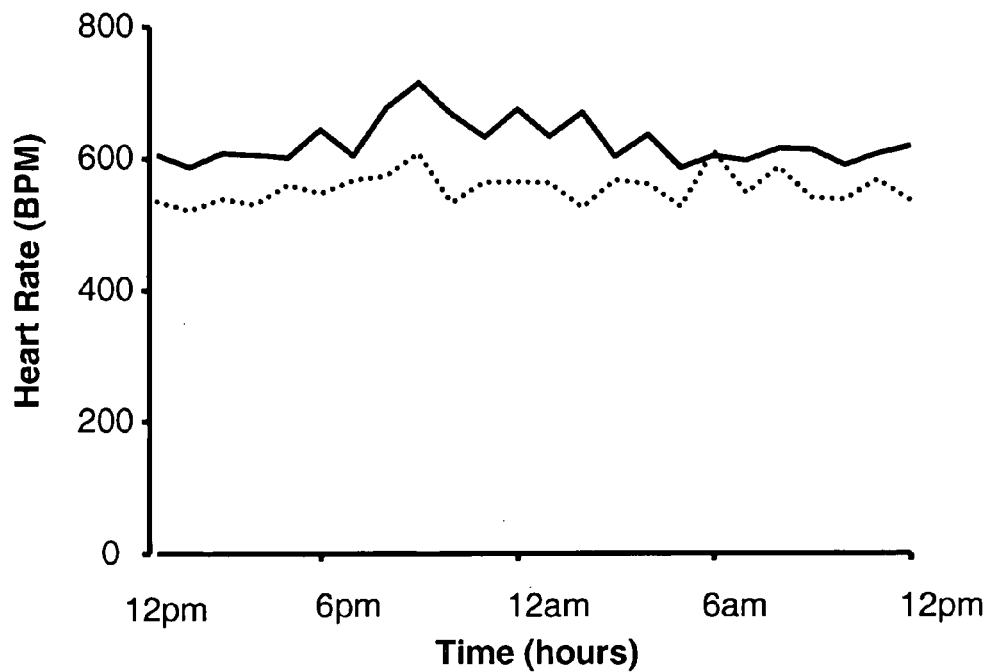
FIGS. 9A and 9B Mean heart rate in conscious ankyrin-B (+/+) and (+/−) mice over a 24 hour period (FIG. 9A) and following phenylephrine injections (FIG. 9B). Heart rate tracings for wildtype and ankyrin-B (+/−) littermates injected with 3 mg/kg phenylephrine (n=8 mice). The heart rate of the (+/−) does not reach the same minimum levels as the wildtype and recovers to near resting levels more rapidly than wildtype animals.
Figure 9B:
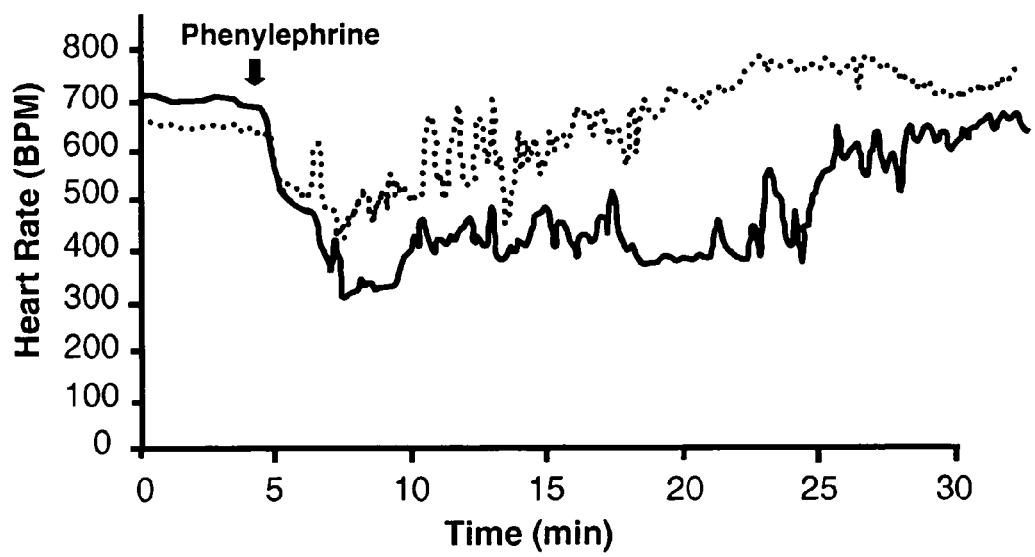
Figure 10A:
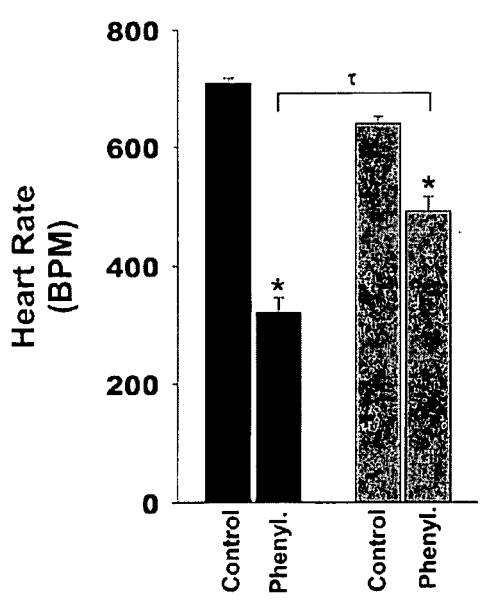
FIGS. 10A–10D. Heart rate changes in response to α-adrenergic stimulation with phenylephrine is attenuated in (+/−) mice.
Figure 10B:
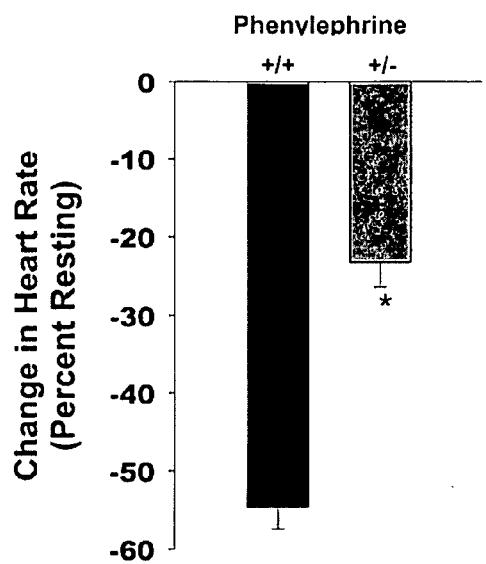
Figure 10C:
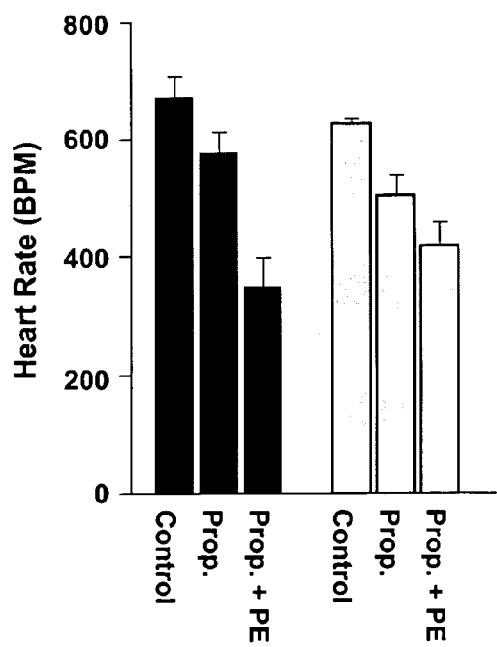
Figure 10D:
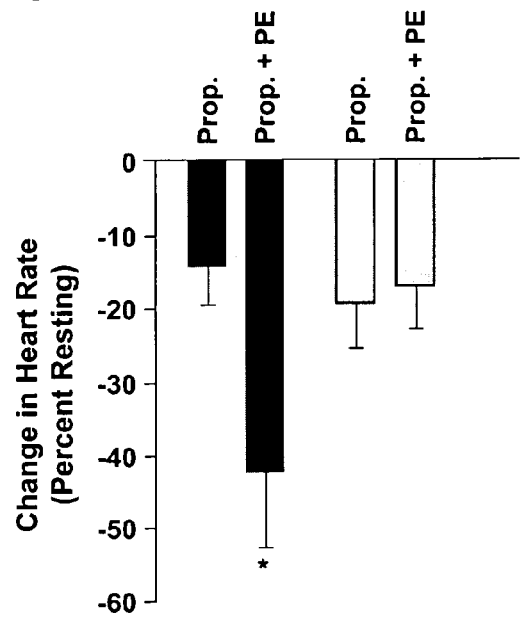

Ankyrin-B (+/−) Mice Display Reduced Response to Phenylephrine and Endothelin-1 on Heart Rate Ankyrin-B (+/−) Mice Display Reduced Heart Rate To test ankyrin-B heterozygous mice for potential defects in Gαq signaling, ECG radiotransmitter implants were implanted in the abdomen of ankyrin-B (+/−) mice as well as wildtype littermate controls. These probes allow the recording of real time ECG and thus heart rate recordings in conscious, non-anethestized mice. 24 hour recordings of wildtype mice compared to heterozygote animals show overall bradycardia in the heterozygote (FIG. 9).

Ankyrin-B Mice Display Decreased Sensitivity to Alpha-Adrenergic Stimulation

Ankyrin-B (+/−) mice and wildtype littermates were injected with the alpha-adrenergic receptor agonist phenylephrine (PE, an α-adrenergic agonist). As expected, when wildtype mice where intraperitoneally injected with phenylephrine (3 mg/kg) there was a rapid decrease in heart rate, a sustained plateau, followed by a slow return back to baseline levels (FIG. 9). In contrast, ankyrin-B (+/−) mice show a significant decreased heart rate sensitivity in response to PE injection.

Since the effects of systemic administration of phenylephrine are mediated via the baroreflex response, experiments were also performed injecting the beta receptor antagonist, propanolol, prior to phenylpheine. In response to propanolol, both wildtype and ankyrin-B heterozygote mice displayed typical decreases in heart rate which were not significantly different (FIG. 10). However, in response to the phenylephrine injection, ankyrin-B heterozygous mice again display major differences in response to alpha-adrenergic activation, displaying maximal decreases that are ~50% of the wildtype response (FIG. 10).

Figure 11A:
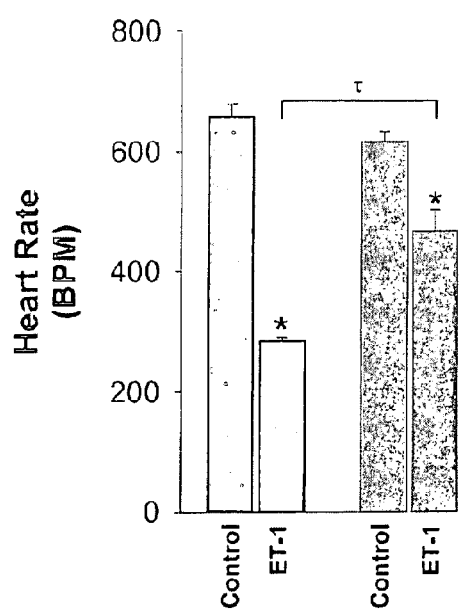
FIGS. 11A and 11B. Heart rate changes in response to $G\alpha_q$-stimulation with Endothelin-1 is attenuated in (+/−) mice.
Figure 11B:
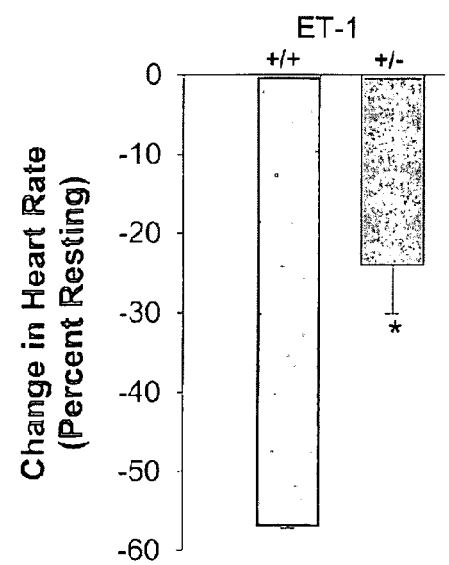

Next examined was the affect of endothelin-1 administration on the heart rate of ankyrin-B (+/−) or wildtype littermates. Endothelin-1, like phenylephrine, signals via a Gαq-coupled receptor, leading to increases in IP3 and DAG and intracellular calcium release. Consistent with the data using phenylephrine, 300 ng/kg endothelin-1 administration results in a significant decrease in heart rate in wildtype animals (FIG. 11). In the ankyrin-B (+/−) mice, these changes were significantly reduced (FIG. 11). Therefore, together with phenylephrine experiments, these data indicate that G protein dependent signaling is compromised in ankyrin-B (+/−) mice.

Beta-Receptor Stimulation is not Affected in Ankyrin-B (+/−) Mice

Figure 12A:
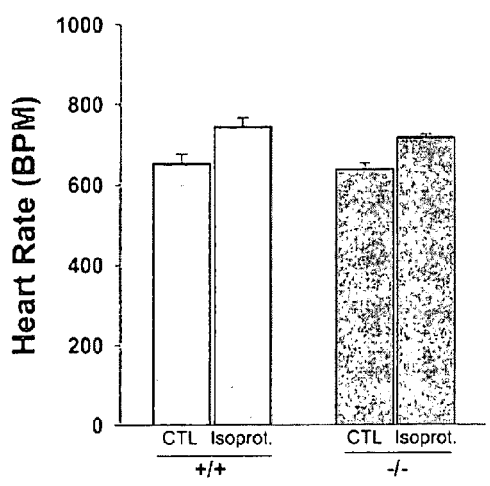
(FIG. 12A) Shown are quantitative data of telemetry recordings of heart rate in beats per minute (BPM) in (+/+) and (+/−) mice prior to (CTL) and following isoproterenol treatment. The +/+ and +/− responsed equally to isoproterenol treatment. (P>0.05, ANOVA).
Figure 12B:
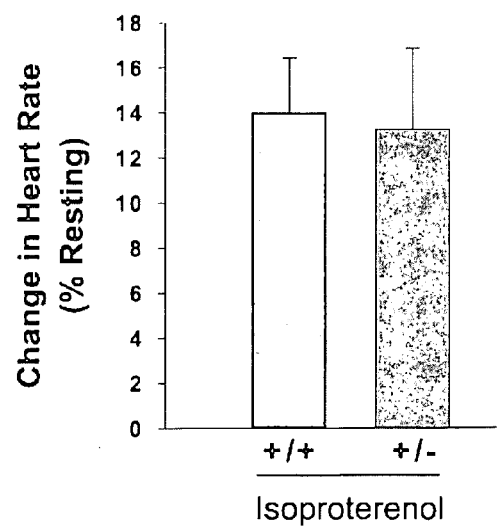
(FIG. 12B) Data are expressed as percent changes in heart rate. Black bars represent wildtype mice, while grey bars represent heterozygotes. Shown are representative heart rate traces for (+/+) mice (solid line) and (+/−) mice (dotted line). For these measurements, the average heart over the entire hour was plotted. It was also determined that the (+/−) heart rate over this period is significantly different from the wild type animal (P<0.05; ANOVA).
Figure 13A:
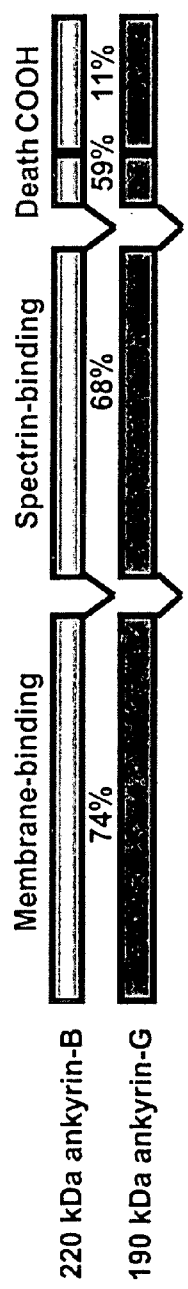
Figure 13B:
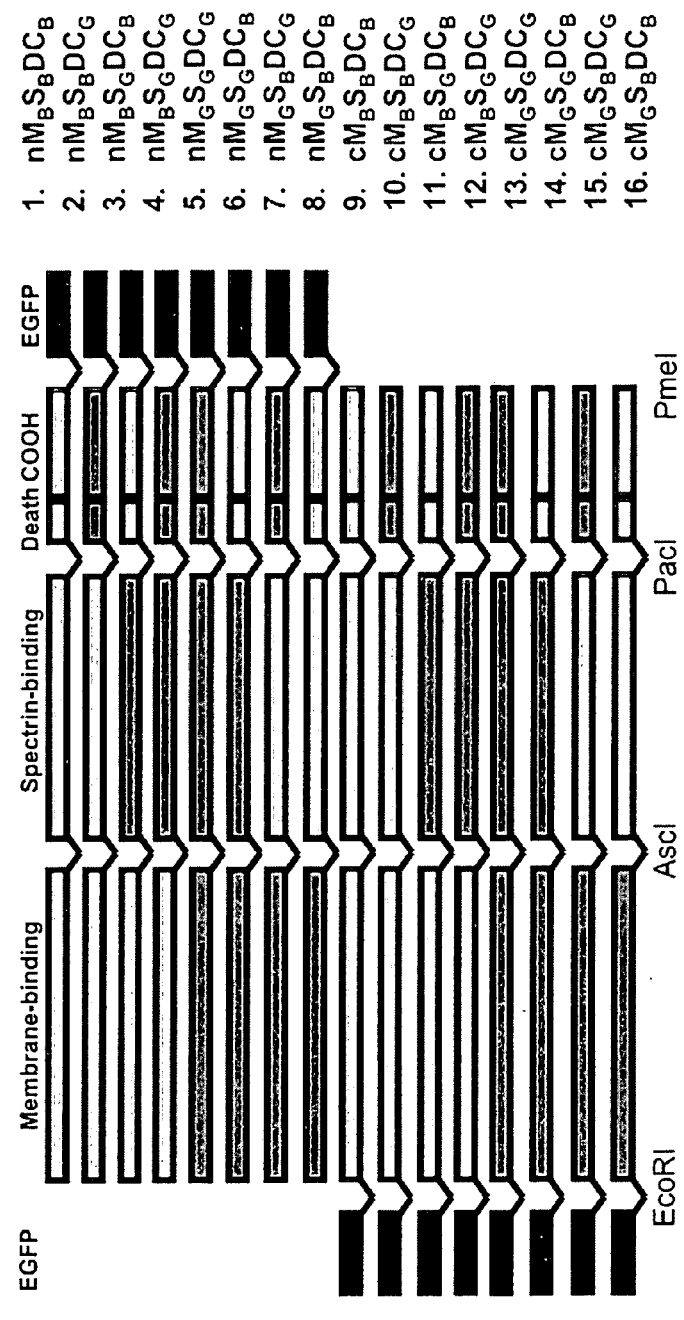
Figure 14B:
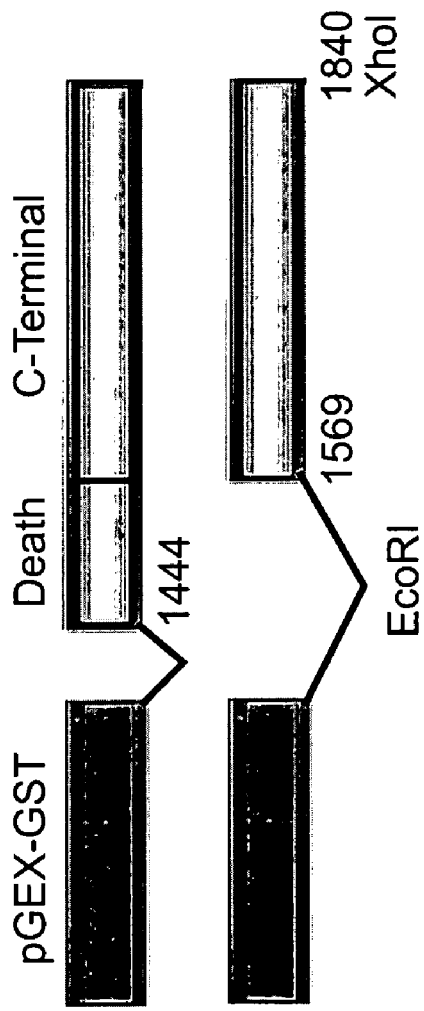
Figure 15A:
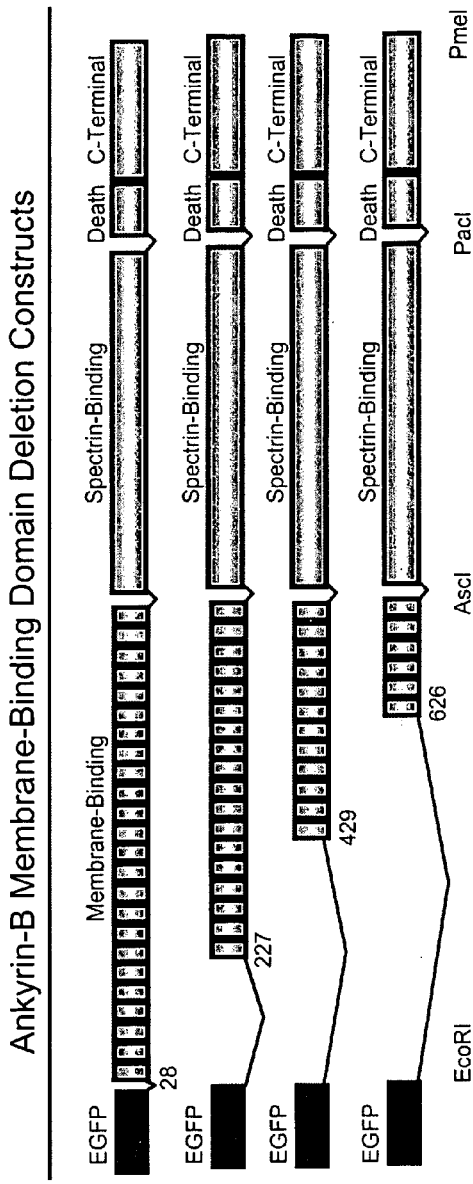
FIGS. 15A and 15B. Ankyrin-B membrane-binding domain deletion constructs.
Figure 15B:
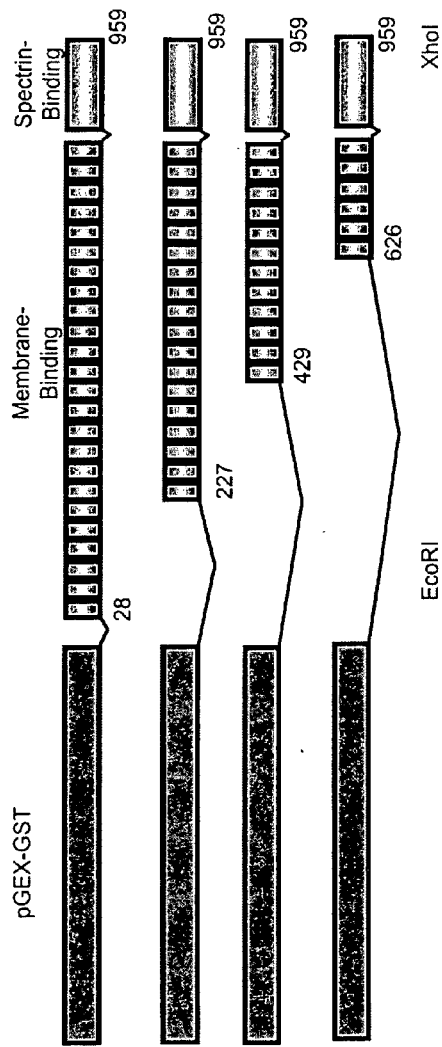
Figure 16:
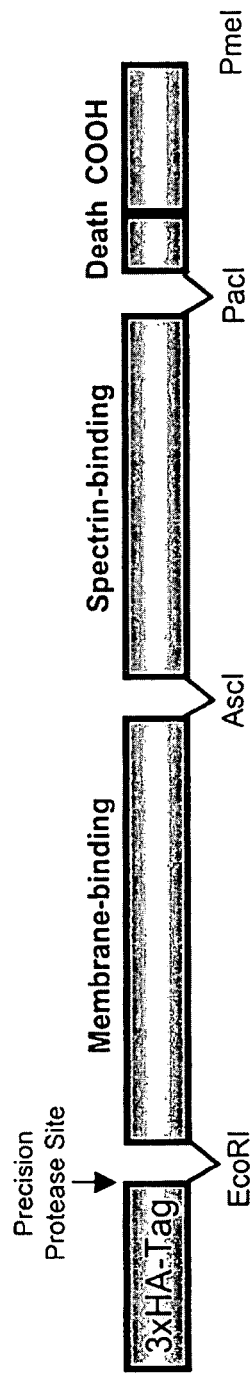
FIG. 16. Full-length 220 kDa Ankyrin-B in baculoviral vector. Schematic of the full-length 220 kDa ankyrin-B construct in the BAKPAK baculoviral transfer vector.

Wildtype and ankyrin-B heterozygous mice respond similarly to beta-adrenergic stimulation. The injection of wildtype and ankyrin-B (+/−) mice with the beta-receptor agonist isoproterenol (50 mg/kg) resulted in similar changes in heart rate in both wildtype and ankyrin-B (+/−) mice. Therefore, ankyrin-B heterozygous mice do not appear to possess abnormalities in beta-adrenergic receptor signaling. (See FIG. 12.)

EXAMPLE 3

Description of Ankyrin-B DNA Constructs

Construct generation. 220 kDa ankyrin-B and 190 kDa ankyrin-G chimeric EGFP expression constructs were engineered using common molecular techniques. Briefly, an internal EcoRI site in ankyrin-B was removed by Quickchange PCR (Stratagene; La Jolla, Calif.). Next, pEGFPC2 and pEGFPN3 were modified to create a novel PmeI site in the pEGFP multiple cloning site (3'). The membrane-binding domain of 220 kDa ankyrin-B and 190 kDa ankyrin-G were amplified by PCR to engineer a 5' EcoRI site and 3' AscI site resulting in a three amino acid linker (Gly-Ala-Pro) between the membrane- and spectrin-binding domains. The spectrin-binding domains of 220 kDa ankyrin-B and 190 kDa ankyrin-G, (which lacks the serine/threonine rich insert and tail of 270 kDa ankyrin-G) were amplified by PCR with 5' AscI and 3' PacI sites resulting in a three amino acid linker (Leu-Ile-Asn) between and spectrin-binding and death/C-terminal domains. Finally, the death/C-terminal domains of ankyrin-B and ankyrin-G were amplified to contain 5' PacI and 3' PmeI sites. Amplified constructs were inserted into the modified pEGFP vectors using the available EcoRI and PmeI sites to create full-length GFP 220 kDa ankyrin-B and 190 kDa ankyrin-G expression constructs, as well as six other full-length ankyrin-B and ankyrin-G chimeras. Similar methods were utilized to create the additional C-terminal domain constructs: Ankyrin-B Death/C-terminal GFP; Ankyrin-G Death/C-terminal GFP; Ankyrin-B Full length ΔDeath GFP; and Ankyrin-B Full length ΔC-terminal GFP. The C-terminal domain of ankyrin-B was also placed into pGEX vector (Gibco) using the available cloning sites for EcoRI and XhoI. Using available protein characterization software (Expasy Prosite; www.expasy.org), it was determined that the Death/C-terminal domain contains multiple predicted phosphorylation sites within this domain; including two protein kinase A, seven protein kinase C, and one tyrosine kinase site (two PKA sites also were found to be putative PKC sites). Using the full-length Ankyrin-B GFP construct as a template, site-directed alanine-scanning mutagenesis (Invitrogen) was performed and eight phosphorylation mutant constructs were generated where the predicted phosphorylation site was replaced by an alanine. Membrane-binding domain constructs were generated also using EcoRI and PmeI restriction sites within the engineered EGFP plasmid. The membrane-binding domain of ankyrin-B was also placed into pGEX vector (Gibco) using the available cloning sites for EcoRI and XhoI. (See FIGS. 13–16.)

EXAMPLE 4

Ankyrin-B C-Terminal Domain Determines Activity of Ankyrin-B/G Chimeras in Rescue of Abnormal IP3 and Ryanodine Receptor Distribution in Ankyrin-B (−/−) Neonatal Cardiomyocytes Experimental Procedures:

Cell culture and transfections. Cardiomyocytes were dissociated from one to two day old ankyrin-B (−/−) (Scotland et al, J. Cell Biol. 143:1305–1308 (1998)) or wildtype littermates as previously described (Tuvia et al, J. Cell Biol. 147:995–1008 (1999)). For transfection assays, purified endotoxin-free DNA was isolated using Qiagen MidiPreps (Qiagen, Valencia, Calif.) and transfected using Effectene (Qiagen) or Genefector (Vennnova, Pompano, Fla.) according to manufacturer's guidelines into 3–4 day old myocyte cultures or cultured HEK293 cells. Concentrations and time for assays were determined empirically to ensure high population transfection efficiency (~70%) together with a moderate level of single cell expression.

Figure 20A:
FIGS. 20A and 20B. 220 kDa GFP ankyrin-B restores normal contraction rates to ankyrin-B (−/−) cardiomyocytes. Spontaneous contractions of wildtype or ankyrin-B null (−/−) cardiomyocytes were monitored by light microscopy (FIG. 20A). Ankyrin-B (−/−) myocytes were transfected with ankyrin-B or ankyrin-G constructs and 24–36 hours later, spontaneous contractions were monitored. For each experiment, a mock, GFP, or untransfected control was measured (FIG. 20B). Experiments were performed at least three times with greater than 50 myocytes measured per culture. * Significant differences from wildtype levels, P<0.05, ANOVA.
Figure 20B:
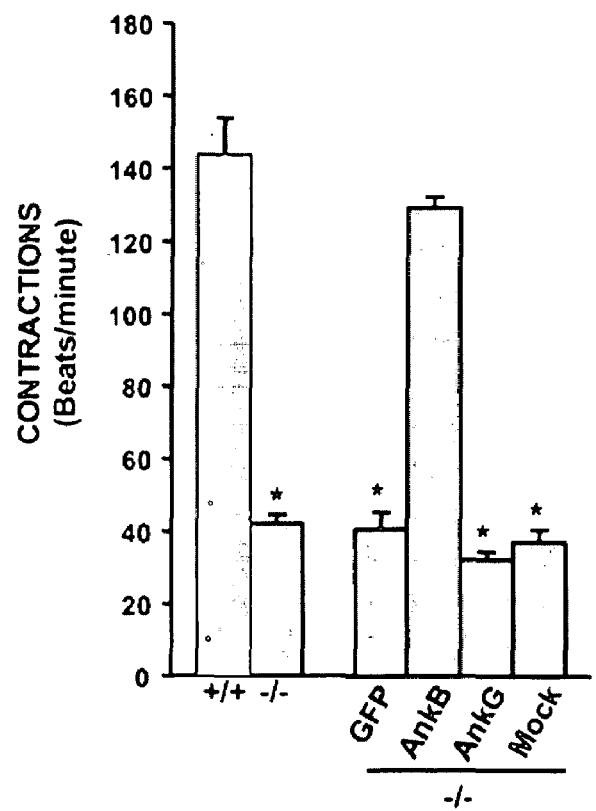

Plasmids. pEGFP (Clontech; Palo Alto, Calif.) 220 kDa ankyrin-B and 190 kDa ankyrin-G chimeric expression constructs were engineered using common molecular techniques. Briefly, an internal EcoRI site in ankyrin-B was removed by Quickchange PCR (Stratagene; La Jolla, Calif.). Next, pEGFPC2 and pEGFPN3 were modified to create a novel PmeI site in the pEGFP multiple cloning site (3'). The membrane-binding domain of 220 kDa ankyrin-B and 190 kDa ankyrin-G were amplified by PCR to engineer a 5' EcoRI site and 3' AscI site resulting in a three amino acid linker (Gly-Ala-Pro) between the membrane- and spectrin-binding domains. The spectrin-binding domains of 220 kDa ankyrin-B and 190 kDa ankyrin-G, (which lacks the serine/threonine rich insert and tail of 270 kDa ankyrin-G) were amplified by PCR with 5' AscI and 3' PacI sites resulting in a three amino acid linker (Leu-Ile-Asn) between and spectrin-binding and death/C-terminal domains. Finally, the death/C-terminal domains of ankyrin-B and ankyrin-G were amplified to contain 5' PacI and 3' PmeI sites. Amplified constructs were inserted into pNEB193 (New England Biolabs; Beverly, Mass.) and subsequently ligated into the modified pEGFP vectors using the available EcoRI and PmeI sites to create full-length GFP 220 kDa ankyrin-B and 190 kDa ankyrin-G expression constructs, as well as six other full-length ankyrin-B and ankyrin-G chimeras (FIG. 20). Similar methods were utilized to create additional constructs (see FIGS. 24A–25A). All plasmids were verified first by restriction digestions and sequencing (ABI Prism; Duke DNA Core Facility), and subsequently expressed in HEK293 cells (American Type Culture Collection (ATCC); Manassas, Va.), and immunoblotted using GFP-specific antisera (Clontech) to ensure full-length protein products.

Quantitation of spontaneous contractions. Quantitation of the cardiomyocyte contraction rates (beats per minute) was analyzed using DIC microscopy. Data represent at least three separate experiments (using at least three different mice), with a minimum of fifty cardiomyocytes analyzed per group. Myocytes were subsequently fixed in paraformaldehyde and GFP-ankyrin chimera expression was confirmed by immunostaining (GFP-specific antisera) and confocal microscopy as described below.

Immunofluorescence and immunoblotting. Primary cultures were fixed in 2% paraformaldehyde, permeabilized, and incubated with primary antibodies including green fluorescent protein (mouse, rabbit and chicken; Chemicon; Temecula, Calif.), α-actinin (mouse; Sigma, St. Louis, Mo.), IP3 receptor (type 1, rabbit; type 2, rabbit; Pan-antibody; rabbit), ryanodine receptor (type 2; mouse), SERCA2 (mouse; Affinity Bioreagents, Cambridge, UK), or ankyrin-B (mouse and rabbit), followed by appropriate secondary antisera (Alexa 488, 568; Molecular Probes; Sunnyvale, Calif.), and analyzed by confocal microscopy. Images at each wavelength (488 and 568 nm) were collected separately to ensure that there was no fluorescent channel bleed-through. GFP ankyrin-transfected HEK293 cells were processed for SDS-PAGE and western blotting essentially as described (Scotland et al, J. Cell Biol. 143:1305–1308 (1998)) using GFP-specific antisera (Chemicon). All rescue experiment images are representative of hundreds of transfected myocytes in each culture. Experiments were repeated a minimum of three times using different neonatal mice.

Statistics. Data were analyzed using either paired two-tailed Students t tests or two-way ANOVA, and P values less than 0.05 were considered significant (*). Error bars in figures represent SEM.

Results:

Ankyrin-B Localization Precedes Calcium Homeostasis Protein Organization in Cultured Neonatal Cardiomyocytes.

Figure 17:
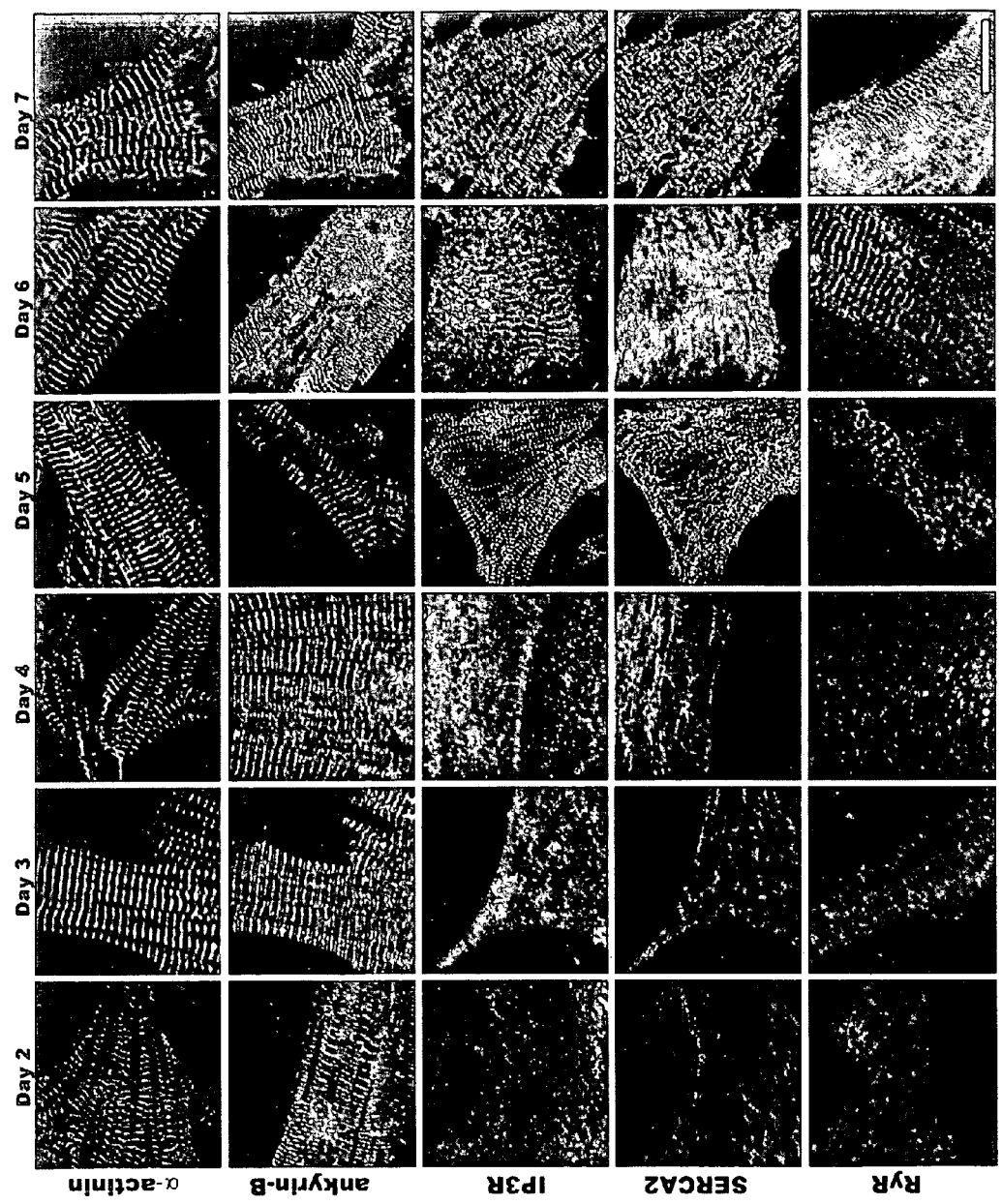
FIG. 17. Alpha-actinin and ankyrin-B precede IP3R, RyR, and SERCA in achieving a differentiated striated localization in primary cultures of cardiomyocytes. Neonatal cardiomyocytes were isolated from postnatal day one or two wildtype mice and cultured for up to seven days. Cultures were subsequently processed for immunofluorescence using antisera against α-actinin, ankyrin-B, ryanodine receptor (type 2), IP3 receptor, or SERCA2 as described. Bar equals 10 μm.
Figure 18B:
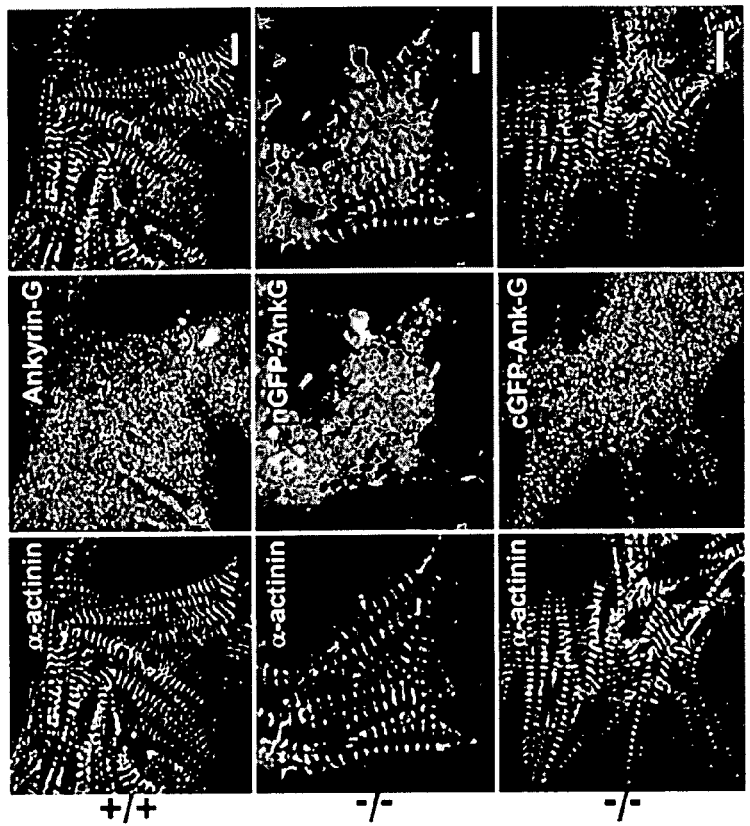
FIGS. 18A and 18B. GFP 220 kDa ankyrin-B and 190 kDa ankyrin-G show similar localizations to corresponding endogenous ankyrins. Four to six day old wildtype and ankyrin-B (−/−) cardiomyocyte cultures were transfected with (FIG. 18A) 220 kDa GFP ankyrin-B or (FIG. 18B) 190 kDa GFP ankyrin-G. Following 24–35 hours, cultures were fixed and processed for immunofluorescence and confocal microscopy.
Figure 18A:
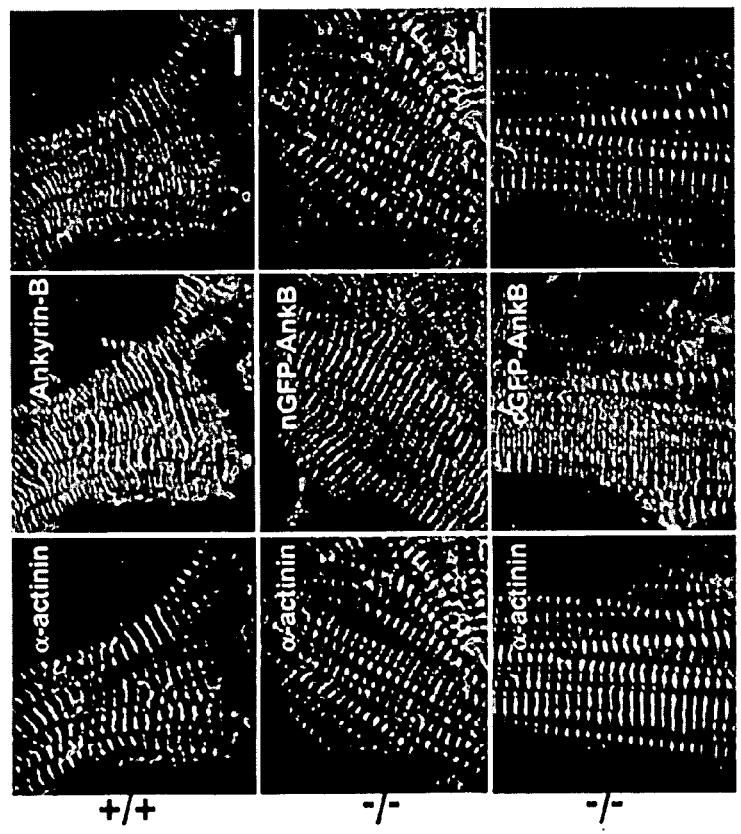

The goal of this study was to identify the ankyrin domain(s) that determine the difference between ankyrin-B and ankyrin-G in their cellular localization and ability to restore localization of IP3R and RyR in primary cultures of ankyrin-B (−/−) cardiomyocytes from 1–2 day old neonatal mice. The first step in establishing a rescue assay was to define culture conditions where ankyrin-B, IP3R and RyR are normally organized. Cardiomyocytes were not examined before 24 hours of culture, since at this stage cells were not yet firmly adhered to the coverslip and were routinely spherical (Larsen et al, Histochem. Cell. Biol. 112(4):307–16 (1999)). However, in two-day old cardiomyocyte cultures, cells are firmly attached and α-actinin displays a costameric pattern as revealed by the normal Z-line localization pattern (FIG. 17). At this early developmental stage, ankyrin-B is striated and highly concentrated at the A-band. In addition, some ankyrin-B staining (~15–20% of the total level of ankyrin-B) co-localizes with α-actinin, as well as in small (<0.5 μm) punctate structures throughout the cardiomyocyte (FIGS. 17, 18A). In day two cultures, the organization of the SR is poorly developed, as evidenced by the diffuse, punctate distribution of ryanodine receptor (RyR), IP3 receptor (IP3R), and the SR/ER calcium ATPase (SERCA2; FIG. 17, left most portion of panel). Components of the calcium-release/uptake machinery of the SR begin to organize at approximately four days in culture (see SERCA2 staining); however complete organization of ryanodine and IP3 receptor calcium-release channels does not display a more defined pattern until postnatal day 6 and 7. These developmental data also correlate with our observations that normal calcium waves and cellular contractions take several days to display a rhythmic, fluid characteristic. The early expression and organized distribution of ankyrin-B in neonatal cardiomyocytes is consistent with a role of ankyrin-B in subsequent organization of IP3 and ryanodine receptors, which become localized only later in cardiomyocyte development.

These developmental time course experiments provided a framework for rescue studies using transiently transfected GFP expression constructs (see below) (FIG. 21). Since all of the cardiac molecules examined display a normal striated pattern by 6 to 7 days in culture, this developmental stage was chosen to address the effect of expression constructs on receptor channel localization. Therefore, cultures were transfected with the various GFP expression constructs at day 4–5 and subsequently analyzed at 6–7 days in culture.

GFP-Ankyrin Constructs Display Localization Patterns That are Similar to Endogenous Ankyrins The next step in establishing a system for evaluating ankyrin-dependent rescue of IP3R and RyR localization in cardiomyocytes was to develop methods for transfection of cardiomyocytes resulting in normal localization of GFP-tagged ankyrin-B and ankyrin-G. 220 kDa ankyrin-B and 190 kDa ankyrin-G cDNAs were generated which were either N- or C-terminally fused with enhanced green fluorescent protein (pEGFP; FIGS. 20A, B). GFP expression was adjusted to low levels such that GFP signal could only be detected by immunofluorescent staining with GFP antibody. Endogenous ankyrin-B in wildtype cardiomyocytes localizes mainly at the A-band, with lower levels at the Z-line (FIG. 17; FIG. 18A; upper panel). Similar to endogenous ankyrin-B, both the N- and C-terminal GFP-fusions of 220 kDa ankyrin-B are primarily localized to the A-band in transfected ankyrin-B null cardiomyocytes with a less intense signal observed at the Z-line (FIG. 18A; shown are data using both the N-terminal GFP fusion, referred to as nGFP-ankyrin-B, and the C-terminal construct, cGFP-ankyrin-B). Endogenous ankyrin-G in wildtype myocytes displays a diffuse membrane expression (FIG. 18B; upper panel) which is also seen using both N- and C-terminal GFP-fusions of 190 kDa ankyrin-G (FIG. 18B, lower panel).

These data establish that transfected GFP-ankyrin-B and ankyrin-G are expressed and targeted to identical localization patterns as their endogenous counterparts under our experimental conditions. In addition, these experiments demonstrate that GFP fused at either end of the proteins, or the presence of the additional six linker-residues (between the three major ankyrin domains), do not interfere with the steady-state localization of either GFP 220 kDa ankyrin-B or 190 kDa ankyrin-G. Evidence that transfections under these conditions are not toxic to cardiomyocytes is that reduced contraction rates of ankyrin-B (−/−) cells is restored by transfection with ankyrin-B constructs (see below).

Figure 19B:
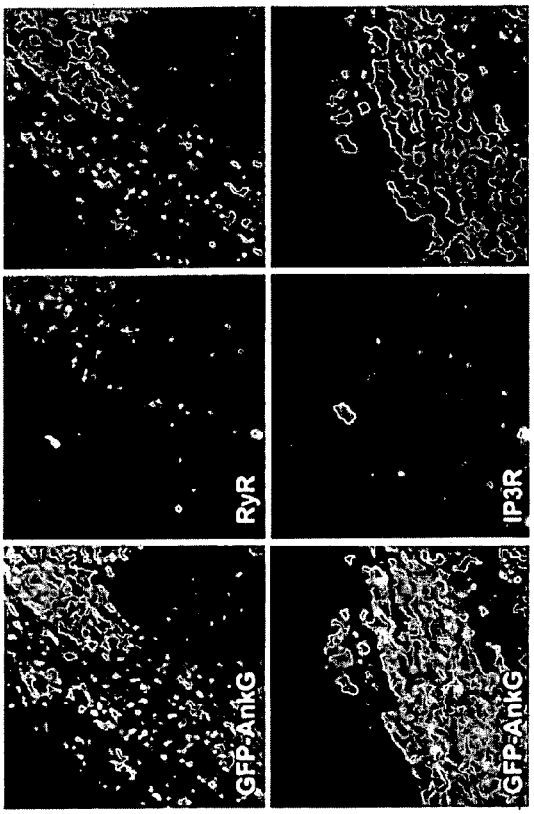
FIGS. 19A and 19B. GFP-220 kDa ankyrin-B restores IP3R and RyR localization in neonatal cardiomyocytes while 190 kDa GFP-ankyrin-G is inactive. Four to six day old ankyrin-B (−/−) cardiomyocytes were transfected with (FIG. 19A) 220 kDa GFP ankyrin-B constructs or (FIG. 19B) 190 kDa GFP ankyrin-G constructs. In each case, both the N- and C-terminally fused GFP constructs were used. Following 24–36 hours, cultures were fixed and processed for immunofluorescence and confocal microscopy using antisera against GFP, IP3 receptor (IP3R) or ryanodine receptor type 2 (RyR)-specific antisera. Only the GFP-tagged ankyrin-B construct is capable of restoring striated expression patterns to IP3 and ryanodine receptors. Scale bar, 5 μm. Data are representative of hundreds of transfected myocytes from four different mice.
Figure 19A:
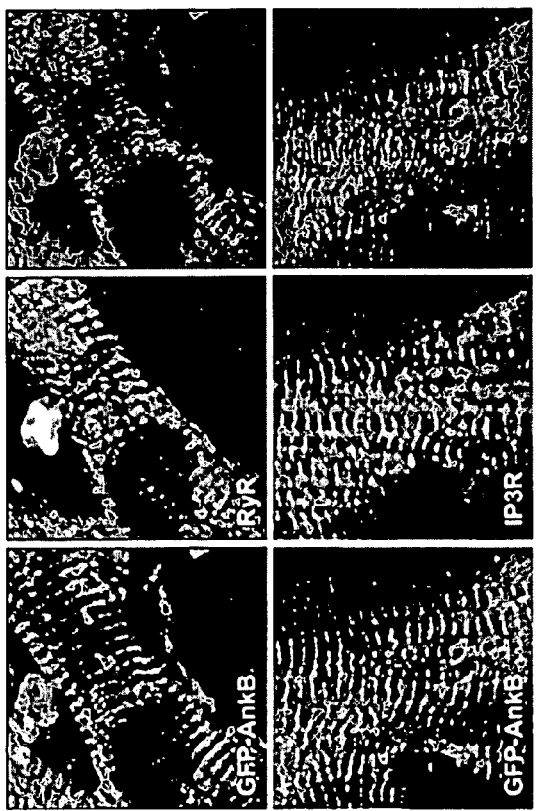

GFP-220 kDa Ankyrin-B Rescues IP3 and Ryanodine Receptor Localization and Restores Normal Rates of Contraction in Ankyrin-B (−/−) Cardiomyocytes Ryanodine and IP3 receptors (FIGS. 19A, 19B), but not other calcium homeostasis proteins (including SERCA2, triadin, calreticulin, or the dihydropyridine receptor (DHPR)) are mis-localized in ankyrin-B (−/−) cardiomyocytes. Transfection with plasmids encoding GFP-tagged 220 kDa ankyrin-B (both $NH_2$- and COOH-terminal fusions; FIG. 19A), but not GFP alone, restores the normally striated distribution of both ryanodine and IP3 receptors in neonatal ankyrin-B null cardiomyocytes. In contrast, transfection with plasmids encoding GFP-tagged 190 kDa ankyrin-G does not restore a striated localization of either IP3 or ryanodine receptor, which exhibit localization patterns in transfected cells resembling mock or untransfected phenotypes (FIG. 19B). The majority of transfected GFP-tagged 220 kDa ankyrin-B, which is distributed primarily over the A band, does not colocalize with either IP3R or RyR, which are localized over the Z-line (FIG. 19A).

Spontaneous contraction rates of ankyrin-B (−/−) cardiomyocytes were measured before and after transfection to assess the physiological impact of restoring IP3R and RyR localization in ankyrin-B deficient cardiomyocytes. Wildtype cardiomyocytes contract rhythmically from a central perinuclear point at 144±10 spontaneous beats per minute (bpm; n=8 mice, >20 cells averaged/mouse), while ankyrin-B (−/−) cardiomyocytes contract at 42±3 bpm ($P<0.05$, n=5; FIG. 20). Next measured were spontaneous contraction rates of ankyrin-B (−/−) cultures transfected with GFP-220 kDa ankyrin-B or GFP-190 kDa ankyrin-G. Analysis of GFP-ankyrin expression by immunofluorescence using GFP-specific antisera demonstrated that transfection efficiencies were 60–80 percent (FIG. 20). Therefore, a large number of cardiomyocytes were monitored to arrive at statistically significant sample populations. Ankyrin-B (−/−) cultures transfected with GFP, either C- or N-terminally fused to 220 kD ankyrin-B contract at a rate similar to that of wildtype cultures (129±3 bpm; $P>0.05$, n=4 mice, >80 cells counted/mouse). In contrast to the normal beat frequency observed in ankyrin-B transfected cells, ankyrin-B null myocytes expressing either C- or N-terminal GFP fusions of 190 kDa ankyrin-G display contraction rates that are not different from untransfected cardiomyocytes (32±2 bpm, n=4). As expected, the beat frequencies of mock transfected (37±4 bpm, n=3), or GFP transfected myocytes (41±5 bpm, n=3) are not significantly different than untransfected null cultures. These results are consistent with the lack of striated patterns of IP3 and ryanodine receptor distribution in these cultures (FIG. 19). Taken together, these results demonstrate that the abnormal beat frequency characteristics displayed by ankyrin-B null cardiomyocytes are the direct result of a single molecular defect, since the reintroduction of 220 kDa ankyrin-B into these cultures restores normal contraction rates.

The Ankyrin-B C-Terminal Domain Determines Activity of Ankyrin-B/G Chimeras in Subcellular Localization and Rescue of IP3 and Ryanodine Receptor Distribution Ankyrin-B/G chimeric constructs were generated with the eight possible combinations of 220 kDa ankyrin-B and 190 kDa ankyrin-G membrane-binding, spectrin-binding, and death/C-terminal domains (FIG. 21B) in order to determine the essential domain(s) required for native ankyrin-B targeting and ability to rescue IP3R and RyR localization in ankyrin (−/−) cardiomyocytes. Each construct (containing three amino acid linkers between domains) was N- and C-terminally fused with pEGFP resulting in a total of sixteen ankyrin-B/ankyrin-G chimeras. Western blot analysis of cultured HEK293 cells transfected with these constructs using GFP-specific antisera revealed that ankyrin-B/G expression constructs generate proteins that migrate at the expected molecular weight (FIG. 21C).

GFP-tagged ankyrin-B/ankyrin-G chimeric constructs were transfected into 4–5 day old ankyrin-B (−/−) cardiomyocytes and the localizations of the GFP-ankyrin chimera, as well as IP3 and ryanodine receptor were subsequently examined in the same cells by double-label immunofluorescence. For these experiments, either N- or C-terminal fusions of GFP-ankyrin chimeras yielded identical findings; otherwise results show data using the N-terminally fused constructs, i.e., those with GFP located at the C-terminus of ankyrins.

Figure 22:
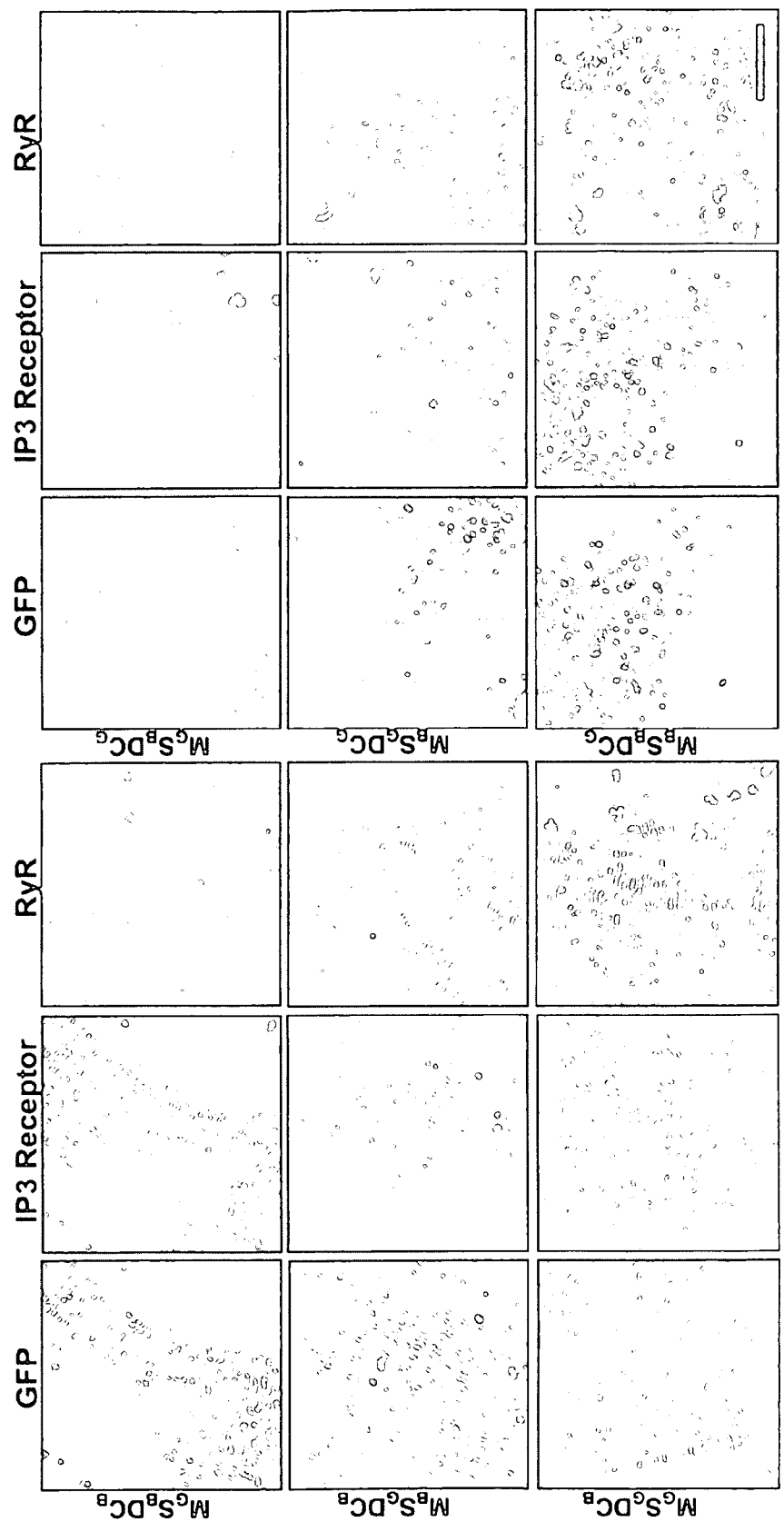
FIG. 22. Ankyrin-B/ankyrin-G chimeras containing the death/C-terminal domain of ankyrin-B restore IP3R and RyR localization in ankyrin-B (−/−) cardiomyocytes. Four to six day old ankyrin-B (−/−) cardiomyocyte cultures were transfected with GFP-ankyrin $M_G S_B DC_B$, GFP-ankyrin $M_B S_G DC_B$, GFP-ankyrin $M_G S_B DC_G$, GFP-ankyrin $M_B S_G DC_G$, GFP-ankyrin $M_B S_G DC_G$, or GFP-ankyrin M$_G$S$_G$DC$_B$. Following 24–36 hours, cultures were fixed and processed for immunofluorescence and confocal microscopy using antisera against α-actinin, GFP, ryanodine or IP3 receptors. Data are representative of hundreds of transfected myocytes from four different mice using both NH$_2$- and COOH-terminal GFP fusions. Bar equals 7.5 μm. (M=membrane-binding domain, S=spectrin-binding domain, DC=death/C-terminal domain).

Expression constructs where only the membrane-binding domains of ankyrin-B and ankyrin-G have been switched (i.e., comparing full length ankyrin-B, $M_B S_B DC_B$, and $M_G S_B DC_B$) not only show very similar subcellular localization, but both appear equally capable of restoring IP3R and RyR localization in ankyrin (−/−) cultures (compare FIG. 19A and FIG. 22, top left panel). Conversely, the substitution of the ankyrin-B membrane-binding domain onto an ankyrin-G backbone (construct $M_B S_G DC_G$) results in a non-striated pattern of GFP expression and lack of activity in restoring IP3R or RyR localization (FIG. 22). Together, these results demonstrate that the membrane-binding domains of 220 kDa ankyrin-B and 190 kDa ankyrin-G are interchangeable in this rescue assay, even though these domains share only 74 percent amino acid identity in their primary sequences.

Analysis of GFP constructs containing switched ankyrin-B and ankyrin-G spectrin-binding domains reveal that this domain is also interchangeable in the targeting/ rescue assay. For example, chimeric ankyrin $M_B S_G DC_B$ is localized at the A-band and is also capable of restoring the localization of both ryanodine and IP3 receptors (FIG. 22, left panel, middle). Similarly, the spectrin-binding domain of ankyrin-B within the ankyrin-G membrane binding domain and death/C-terminal domain ($M_G S_B DC_G$) is not capable of restoring the normal localization of ankyrin, IP3 or ryanodine receptor (FIG. 22, right panel, top) further demonstrating that the spectrin-binding domain is not the unique region of the molecule that confers normal localization and calcium-channel rescue specificity to 220 kDa ankyrin-B.

The specificity of 220 kDa ankyrin-B targeting and activity in directing localization of IP3R and RyR both reside within the death/C-terminal domain. The presence of the ankyrin-B death/C-terminal domain within the context of ankyrin-G ($M_GS_GDC_B$) can completely restore normal localization of GFP-ankyrin as well as of ryanodine and IP3 receptors (FIG. 22; left panel, bottom; FIG. 23). Furthermore, inclusion of the ankyrin-G death/C-terminal domain within the ankyrin-B (construct $M_BS_BDC_G$) abolished subcellular striated patterns for GFP and ability to restore IP3 or ryanodine receptor localization (FIG. 22; right panel, bottom; FIG. 23). Altogether, these data clearly show that the death/C-terminal domain of 220 kDa ankyrin-B is required both for the localization of ankyrin, and for normal IP3R and RyR localization in cardiac muscle. Interestingly, it was often possible to observe areas of co-localization between calcium-release channels and GFP-ankyrin constructs lacking the ankyrin-B death/C-terminal domain in approximately 1 micron puncta (FIG. 23, compare patterns of labeling $M_GS_GDC_B$ and $M_BS_BDC_G$ (green) with IP3R (red)). This partial overlap in localization of ankyrin and IP3R in the non-rescued cardiomyocytes is in contrast to distinct localization of ankyrin and IP3R in rescued cells (FIG. 23A).

Figure 24A:
FIGS. 24A–24C. The ankyrin-B death/C-terminal domain is necessary but not sufficient to restore IP3R and RyR localization in ankyrin-B (−/−) cardiomyocytes.
Figure 24B:
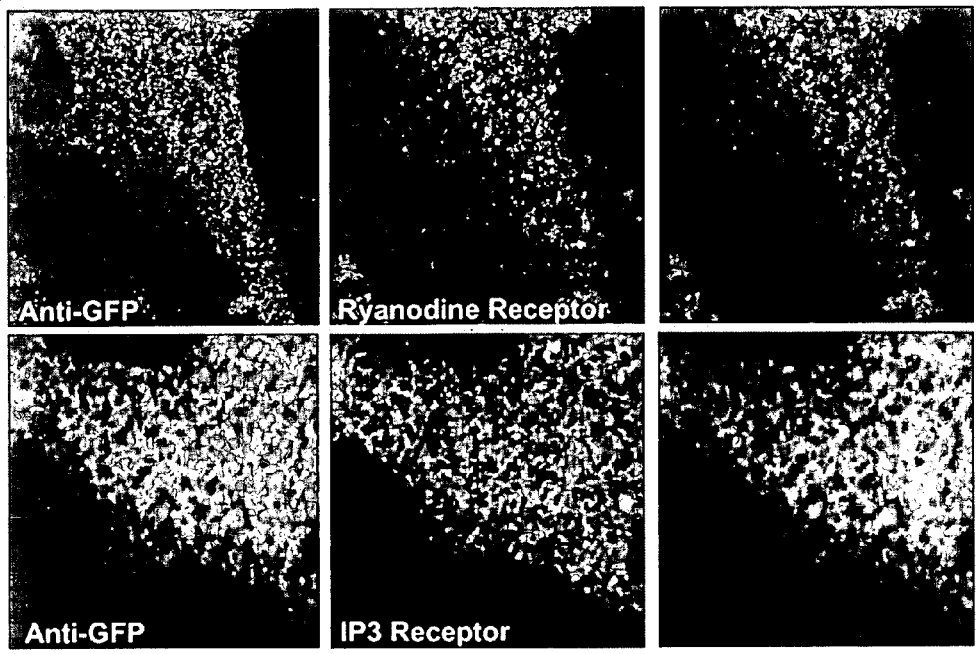
Figure 24C:
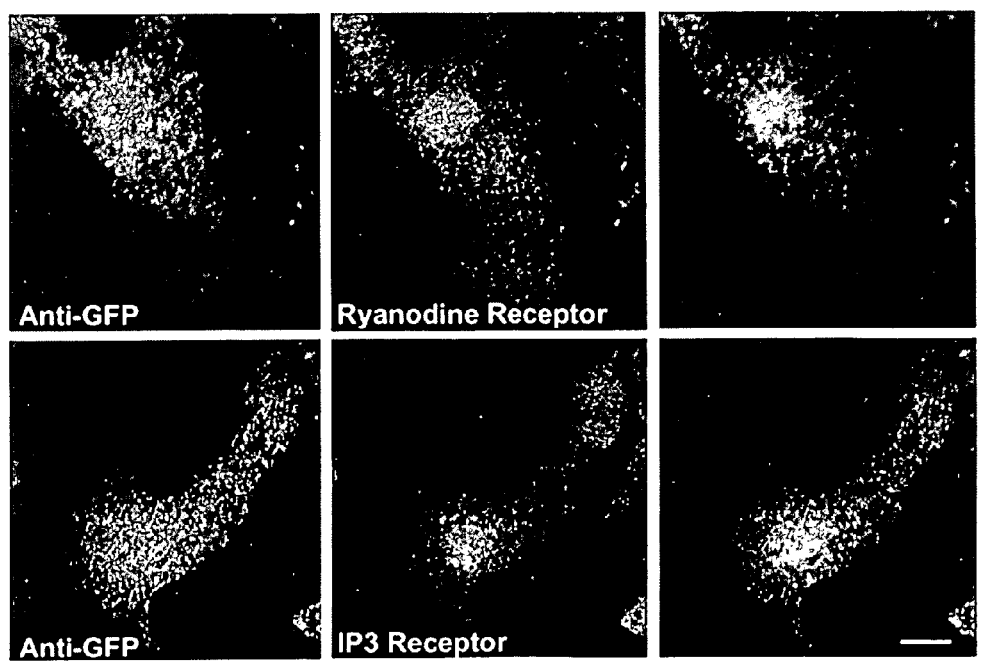

GFP-fusion constructs were next designed containing only the death/C-terminal domain of either ankyrin-B or ankyrin-G (FIG. 24A, left), and their activity in directing protein expression in HEK293 cells confirmed (FIG. 24A, right). Transfection of the death/C-terminal domain of 220 kDa ankyrin-B into null cultures does not restore the normal distribution of IP3 or ryanodine receptor (FIG. 24B), indicating that the death/C-terminal domain of 220 kDa ankyrin-B is necessary (see FIG. 21), but not sufficient for rescue of calcium-release channel localization. As expected, transfection of the ankyrin-G death/C-terminal domain construct into ankyrin-B (−/−) myocytes also does not restore normal localization to either ryanodine or IP3 receptors (FIG. 24C).

Figure 25A:
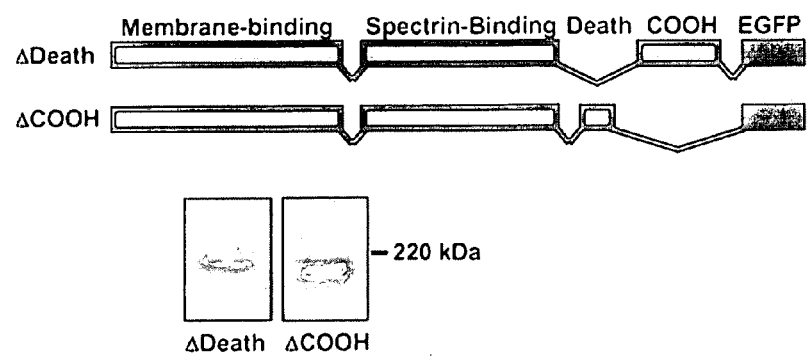
(FIG. 25A) Structural schematic of GFP ankyrin-B constructs lacking the death domain or COOH-terminus. The expression of these constructs was confirmed by transfection of HEK293 cell and western blotting extracts of these cells with GFP antisera (right panel). Ankyrin-B (−/−) cardiomyocytes were transfected with GFP-tagged full-length 220 kDa ankyrin-B constructs lacking the death domain or COOH-terminus, and subsequently immunostained with antisera to (FIG. 25B) α-actinin and GFP and (FIG. 25C) ryanodine or IP3 receptors. Bar equals 2.5 μm. Representative images were taken from three separate experiments.
Figure 25B:
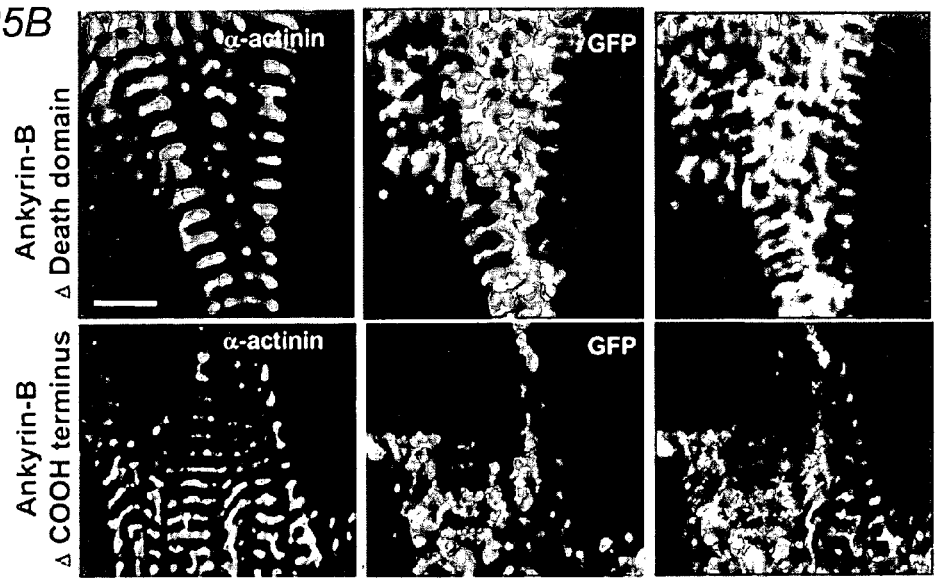
Figure 25C:
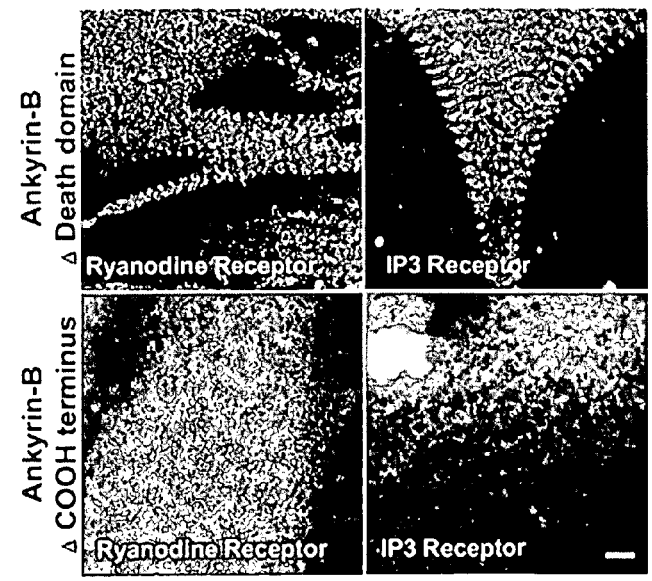

Ankyrin-B expression plasmids with deletions of either the death domain or the C-terminal domain were next constructed (FIG. 25A; left). These constructs were sequenced and expression of the correct molecular weight GFP-fusion was confirmed in HEK293 cells (FIG. 25A; right). Ankyrin-B (−/−) cardiomyocytes transfected with GFP-full length ankyrin-B lacking the death domain exhibit striated localization patterns of GFP, suggesting that the death domain is not critical in targeting ankyrin within cardiomyocytes (FIG. 25B). Not surprisingly, this construct also restored IP3 and ryanodine receptor distributions to patterns that are comparable to those observed using the full length GFP-220 kDa ankyrin-B ($M_BS_BDC_B$) construct (FIG. 19B). By contrast, ankyrin-B, which has the death domain but lacks the C-terminal domain is unable to localize in a striated A- and Z-line pattern, and is also unable to rescue the localization of either the ryanodine or IP3 receptor (FIG. 25C, bottom panel).

The Ankyrin-B C-Terminal Domain is Necessary for Activity of Ankyrin-B/G Chimeras in Restoration of Normal Contraction Rates of Ankyrin-B (−/−) Cardiomyocytes.

Figure 26:
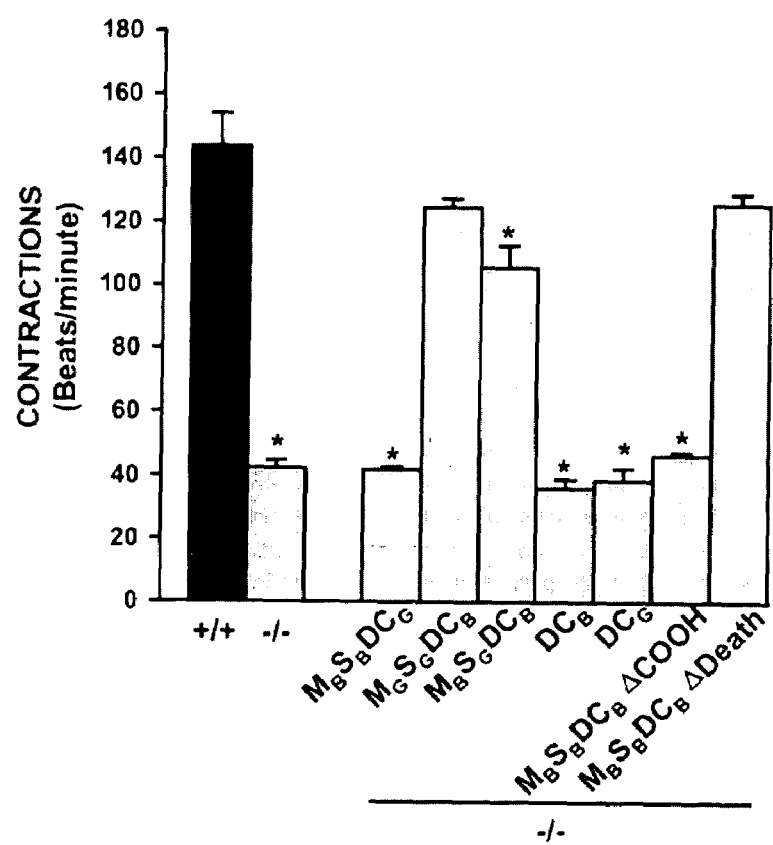
FIG. 26. Ankyrin-B/G chimeras containing the ankyrin-B C-terminal domain restore normal cardiomyocyte contraction rates to ankyrin B (−/−) cardiomyocytes. Neonatal myocytes were transfected with the indicated constructs (see FIGS. 21, 24A, and 25A) and following 24–36 hours, spontaneous contractions were monitored by light microscopy. In each experiment, a mock, GFP, or untransfected control was always included (see FIG. 20). Experiments were performed at least three times with greater than 50 myocytes monitored/culture. * Significant differences from wildtype levels, P<0.05, ANOVA.

Transfection of GFP-ankyrin $M_GS_GDC_B$ restores ankyrin-B (−/−) cardiomyocyte contraction rates nearly to levels observed in wildtype cultures (FIG. 26; 124±3 bpm; P>0.05; n=4 mice). By contrast, transfection of ankyrin $M_BS_BDC_G$ does not restore normal contractility to ankyrin-B (−/−) cardiomyocytes (41±1 bpm, n=4 mice; FIG. 26). These results are in agreement with immunolocalization studies demonstrating requirement of the death/C-terminal domain for activity of ankyrin-B/G chimeras in restoring localization of IP3R and RyR (FIG. 21). It was also determined that constructs encoding only the C-terminal domains of ankyrin-G and ankyrin-B fail to restore wildtype contractility rates to null cultures (38±4 bpm and 36±3 bpm, respectively, n=3 mice; FIG. 26). Finally, transfection of cardiomyocytes with 220 kDa ankyrin-B lacking only the death domain largely restores normal beat frequency (126±3 bpm (n=4 mice)) to ankyrin-B (−/−) myocytes. However, cardiomyocytes expressing GFP-ankyrin-B lacking the C-terminal domain of ankyrin-B (FIG. 26; 46 +1 bpm; n=4 mice) did not display contractility properties that were significantly different from ankyrin-B (−/−) cardiomyocyte cultures (FIG. 26; 42±2 bpm, n=5). These results confirm the requirement of the ankyrin-B C-terminal domain, but not the death domain, in the rescue of IP3 and ryanodine receptor localization and normal contraction rates ankyrin-B (−/−) cardiomyocytes.

This study reports that the C-terminal domain of 220 kDa ankyrin-B is necessary for activity of ankyrin-B/G chimeras for proper localization at the A-band and Z-lines and for restoring the localization of IP3 and ryanodine receptors as well as normal contraction rates to ankyrin-B null cardiomyocytes. The C-terminal domain is not active in the absence of membrane-binding and spectrin-binding domains, indicating that one or more of these domains must cooperate to ensure normal function of ankyrin-B. A major role for the C-terminal domain was initially surprising due to expected activities of the membrane-binding and spectrin-binding domains for ankyrin linkages to spectrin and membrane-associated proteins. However, as multiple ankyrin isoforms are commonly expressed within the same tissue, share closely related membrane- and spectrin-binding domains, but have non-overlapping functions, the C-terminal domains of other ankyrin isoforms may have similar regulatory functions that dictate isoform targeting and binding specificity within the ankyrin family.

Functions of the ankyrin-B C-terminal domain could result, in principle, from intramolecular and/or intermolecular interactions. Evidence for the potential of the C-terminal domain to participate in intramolecular interactions with other ankyrin domains comes from biochemical analysis of the C-terminal domain of ankyrin-R (Hall and Bennett, J. Biol. Chem. 262(22):10537–10545 (1987), Hargreaves et al, J. Biol. Chem. 255(24):11965–11972 (1980), Bennett, Biochim. Biophys. Acta 689(3):475–484 (1982), Bennett and Stenbuck, J. Biol. Chem. 255(13):6424–6432 (1980)). An ankyrin-R variant, lacking 161 residues in the C-terminal domain due to alternative splicing, has an increased affinity for spectrin and the anion exchanger. Moreover, the 161-residue segment binds directly to ankyrin-R, but not to individual spectrin and membrane-binding domains, and can reverse the increased binding affinity for the anion exchanger. These observations led to the proposal that the 161 residues within the C-terminal domain of ankyrin-R bind to a site on ankyrin encompassing both membrane-binding and spectrin-binding domains and functions as an allosteric repressor. Ankyrin-B contains a segment (residues 1600–1760) with limited sequence similarity to the 161 residues of ankyrin-R, although the possibility of alternatively-spliced forms lacking this domain has not been evaluated.

To date, no published information is available regarding intermolecular interactions of the death/C-terminal domain of 220 kDa ankyrin-B or other ankyrins. Moreover, searches of the available data-bases with the ankyrin-B C-terminal domain sequence have not revealed homologies to known protein domains or binding sites. One feature of the C-terminal domain potentially relevant to protein interactions is a predicted amphipathic helix (1778–1788) which could mediate interactions with GTPases or protein kinases (Bernstein et al, J. Biol. Chem. 275(24):18520–18526 (2000), El Far et al, J. Biol. Chem. 276(33):30662–30669 (2001)).

Data from this study exclude the death domain of ankyrin-B in restoration of IP3 and ryanodine receptor localization in primary (−/−) cardiomyocytes. A role for the death domain in other ankyrin functions currently remains unknown. However, this domain in other proteins, such as Fas and p55$^{TNFR}$, activates NFκB, caspase proteases, and contributes to cell death/apoptosis (Kitson et al, Nature 384(6607):372–375 (1996), Liepinsh et al, Embo. J. 16(16): 4999–5005 (1997)). This domain may also form homotypic or heterotypic dimers with other death domains (Kitson et al, Nature 384(6607):372–375 (1996)) suggesting the possibility of ankyrin regulation via homo- or hetero-multimerization (i.e., ankyrin-B/ankyrin-B or ankyrin-B/ankyrin-G multimers). Given the predicted role of the death domain in protein-protein interactions it is possible that this domain contributes to other specialized functions of ankyrin and may be critical in binding other ankyrins, or other unresolved binding partners.

The cellular mechanism involved in 220 kDa ankyrin-B-dependent localization of IP3 and ryanodine receptor to the SR is currently unknown. The fact that 220 kDa ankyrin-B and IP3 or ryanodine receptors do not demonstrate extensive co-localization (see FIG. 23) argues against a simple stoichiometric 1:1 association between 220 kDa ankyrin-B and these receptors at the membrane of the sarcoplasmic reticulum. Immunoprecipitation studies from several laboratories have demonstrated interactions between IP3R and ankyrins from native brain tissue and cultured cells (Bourguignon et al, J. Biol. Chem. 268(10):7290–7297 (1993), Hayashi et al, J. Pharmacol Exp. Ther. 293(3):788–798 (2000), Hayashi and Su, Proc. Natl. Acad. Sci. USA 98 (2):491–496 (2001)). Future experiments will address the nature of ankyrin-B/calcium-release channel interactions to determine if these are direct or indirect and if they are modulated by the C-terminal domain.

Ankyrin-B interactions with IP3R may be dynamically regulated depending on internal and external cues perhaps mediated by the unique C-terminal domain. Using GFP-ankyrin-B constructs which have altered death/C-terminal domains, specifically construct $M_B S_B DC_G$, a potential transient intermediate compartment has been identified where ankyrin and IP3R are colocalized (see FIG. 23, right). Further identification and characterization of these putative intermediates is important in determining the precise role of ankyrin-B in calcium-release channel localization and function. It will be determined whether these structures represent a membrane compartment, and, if so, the dynamic relationship of these membranes to the endoplasmic reticulum.

Figure 27:
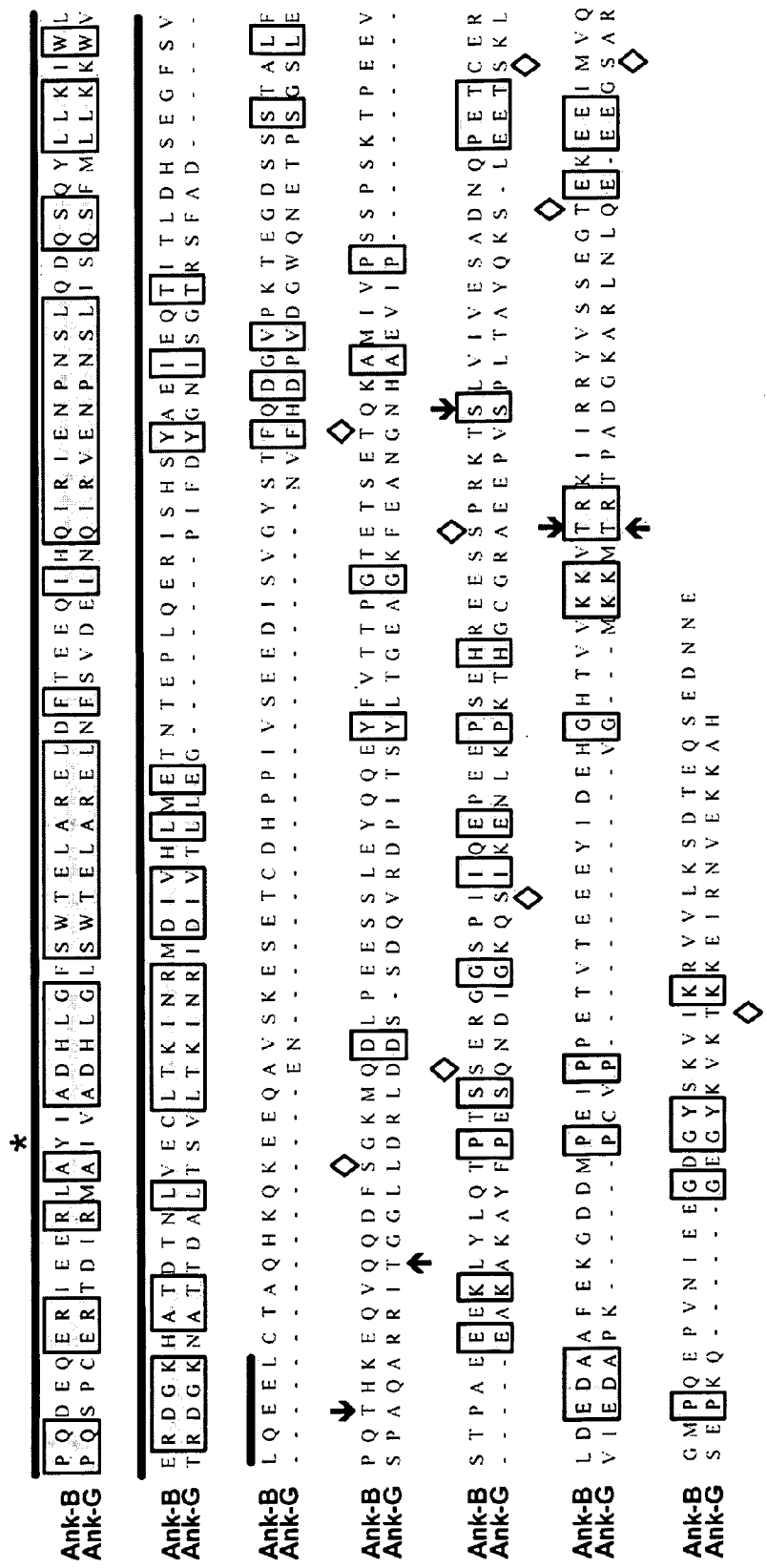
FIG. 27. Comparison of amino acid sequences of the death/C-terminal domains of ankyrin-B and ankyrin-G. The Death/C-Terminal domains of 220 kDa ankyrin-B (upper) (SEQ ID NO: 1) and 190 kDa ankyrin-G (lower) (SEQ ID NO: 2) which contain the death domain and the COOH-domain were aligned using MacVector (Accelrys; Burlington, Mass.). Shaded boxes represent conserved homology between these two molecules. The solid dark line above the sequence delineates the death domain. Symbols: arrows represent predicted PKA phosphorylation sites; open diamonds represent predicted PKC phosphorylation sites; and the asterisk shows one predicted tyrosine kinase site.

Ankyrin-B is localized in a striated pattern beginning in the initial stages of cardiomyocyte development (i.e., at 2 days in culture), while IP3 and ryanodine receptors also appear to be expressed at this stage, but are not localized in a striated pattern until 4 to 5 days in culture. These observations suggest a developmentally regulated expression of a protein or signaling pathway is required to initiate the ankyrin-B-dependent localization of IP3 receptor and ryanodine receptor. The fact that localization of ryanodine receptors (but not IP3 receptor) is normal in adult cardiac tissue and cardiomyocytes argues that at a certain developmental time, the cues which confer normal localization to IP3 and ryanodine receptors diverge. Phosphorylation of the 220 kDa ankyrin-B C-terminal domain may provide this cue for ankyrin-B-dependent localization of calcium-release proteins in the ER/SR membrane. It is of particular interest that multiple putative phosphorylation sites are predicted within this domain including two protein kinase A, seven protein kinase C, sixteen casein-kinase II, and one tyrosine kinase site (FIG. 27; Expasy Prosite; www.expasy.org).

In conclusion, the results from this rescue study indicate that the C-terminal domain of ankyrin-B is critical for the normal localization of ankyrin-B, IP3R and RyR in neonatal cardiomyocytes. Extrapolation of these findings indicates that C-terminal domains in other ankyrins may also be required for dictating specificity for ankyrin function in diverse tissues. Both ankyrin-G and ankyrin-B isoforms have been implicated in the delivery of protein to specialized membrane sites (Peters et al, J. Cell Biol. 130(2):313–330 (1995), Tuvia et al, J. Cell Biol. 147(5):995–1008 (1999), Devarajan et al, J. Cell Biol. 133(4):819–830 (1996)). However, unlike ankyrin-G polypeptides that have been characterized at cell membranes in various cell types, ankyrin-B appears to be intimately involved in the regulation ER/SR calcium compartment. Therefore, these isoforms appear to have similar, but non-overlapping roles, in the organization of protein complexes. Based on the results of the current study, it is believed that the divergent roles of ankyrins are dependent on their C-terminal domains

EXAMPLE 5

Ankyrin-B Dysfunction Leads to Lethal Cardiac Arrhythmias and Type 4 LQT Syndrome Experimental Details Human mutation analysis. Genomic DNA was prepared from peripheral blood lymphocytes. Mutation analysis was conducted by direct sequencing of the ankyrin-B gene. All 45 exons of the ankyrin-B gene were amplified using intronic primers.

AnkB+/− cardiomyocytes. GFP-ankyrin-B E1425G was created using standard molecular techniques. Neonatal cardiomyocytes were prepared, transfected (Mohler et al, J. Biol. Chem. 277:10599 (2002)) and imaged using Fluo3-AM (Tuvia et al, J. Cell Biol. 147:995 (1999)). Transfection was optimized for low GFP-AnkB expression (levels undetectable without GFP-antisera (Mohler et al, J. Biol. Chem. 277:10599 (2002))). Following Ca$^{2+}$ imaging, cells were immunostained using indicated antisera and visualized using Alexa 568 so that signal would not interfere with Fluo3-fluorescence. For contraction experiments, >100 cells were monitored for each condition. For rescue experiments, Ca$^{2+}$ was monitored in >10 cells for each condition.

Immunoblotting and immunoprecipitations. Quantitative immunoblots were performed using equal protein concentrations as described (Tuvia et al, J. Cell Biol. 147:995 (1999)). Adult heart immunoprecipitations were performed using standard techniques (lysis buffer=1.5% Triton X-100, 0.5% deoxycholate plus 2×protease inhibitor cocktail, most proteins were soluble except for IP3R (40%)). Immunoblotting was performed using $^{125}$I-protein A and intensities were quantitated by phosphorimaging (Mohler et al, J. Biol. Chem. 277:10599 (2002)).

Immunostaining and imaging. +/+ and AnkB+/− cells were prepared and imaged identically as described (pinhole, laser power, PMT, magnification, Z-position, etc (Mohler et al, J. Biol. Chem. 277:10599 (2002))). Antibodies: α-actinin, dystrophin, DHPR (Sigma), IP3R types 1,2 (ABR), pan-IP3R (Calbiochem), PMCA2; RyR2, SERCA2 (ABR), GFP (Chemicon, Clontech), NCX1 (RDI), Na/K ATPase α1 (DSHB; Upstate; Michael Caplan, Yale University) α2 (Upstate), ERG1, connexin-43 (Chemicon); Nav1.6, Kir2.1, Kir2.3, MinK (Alomone); Nav1.5 (William Catterall, U. Washington), KCNQ1 (KvLQT1, Santa Cruz), and ankyrin-B monoclonal and affinity-purified polyclonal Ig. Similar results were obtained in both isolated cardiomyocytes and in sections of adult cardiac muscle.

Patch clamp methods. AnkB+/− and +/+ animals (1–3 months of age) were sacrificed by IP injection of pentobarbital sodium (100 mg/kg). Single myocytes were isolated (Santana et al, J. Physiol. 503:21 (1997)). Axopatch-200A or -200B amplifier (Axon Instruments) was used to measure membrane currents (Santana et al, J. Physiol. 503:21(1997), Santana et al, Science 279:1027 (1998)). Patch pipette (1–3 MOhm) solution (mM): CsCl (130); NaCl (10); MgATP (5); Hepes (10), $MgCl_2$ (1) PH 7.2 (with CsOH). Superfusion solution 1: (mM) NaCl (140), KCl (5) $MgCl_2$ (0.5), $CaCl_2$ (1.8), $NaH_2PO_4$ (0.33), glucose (5.5) and HEPES (5); pH 7.4 at 35–37° C. Solution 2 was same as solution 1 but with CsCl substituted for KCl. After conversion to whole cell, voltage clamp in solution (1), solution (2) was used to measure $I_{Ca}$. Test depolarizations followed four 50 ms depolarizations to 0 mV at 1 Hz. A 500 ms ramp-depolarization from 90 mV to 40 mV was followed by a 50 ms period at 40 mV before test depolarizations.

AP recordings. Myocytes were superfused with Solution 1. β adrenergic stimulation of cells produced by the addition of 1 μM isoproterenol to solution 1. Pipette filling solution as above, except KCl was substituted for CsCl (pH 7.2 with KOH). Axopatch 200A was used in current clamp mode to record AP. Current injections triggered AP at constant rate (1 Hz, 5 Hz). All experiments were performed at 37° C.

Confocal $[Ca^{2+}]i$ imaging. Biorad MRC600 and Zeiss LSM510 microscopes were used with simultaneous electrical measurements to determine $[Ca^{2+}]i$, AP trajectory or membrane current (Santana et al, J. Physiol. 503:21 (1997), Gomez et al, Science 276:800 (1997)). In parallel experiments measurements of resting $[Ca^{2+}]i$ were obtained by adding indo-1 (25 BM) (duBell et al, J. Physiol. 493:793 (1996)) to the pipette filling solution, on a system made by the authors. Resting $[Ca^{2+}]i$ was calculated as described (duBell et al, J. Physiol. 493:793 (1996)).

Statistics. Data were analyzed using either paired two-tailed t-tests or two-way ANOVA, and P values <0.05 were considered significant. Data are expressed as means +/− SEM.

Results

Figure 28A:
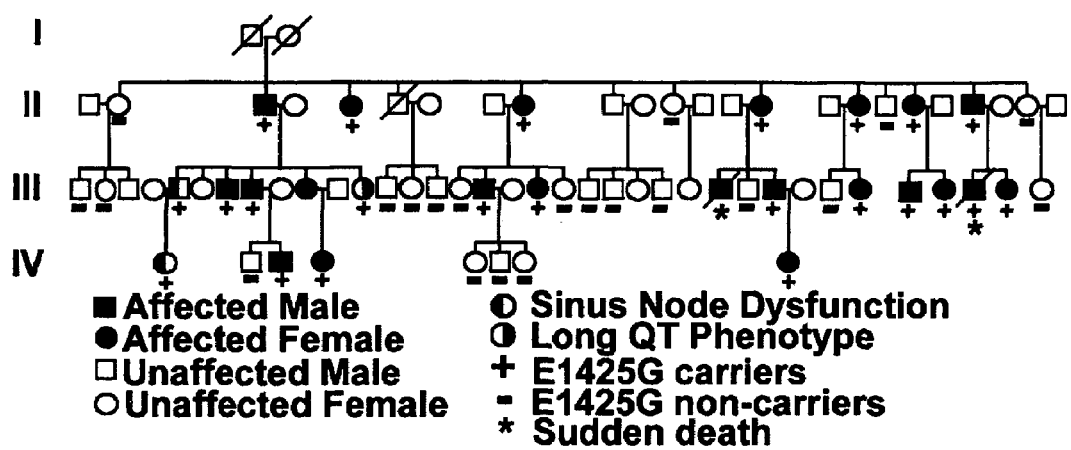
FIGS. 28A–28C. Loss-of-function mutation in ankyrin-B in LQT type 4 syndrome.

A large French kindred was previously characterized (FIG. 28A) where long QT syndrome associated with sinus node dysfunction and episodes of atrial fibrillation segregates as an autosomal dominant trait and maps to an 18 cM interval on chromosome 4q25-27 (Schott et al, Am. J. Hum. Genet. 57:1114 (1995)). Among the 25 affected patients (21 adults, 4 children) included in the study, average QTc was respectively 490±30 ms and 465±38 ms vs 380±30 ms and 403±36 ms in unaffected individuals. T-wave morphologies characterized by sinusoidal features differed from those observed in the LQT1–3. Sinus node bradycardia or junctional escape rhythm was diagnosed in all patients with LQT43, though 24-hour ECG recordings revealed that sinus node dysfunction alternated with normal sinus rhythm. Nine patients were equipped with a rate-responsive atrial pacemaker because of marked bradycardia and the need of beta blocking therapy. Finally, episodes of atrial fibrillation were diagnosed in 12 adult patients but were absent during childhood. Since the initial description of the family, 8 additional individuals were born. Four were demonstrated to carry the LQT4 haplotype. Sinus node abnormalities were diagnosed in utero in all affected members from generation IV.

Figure 28B:
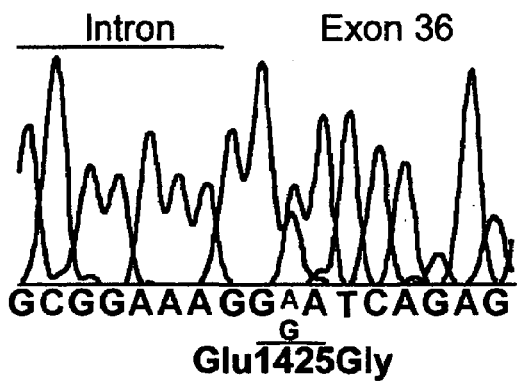

Sequencing of the gene encoding ankyrin-B identified a 4274 A→G transition mutation in exon 36 resulting in substitution of glycine for a glutamic acid at amino acid 1425 (E1425G) near the regulatory domain of 220 kDa ankyrin-B (FIG. 28B). No nucleotide alterations were identified in two other positional candidate genes encoding CAMKII-δ or TRP3. 45 family members (24 carriers, including one individual who suffered sudden death, and 21 non-carriers) were evaluated for the E1425G mutation. The E1425G mutation segregated with LQT in 22/24 individuals (III-5 and IV-1 were non-penetrant with QTc=420 ms), and with sinus node dysfunction in 23/24 individuals (III-12 was non-penetrant with a heart rate of 60 beats/min). The E1425G mutation was not found in more than 400 control alleles.

Figure 28C:
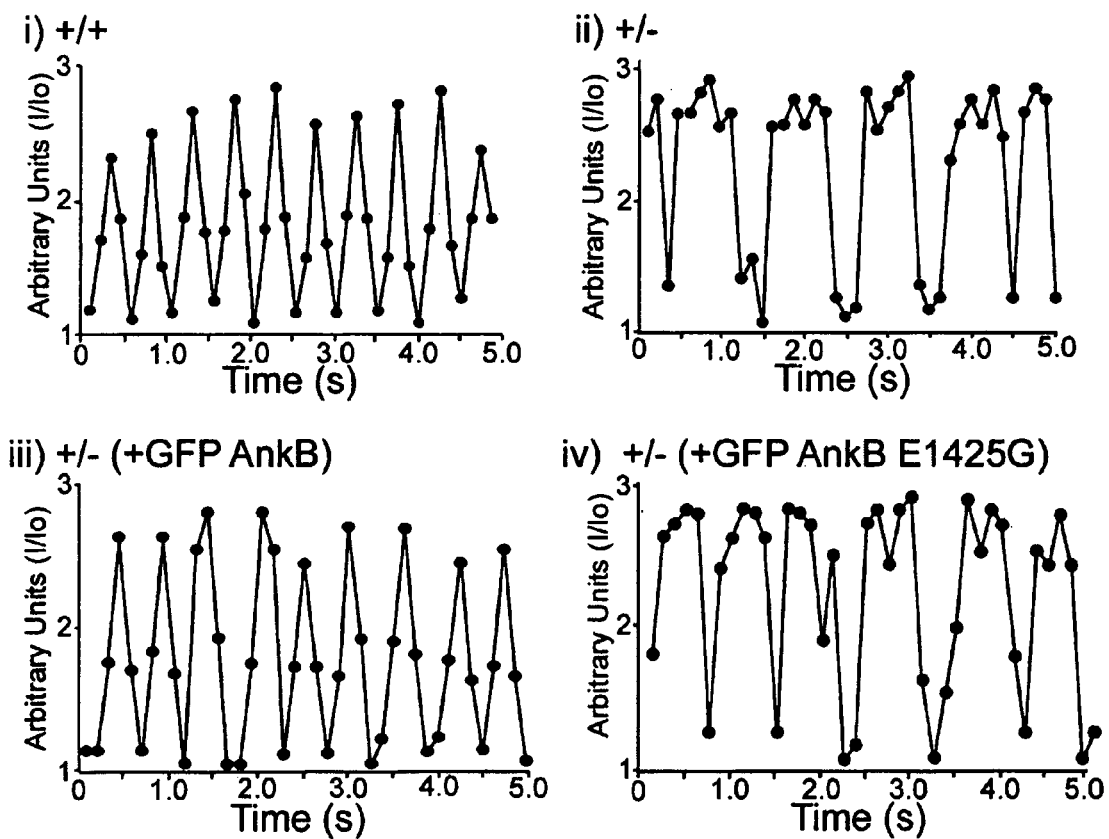

Functional activity of the E1425G mutant was evaluated based on ability to rescue abnormal $Ca^{+2}$ dynamics of AnkB+/− neonatal cardiomyocytes obtained from mice heterozygous for a null mutation in the gene encoding ankyrin-B (Tuvia et al, J. Cell Biol. 147:995 (1999), Mohler et al, J. Biol. Chem. 277:10599 (2002)) (neonatal cardiomyocytes were used as adult cardiomyocytes are not readily transfected). Ankyrin-B expression in +/− cells is reduced and localized to a striated pattern only in certain regions of these cells. AnkB+/− cardiomyocytes have a decreased spontaneous contraction rate (144+/−10 to 78+/−8 bpm, p<0.05) associated with prolonged $[Ca^{2+}]i$ transients at a lower frequency (FIG. 28C; 2.7 to ~1.3 Hz; p<0.05). These defects in +/− cardiomyocytes can be rescued by transfection with cDNA encoding GFP-tagged 220 kDa ankyrin-B (FIG. 28C; $Ca^{+2}$ waves ~2.2 Hz, rhythm restored 134+/−11 bpm). In contrast, AnkB+/− cardiomyocytes transfected with ankyrin-B containing the human E1425G mutation still displayed abnormal $Ca^{+2}$ oscillations (FIG. 28C; ~1.3 Hz; with instances of prolonged elevations in cytosolic $Ca^{+2}$, p<0.05) and a decreased beat frequency (71+/−12 bpm, p<0.05), even though the mutant GFP-ankyrin-B itself targeted normally. Therefore, two normal copies of the ankyrin-B gene are required for normal $Ca^{+2}$ signaling, and the E1425G mutation leads to loss-of-function. Ankyrin-B is the first identified protein implicated in a congenital long QT syndrome that is not an ion channel or channel subunit (Keating et al, Cell 104:569 (2001), Towbin et al, Am. J. Med. 110:385 (2001)).

Figure 29E:
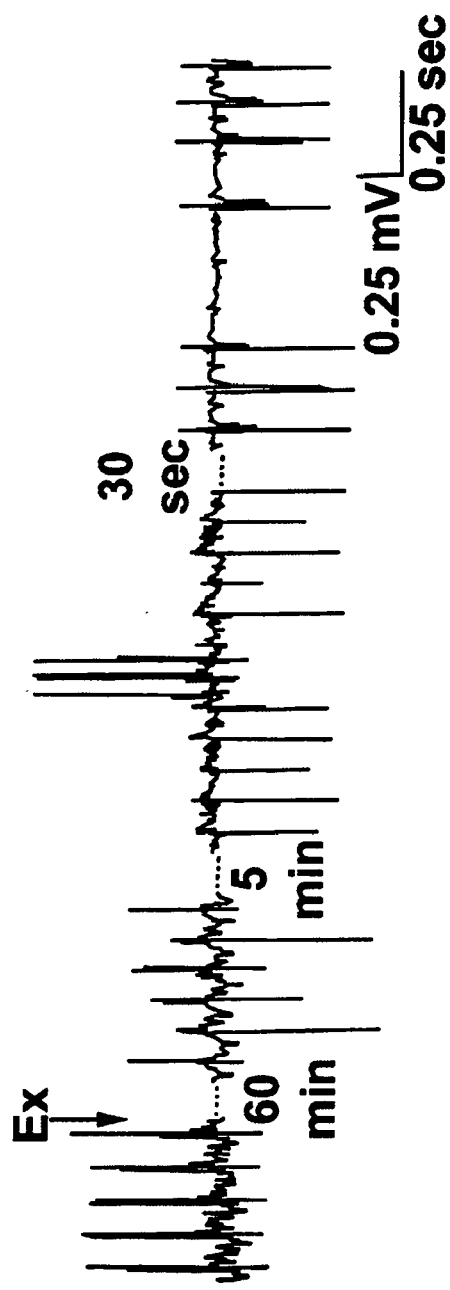

Analysis of ECGs and heart rates of unrestrained animals using implanted radiotransmitter electrodes revealed significant similarities in cardiac phenotype between humans with LQT4 and AnkB+/− mice (FIG. 29). AnkB+/− mice have bradycardia with a conscious resting heart rate of 515±49 bpm, compared to 641±31 bpm for +/+ (n=12 +/+, 14 +/−, p<0.05). Bradycardia was observed in all +/− mice, with +/− mice displaying a heart rate <600 bpm for 87±3.4% of a 30 min interval, while +/+ mice spent 4.3±1.7% of the same interval at <600 bpm (n=10 +/+, 10 +/−; p<0.05). AnkB+/− mice also exhibit a high degree of heart rate variability (FIG. 29A,B) associated with multiple episodes of abrupt sinus slowing. One episode is shown in the ECG trace for a +/− animal (FIG. 29C). The prolonged RR intervals (sinus slowing, * in FIG. 29B) occur on a background of reduced heart rate (FIG. 29A) compared to +/+ animals. In addition, AnkB+/− mice exhibit episodes of intermittent isorhythmic AV dissociation similar to rhythm disturbances present in human LQT4 patients. ECG abnormalities in AnkB+/− mice are not due to electrolyte or obvious structural defects in the heart, since no significant differences between +/+ and AnkB+/− mice were evident in serum $K^+$, $Na^+$, $Mg^{2+}$ or $Ca^{2+}$ and no histopathological defects were detected in sections of AnkB+/− hearts.

The rate-corrected QT interval (QTc) is significantly prolonged from 25±1.0 to 30±1.1 ms in AnkB+/− mice (n=9 +/+, 11 +/−; p<0.05). The difference in apparent QT length in a mouse ECG could be due to delayed conduction and/or delayed repolarization (Casimiro et al, Proc. Natl. Acad. Sci. USA 98:2526 (2001)). ECGs of AnkB+/− mice, in contrast to humans with LQT4, reveal general slowing of conduction with PR intervals increased from 35.9±1.0 ms to 39.6±0.7 ms, QRS intervals increased from 8.3±0.1 to 11.2±0.2 ms, and P wave duration increased from 8.2±0.7 to 13.4±0.5 ms (n=9 +/+, 11 +/−; all differences statistically significant, p<0.05). Given that action potentials of adult AnkB+/− cardiomyocytes are not substantially prolonged, the increase in QT interval observed in AnkB+/− mice is likely due to delayed conduction.

Figure 29F:
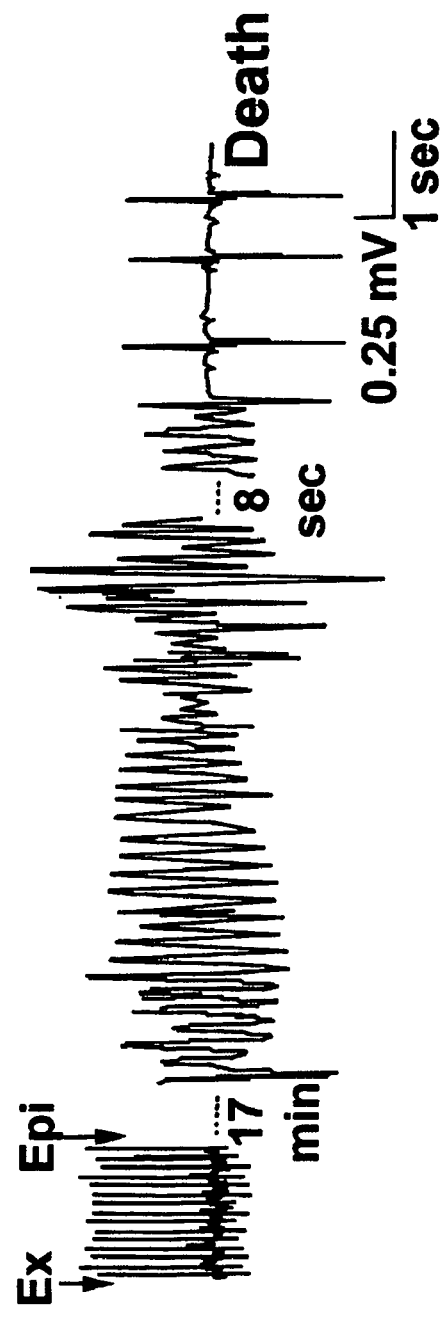

Sudden cardiac death in humans with the E1425G mutation occurred secondary to physical exertion and emotional stress (FIG. 28)3. An attempt was made to mimic these circumstances in mice with exercise followed by injection with epinephrine. The mice responded in a dramatic manner. Two of 14 AnkB+/− mice became unresponsive for 3–10 sec immediately following exercise alone. Over half of AnkB+/− mice (8/14) died following exercise combined with epinephrine. No +/+ mice ever became unresponsive or died during these experiments (0/6). Exercised AnkB+/− mice displayed instances of reversed polarity of the QRS complex (2 mice), and second-degree atrio-ventricular block (P wave with no QRS complex, 11 mice, FIG. 29E). Prolonged polymorphic ventricular arrhythmia immediately preceding death was recorded in 2 mice treated with exercise plus epinephrine (FIG. 29F). The additional 6 mice that died from exercise and epinephrine displayed multiple short episodes (1–2 sec) of polymorphic ventricular arrhythmia within 0–2 minutes before death. No arrhythmic episodes were observed in +/+ mice ECGs following exercise or exercise plus epinephrine.

Figure 30A:
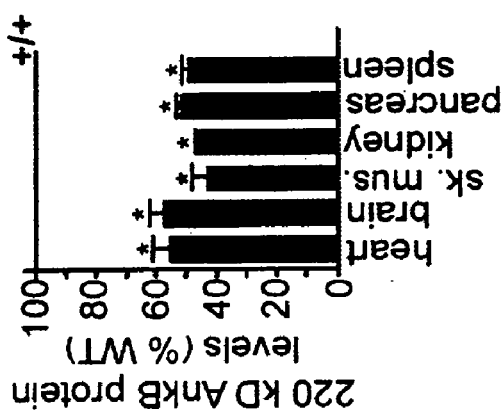
FIGS. 30A–30F. Coordinate reduction of ankyrin-B and ankyrin-B-associated proteins at Z-line/T-tubules of adult AnkB+/− cardiomyocytes.
Figure 30B:
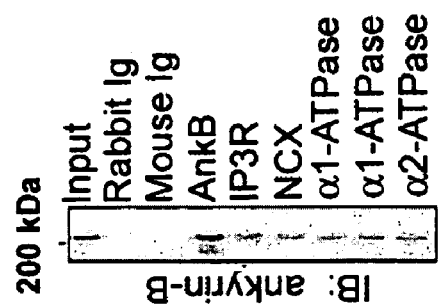
Figure 30C:
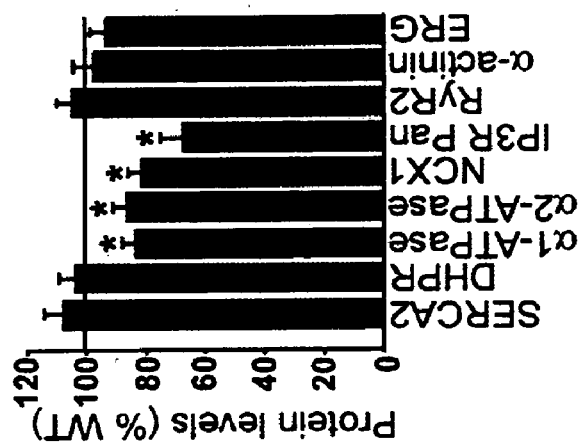
Figure 30D:
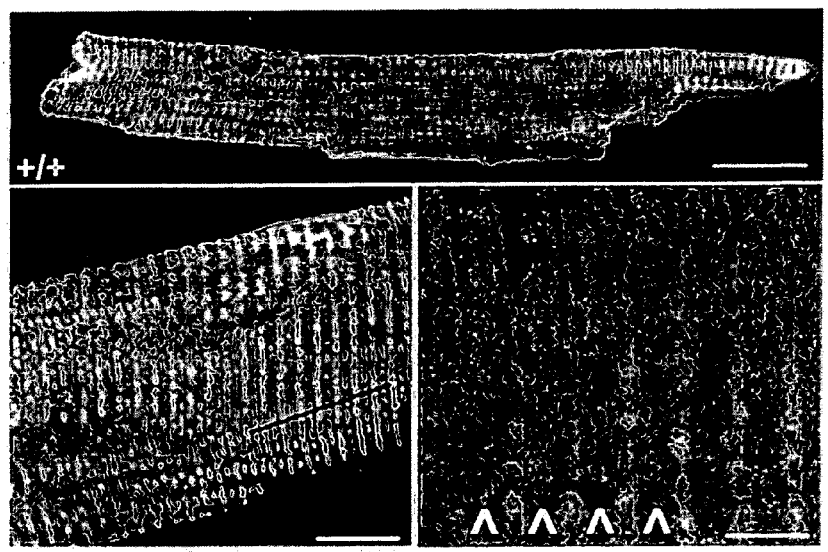
Figure 30E:
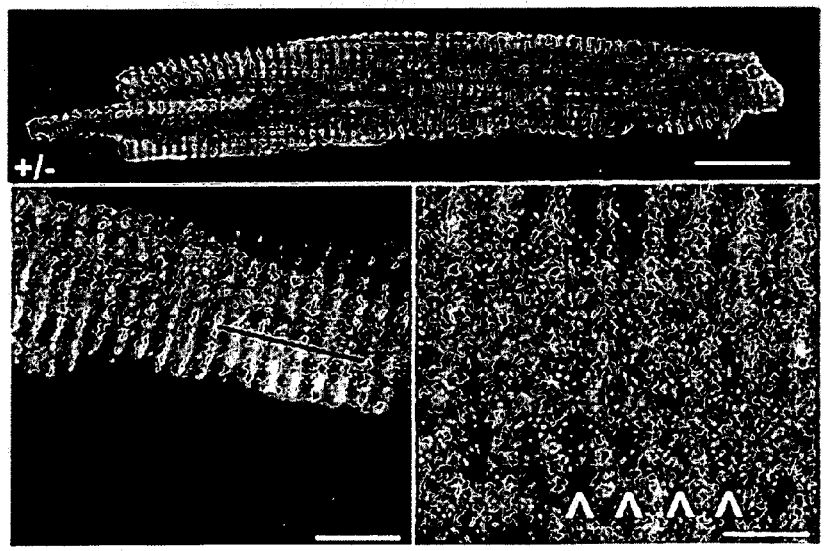

Reduction of 220 kDa ankyrin-B levels by ~50 percent in immunoblots of adult cardiac tissue in AnkB+/− mice (FIG. 30A) is accompanied by selective loss of ankyrin-B staining at the Z-line/T-tubule region of AnkB+/− cardiomyocytes (localization at the Z-line/T-tubule based on confocal Z-sections using DHPR as a T-tubule marker, FIG. 30D). Ankyrin-B staining is retained at the M-line (predominant staining), and intercalated discs (FIG. 30E). Ankyrin-B also is aligned with Z-lines in skeletal muscle, but, in contrast to cardiomyocytes, skeletal muscle ankyrin-B is restricted to costameres at the sarcolemma4.

The co-ordinate loss of ankyrin-binding proteins Nav1.6, beta IV spectrin, and neurofascin at axon initial segments lacking ankyrin-G (Jenkins et al, J. Cell Biol. 155:739 (2001)) suggested that reduced levels of ankyrin-B at Z-lines/T-tubules in heart could also result in deficiency of ankyrin-B-associated proteins at T-tubules. Na/K ATPase, Na/Ca exchanger (NCX) and IP3R are candidate ankyrin-binding proteins based on biochemical data (Bennett et al, Physiol. Rev. 81:1353 (2001)) that are localized at T-tubules (Frank et al, in The Myocardium (ed. Langer, G A) 1–32 (Academic Press, San Diego, Calif., 1997)). Ankyrin-B co-immunoprecipitates with NCX1, α1 and α2 ATPase, and IP3R from extracts of heart tissue (FIG. 30B), but not with other cardiomyocyte proteins (including DHPR, SERCA2, and calsequestrin). Levels of IP3R (pan IP3R), α1 and α2 Na/K ATPase subunits, and NCX in isolated adult cardiomyocytes are reduced by 15–33% in AnkB+/− cardiomyocytes by immunoblots (FIG. 30C). Measurements of binding of [$^3$H] IP3 (ligand for IP3R) and of [$^3$H] ouabain (ligand for Na/K ATPase) to adult cardiac microsomes also demonstrated a 33% and 16% reduction, respectively, in capacity in AnkB+/− heart, while affinities for these ligands were unchanged. In contrast, by quantitative western blot analysis, protein levels of ER/SR components (SERCA2, calreticulin, calsequestrin), K+ channels or associated subunits (KCNQ1/KvLQT1, ERG1, MinK/IsK, Kir2.1/IRK1, Kir2.3/IRK3), RyR2, plasma membrane $Ca^{+2}$ channels (DHPR, PMCA2), and structural proteins (α-actinin, dystrophin) are unaffected (FIG. 30C). Northern blots revealed no difference in levels of mRNA encoding IP3R (type 1 and pan), α1 and α2 Na/K ATPase subunits, and NCX1.

Figure 30F:
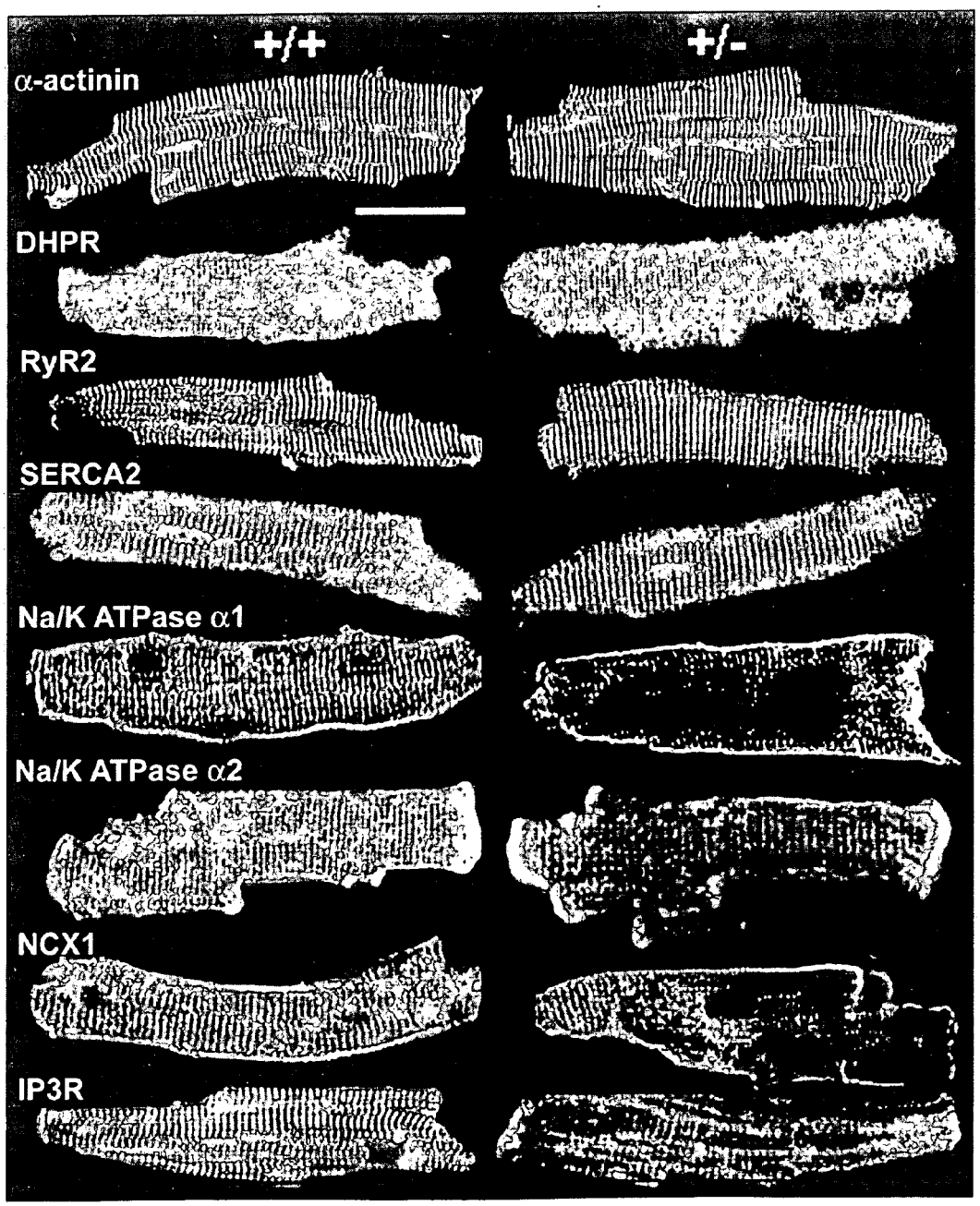

The modest overall reduction in levels of NCX, Na/K ATPase, and IP3R has a substantial impact on levels of these proteins localized at T-tubule sites that is easily seen by immunofluorescence (FIG. 30F). NCX, as well as α1 and α2 Na/K ATPase are preferentially reduced in AnkB+/− cardiomyocytes at T-tubule sites while little change can be detected at the sarcolemma or intercalated discs. IP3R in AnkB+/− cardiomyocytes also are reduced at T-tubule sites as well as disorganized in some regions, while label at intercalated discs is relatively normal Markers for T-tubules (DHPR), the SR (SERCA2), and Z-line components (α-actinin) (Frank et al, in The Myocardium (ed. Langer, GA) 1–32 (Academic Press, San Diego, Calif., 1997)) are unaltered in AnkB+/− cardiomyocytes (FIG. 30F). Proteins also unaffected as monitored by confocal analysis included dystrophin, connexin 43, Nav1.5, Nav1.6, ERG1, PMCA2, KCNQ1/KvLQT1, calsequestrin, and calreticulin. Ankyrin-B-dependent expression of IP3R, NCX, or Na/K ATPase may be a specialized feature of cardiac muscle, as there is no difference in expression or localization of these proteins in skeletal and vascular smooth muscle.

Reduction of Na/K ATPase, NCX, and IP3R in neonatal AnkB+/− cardiomyocytes, can be rescued by transfection with GFP-tagged 220 kDa ankyrin-B but not by 220 kDa ankyrin-B containing the E1425G mutation. 220 kDa ankyrin-B thus is necessary and sufficient for normal expression of NCX, Na/K ATPase, and IP3R in neonatal cardiomyocytes, and the same E1425G mutation causing clinical arrhythmia in humans abolishes this activity. These findings establish the principle that ankyrin-B participates in expression of multiple ion channel/transporter proteins.

Figure 31A:
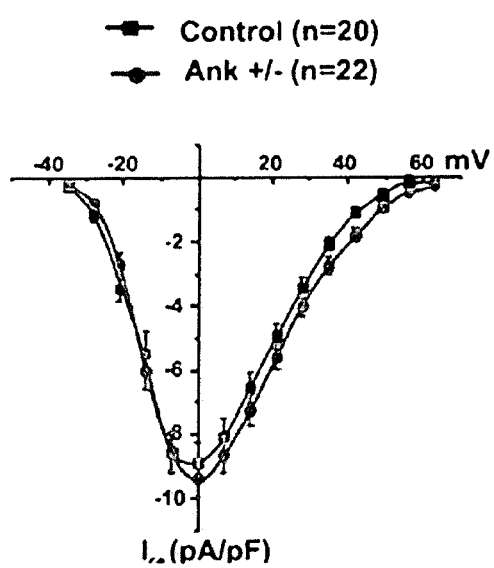
FIGS. 31A–31C. Ca$^{2+}$ signaling in adult AnkB+/− ventricular cardiomyocytes.
Figure 31B:
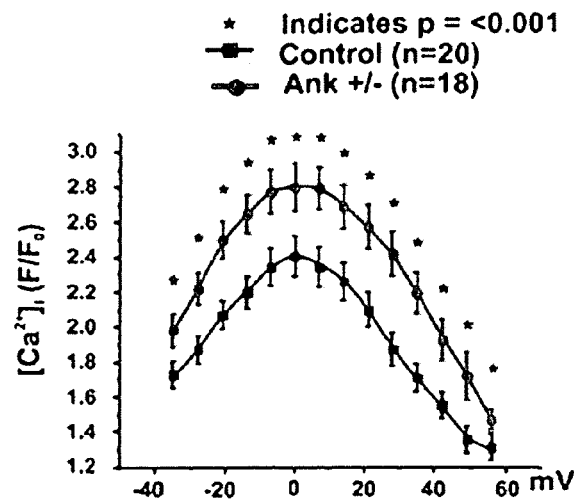

Examination of the electrical behavior and $Ca^{2+}$ dynamics of isolated heart cells from adult +/− animals with ECG defects revealed a significant increase in the peak [$Ca^{2+}$]i level at all potentials (FIG. 31). No significant differences in resting levels of [$Ca^{2+}$]i (~160 nM) were observed using indo-1. An increased [$Ca^{2+}$]i transient under these conditions implies that the amount of $Ca^{2+}$ in the SR is elevated, although these values were not experimentally determined. No significant changes were evident in the magnitude or voltage dependence of the L-type $Ca^{2+}$ channel current between −40 mV and +60 mV. (ICa; FIG. 31A). While heart weights were similar between +/+ and AnkB+/− mice (indicating no overt hypertrophy accompanied elevated intracellular Ca2+), AnkB+/− cardiomyocytes did exhibit ~23% increase in capacitance, suggesting increased surface area and a small increase in cell volume.

Figure 31C:
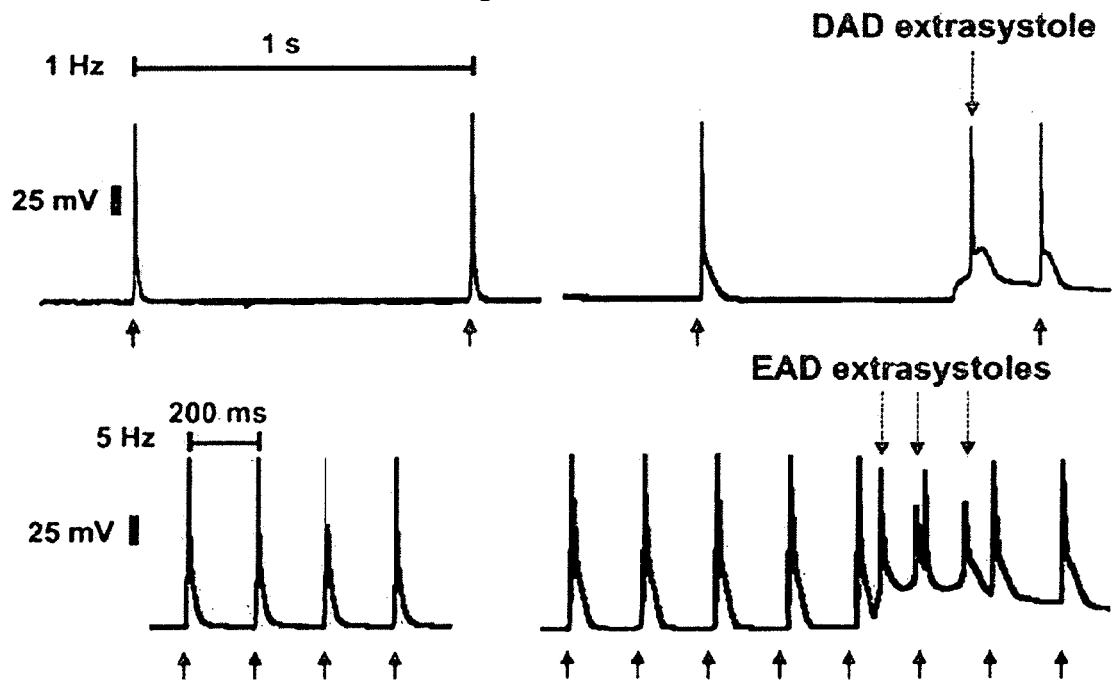

Cardiac action potentials (APs) measured in the presence and absence of isoproterenol revealed stress-induced abnormalities in AnkB+/− heart cells (FIG. 31C). These cells were not significantly different from control cells under control conditions (+/+AP$_{90}$=12.3 +/−1.0 (n=8; +/−AP$_{90}$=15.0+/−1.4 (n=17), where AP$_{90}$=time for 90% repolarization). However, following acute application of isoproterenol (1 BM) to simulate conditions of stress, APs in AnkB+/− cardiomyocytes developed spontaneous extrasystoles at both 1 and 5 Hz, while control cells did not. Both delayed afterdepolarizations (DAD's) and early afterdepolarizations (EAD's) were observed in AnkB+/− cells, and the DAD's and EAD's led to extrasystoles. The appearance of EADs, DADs and extrasystoles suggest that these triggered arrhythmic mechanisms underlie the lethal arrhythmias seen in humans with the E1425G mutation, and could be caused by elevated [$Ca^{2+}$]i11. A causative role of increased [$Ca^{2+}$]i in cardiac arrhythmia and congenital sudden cardiac death is an emerging area of interest, with current examples including gain of function mutations in the RyR$_2$ $Ca^{2+}$-release channel (Marks et al, J. Cell. Physiol. 190:1 (2002)).

Elevation in the [$Ca^{2+}$]i transient in AnkB+/− myocytes can be rationalized by loss of Na/K ATPase isoforms (Blaustein et al, Physiol. Rev. 79:763 (1999), Reuter et al, Circ. Res. 90:305 (2002)). A small reduction of Na/K ATPase would be expected to mimic effects of cardiac glycosides such as digitalis, a Na/K ATPase inhibitor (Bers, Excitation-Contraction Coupling and Cardiac Contractile Force (Kluwer Academic Publishers, Dordrecht (2001)). Na/K ATPase inhibition results in increased [$Ca^{2+}$]i by first producing an increase in [$Na^+$]i leading to a reduction of $Ca^{2+}$ extrusion by the NCX (Blaustein et al, Physiol. Rev. 79:763 (1999), Reuter et al, Circ. Res. 90:305 (2002)) into the extracellular space. In the face of unchanged $Ca^{2+}$ entry by $I_{Ca}$, and combined with a small reduction in NCX, the reduction of Na/K ATPase in AnkB+/− cells should lead to an increase in total cellular $Ca^{2+}$, as indicated by the data provided. Long-term reduction or increase in NCX in animal models does not appear to produce a severe phenotype because of diverse compensatory mechanisms (Philipson et al, Annu. Rev. Physiol. 62:111 (2000)). Therefore, the loss of Na/K ATPase is likely the major contributor to elevated [$Ca^{2+}$]i transients in AnkB+/− ventricular myocytes.

In summary, this work shows that ankyrin-B plays an important role in regulating the coordinated expression of NCX, the Na/K ATPase, IP3R and possibly other ankyrin-binding proteins. Importantly, ankyrin-B dysfunction in humans leads to lethal cardiac arrhythmias and type 4 LQT syndrome.

All documents cited above are hereby incorporated in their entirety by reference.

What is claimed is:

1. A method of screening a test agent for the ability to increase or decrease the binding association of 220 kDa ankyrin-B with a 220 kDa binding target in an isolated cell and/or isolated cells, comprising:
    (i) contacting 220 kDa ankyrin-B, the membrane-binding domain of 220 kDa ankyrin-B, the spectrin-binding domain of 220 kDa ankyrin-B, or the death or C-terminal domain of 220 kDa ankyrin-B, with an inositol 1,4,5-triphosphate or ryanodine receptor binding target thereof in the presence and absence of said agent, and
    (ii) determining the effect of said test agent on the binding association of 220 kDa ankyrin-B, the membrane-binding domain of 220 kDa ankyrin-B, the spectrin-binding domain of 220 kDa ankyrin-B, or the death or C-terminal domain of 220 kDa ankyrin-B with said binding target wherein said test agent that increases or decreases said binding association is a candidate regulator of said binding association of the membrane-binding domain of 220 kDa ankyrin-B, the spectrin-binding domain of 220 kDa ankyrin-B, or the death or C-terminal domain of 220 kDa ankyrin-B.

2. The method according to claim 1 wherein said 220 kDa ankyrin-B, said membrane-binding domain of 220 kDa ankyrin-B, said spectrin-binding domain of 220 kDa ankyrin-B, or said death or said C-terminal domain of 220 kDa ankyrin-B, or said binding target, is present in a fusion protein.

3. The method according to claim 1 wherein said isolated cell and/or isolated cells is an ankyrin B(+/−) cell.

4. The method according to claim 1 wherein at least one of said 220 kDa ankyrin-B, said membrane-binding domain of 220 kDa ankyrin-B, said spectrin-binding domain of 220kDa ankyrin-B, or said death or said C-terminal domain of 220 kDa ankyrin-B, said binding target and said test agent is bound to a solid support.

5. The method according to claim 1 wherein at least one of said 220 kDa ankyrin-B, said membrane-binding domain of 220 kDa ankyrin-B, said spectrin-binding domain of 220 kDa ankyrin-B, or said death or said C-terminal domain of 220 kDa ankyrin-B, said binding target and said test agent is bound to a solid support.

* * * * *